United States Patent [19]

Okada et al.

[11] Patent Number: 5,312,829
[45] Date of Patent: May 17, 1994

[54] INDOLE DERIVATIVES

[75] Inventors: Satoshi Okada; Kozo Sawada; Natsuko Kayakiri; Yuki Saitoh, all of Tsukuba; Hirokazu Tanaka, Tsuchiura; Masashi Hashimoto, Toride, all of Japan

[73] Assignee: Fujisawa Pharmaceutical Co., Ltd., Osaka, Japan

[21] Appl. No.: 956,579

[22] Filed: Oct. 6, 1992

Related U.S. Application Data

[63] Continuation of Ser. No. 792,595, Nov. 15, 1991, abandoned, which is a continuation-in-part of Ser. No. 757,522, Sep. 11, 1991, Pat. No. 5,212,320, which is a continuation-in-part of Ser. No. 702,500, May 20, 1991, abandoned.

[30] Foreign Application Priority Data

May 21, 1990 [GB] United Kingdom ............... 9011335

[51] Int. Cl.$^5$ ................. C07D 209/10; C07D 405/04; A61K 31/405
[52] U.S. Cl. .................... 514/419; 548/455; 548/492
[58] Field of Search ............ 548/455; 549/492; 514/419

[56] References Cited

U.S. PATENT DOCUMENTS 3,856,967 12/1974 Allais et al. ............... 424/274

FOREIGN PATENT DOCUMENTS 0171037 8/1985 European Pat. Off. .

OTHER PUBLICATIONS

European Journal of Medicinal Chemistry Chimie Therapeutica, vol. 10, No. 2, Mar.-Apr. 1975, pp. 187-199, Chatenay-Malabry, FR: A. Allais et al.
Journal of Medicinal Chemistry, vol. 17, No. 12, 1974, pp. 1298-1304, Washington, DC, US; C. W. Whitehead et al.: "Effect of lipophilic substituents on some biological properties of indoles".

Primary Examiner—David B. Springer
Attorney, Agent, or Firm—Oblon, Spivak, McClelland, Maier & Neustadt

[57] ABSTRACT

A compound of the formula:

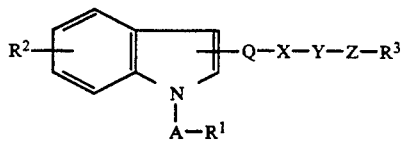

wherein
$R^1$ is carboxy or pharmaceutically acceptable salts and esters thereof;
$R^2$ is hydrogen, lower alkyl or halogen;
$R^3$ is phenyl, naphthyl, phenyl or naphthyl each substituted by from one to three $C_{1-6}$ alkyl groups, mono-, di- or triphenyl ($C_{1-6}$)alkyl; or substituted mono-, di- or triphenyl ($C_{1-6}$) alkyl;
A is lower alkylene which may be substituted by oxo or lower alkenylene,
Q is carbonyl or lower alkylene,
X is

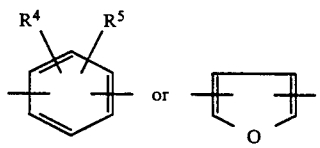

in which
$R^4$ is hydrogen or $C_{1-6}$ alkyl, and
$R^5$ is hydrogen, $C_{1-6}$ alkyl or $Y-Z-R^3$,
Y is a bond or lower alkylene,
Z is lower alkylene

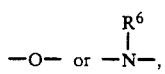

in which $R^6$ is hydrogen, ($C_1-C_6$) alkyl, mono-, di- or triphenyl($C_{1-10}$) alkyl, $C_{1-6}$ alkyl or lower alkoxycarbonyl substituted mono-, di- or triphenyl(-$C_{1-6}$)alkyl or pharmaceutically acceptable carboxylic acid acyl, and pharmaceutically acceptable salts thereof. The compound is useful as a testosterone 5α-reductase inhibitor.

10 Claims, No Drawings

INDOLE DERIVATIVES

CROSS-REFERENCE TO RELATED APPLICATION

This application is a continuation of application Ser. No. 07/792,595, filed Nov. 15, 1991 abandoned, which is a continuation-in-part of application Ser. No. 07/757,522 filed Sep. 11, 1991, now U.S. Pat. No. 5,212,320 which is a continuation-in-part of application Ser. No. 07/702,500 filed May 20, 1991, abandoned.

The present invention relates to novel indole derivatives and a pharmaceutically acceptable salt thereof. More particularly, it relates to novel indole derivatives and a pharmaceutically acceptable salt thereof which have pharmacological activities such as inhibitory activity on testosterone 5α-reductase and the like, to process for preparation thereof, to a pharmaceutical composition comprising the same and to a use of the same as a medicament.

Accordingly, one object of the present invention is to provide novel indole derivatives and a pharmaceutically acceptable salt thereof, which are useful as a testosterone 5α-reductase inhibitor.

Another object of the present invention is to provide process for preparation of said indole derivatives or a salt thereof.

A further object of the present invention is to provide a pharmaceutical composition comprising, as an active ingredient, said indole derivatives or a pharmaceutically acceptable salt thereof.

Still further object of the present invention is to provide a use of said indole derivatives or a pharmaceutically acceptable salt thereof as a medicament such as testosterone 5α-reductase inhibitor useful for treating or preventing testosterone 5α-reductase mediated diseases such as alopecia, acnes, prostatism, and the like in human being or animals.

The indole derivatives of the present invention are novel and can be represented by the formula (I):

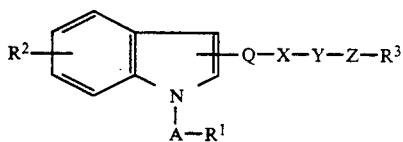

(I)

wherein
$R^1$ is carboxy or protected carboxy,
$R^2$ is hydrogen, lower alkyl or halogen,
$R^3$ is aryl or ar(lower)alkyl, each of which may have suitable substituent(s), or a group of the formula:

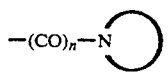

in which

is heterocyclic group containing nitrogen atom, and
n is 0 or 1,

A is lower alkylene which may be substituted by oxo or lower alkenylene,
Q is carbonyl or lower alkylene,

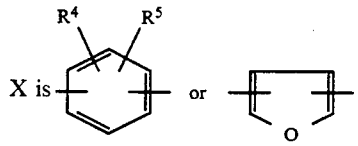

in which
$R^4$ is hydrogen or lower alkyl, and
$R^5$ is hydrogen, lower alkyl or $Y-Z-R^3$,
Y is bond or lower alkylene,
Z is lower alkylene, —O— or

in which $R^6$ is hydrogen, lower alkyl, ar(lower)alkyl which may have suitable substituent(s) or amino protective group.

According to the present invention, the object compound (I) and a salt thereof can be prepared by the following processes.

Process 1

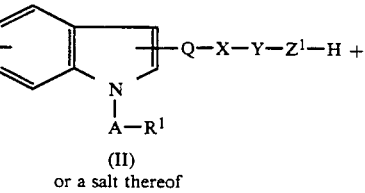

(II)
or a salt thereof $W^1-R_a^3$ ⟶

(III)
or a salt thereof

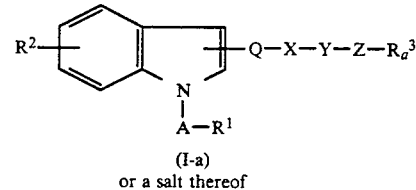

(I-a)
or a salt thereof

Process 2

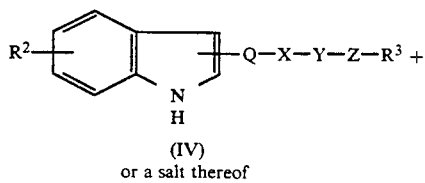

(IV)
or a salt thereof $W^2-A-R^1$ ⟶

(V)
or a salt thereof

3

-continued

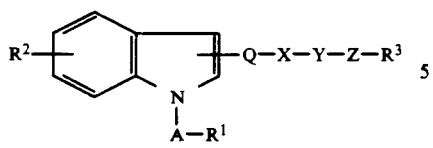

(I)
or a salt thereof
Process 3

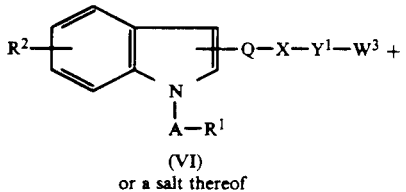

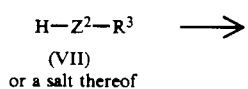

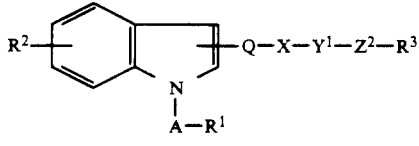

(I-b)
or a salt thereof
Process 4

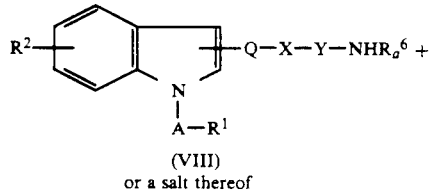

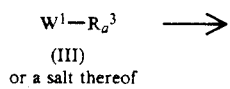

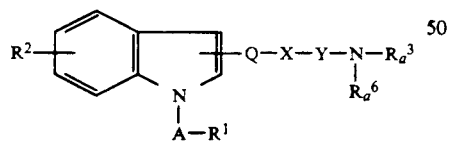

(I-c)
or a salt thereof
Process 5

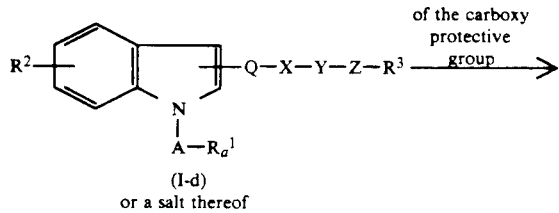

(I-d)
or a salt thereof

4

-continued

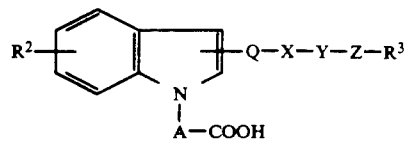

(I-e)
or a salt thereof
Process 6

Elimination of the carboxy protective group →

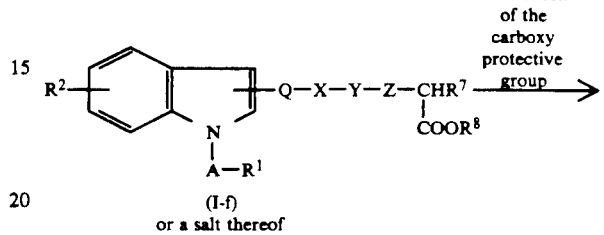

(I-f)
or a salt thereof

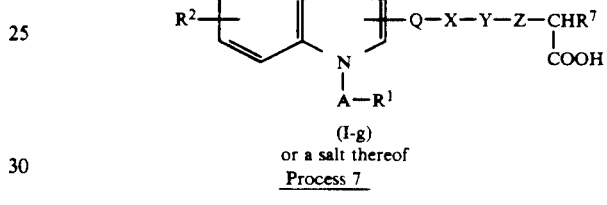

(I-g)
or a salt thereof
Process 7

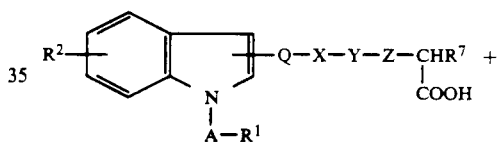

(I-g)
or its reactive derivative
at the carboxy group
or a salt thereof

(IX)
or its reactive
derivative at the
amino group
or a salt thereof

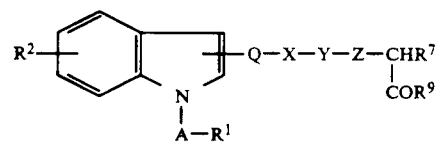

(I-h)
or a salt thereof
Process 8

Elimination of the amino protective group →

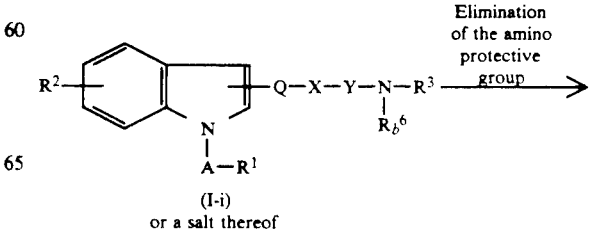

(I-i)
or a salt thereof $$R^2-\underset{\underset{R^1}{\overset{|}{A}}}{\boxed{\text{indole}}}-Q-X-Y-NHR^3$$

(I-j)
or a salt thereof
Process 9

$$R^2-\underset{\underset{R^1}{\overset{|}{A}}}{\boxed{\text{indole}}}-Q-X-Y-NHR^3 +$$

(I-j)
or a salt thereof $$W^4-R_c^6$$

(X)
or a salt thereof $$R^2-\underset{\underset{R^1}{\overset{|}{A}}}{\boxed{\text{indole}}}-Q-X-Y-\underset{\underset{R_c^6}{\overset{|}{N}}}{}-R^3$$

(I-k)
or a salt thereof
Process 10

$$R^2-\underset{\underset{COOH}{\overset{|}{A}}}{\boxed{\text{indole}}}-Q-X-Y-Z-R^3 \xrightarrow{\text{Introduction of the carboxy protective group}}$$

(I-e)
or a salt thereof $$R^2-\underset{\underset{R_a^1}{\overset{|}{A}}}{\boxed{\text{indole}}}-Q-X-Y-Z-R^3$$

(I-d)
or a salt thereof wherein
$R^1$, $R^2$, $R^3$, $R^4$, $R^5$, A, Q, X, Y and Z are each as defined above,
$R_a^1$ is protected carboxy,
$R_a^3$ is ar(lower)alkyl which may have suitable substituent(s) or a group of the formula:

$$-(CO)_n-N\bigcirc$$

in which $$-N\bigcirc$$

and n are each as defined above,
$R_b^6$ is amino protective group;
$R_c^6$ is lower alkyl, ar (lower)alkyl which may have suitable substituent(s) or amino protective group,
$R^7$ is aryl which may have suitable substituent(s),
$R^8$ is carboxy protective group,
$R^9$ is amino which may have suitable substituent(s),
$W^1$, $W^2$, $W^3$ and $W^4$ are each acid residue
$Y^1$ is lower alkylene,
$Z^1$ is —O— or $$\underset{-N-}{\overset{R_a^6}{\overset{|}{}}}$$

in which $R_a^6$ is hydrogen, lower alkyl or amino protective group, and
$Z^2$ is —O— or $$\underset{-N-}{\overset{R^6}{\overset{|}{}}}$$

in which $R^6$ is as defined above.

Suitable salts of the compounds (I) are conventional non-toxic, pharmaceutically acceptable salt and may include a salt with a base or an acid addition salt such as a salt with an inorganic base, for example, an alkali metal salt (e.g. sodium salt, potassium salt, cesium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.), etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); a salt with a basic or acidic amino acid (e.g. arginine, aspartic acid, glutamic acid, etc.); and the like, and the preferable example thereof is an acid addition salt.

With respect to the salt of the compounds (I-a) to (I-k), (II), (III), (IV), (V), (VI), (VII), (VIII), (IX) and (X) in Processes 1 to 10, the suitable examples of the salts of these compounds are to be referred to those as exemplified for the object compound (I).

In the above and subsequent descriptions of the present specification, suitable examples and illustrations of the various definitions which the present invention include within the scope thereof are explained in detail as follows.

The term "lower" is intended to mean 1 to 6 carbon atoms, preferably 1 to 4 carbon atoms, unless otherwise indicated.

Suitable "lower alkyl" may include straight or branched one, having 1 to 6 carbon atom(s), such as methyl ethyl, propyl, isopropyl, butyl, isobutyl, t-butyl, pentyl, hexyl, and the like, preferably one having 1 to 4 carbon atoms.

The term "halogen" means fluoro, chloro, bromo and iodo.

Suitable "lower alkylene" means straight or branched bivalent lower alkane such as methylene, ethylene, trimethylene, tetramethylene, pentamethylene, hexamethylene, propylene, and the like, which may be substituted by oxo.

Suitable "acid residue" may include halogen (e.g. fluoro, chloro, bromo, iodo), acyloxy (e.g. acetoxy, tosyloxy, mesyloxy, etc.) and the like.

Suitable "lower alkenylene" may include one having 2 to 6 carbon atoms such as vinylene, propenylene, and the like.

Suitable "aryl which may have suitable substituent(s)" may include a conventional group such as aryl (e.g. phenyl, naphthyl, etc.), substituted aryl, for example, lower alkylaryl (e.g. tolyl, xylyl, mesityl, cumenyl, isobutylphenyl, etc.), haloaryl (e.g. chlorophenyl, etc.), and the like.

"Ar(lower)alkyl" in the "ar(lower)alkyl which may have suitable substituent(s)" means straight or branched $C_1$-$C_{10}$ alkyl substituted by aryl, and suitable "ar(lower)alkyl which may have suitable substituent(s)" may include a conventional group such as ar(lower)alkyl (e.g. trityl, benzhydryl, benzyl, phenethyl, naphthylmethyl, 1-phenylethyl, 1-phenylpropyl, 1-phenylbutyl, 1-phenylpentyl, 1-phenylhexyl, 1-phenylheptyl, 1-phenyloctyl, 1-phenyldecyl, 2,2-dimethyl-1-phenylpropyl, etc.), substituted ar(lower)alkyl, for example, ar(lower)alkyl substituted by one or more substituents such as lower alkyl as mentioned above, halogen as mentioned above, cyano, carboxy, protected carboxy as mentioned below, aryl which may have suitable substituent(s) as mentioned above, amidated carboxy as mentioned below. Specific examples of thus defined "ar(lower)alkyl which may have suitable substituents" may be methylbenzyl, isobutylbenzyl, methylphenylethyl, isobutylphenylethyl, methylphenylpropyl, isobutylphenylpropyl, methylphenylpentyl, isobutylphenylpentyl, bis(methylphenyl)methyl, bis(propylphenyl)methyl, bis(butylphenyl)methyl, bis(isobutylphenyl)methyl, bis(chlorophenyl)methyl, (cyano)-(isobutylphenyl)methyl, (carboxy)(isobutylphenyl)methyl, (benzyloxycarbonyl)(isobutylphenyl)methyl, (N,N-diethylcarbamoyl)(isobutylphenyl)methyl, (t-butylcarbamoyl)(isobutylphenyl)methyl, (phenylcarbamoyl)(isobutylphenyl)methyl, (isobutylphenylcarbamoyl)(isobutylphenyl)methyl, etc.], and the like.

Suitable "amino protective group" may be a conventional protective group, which is used in the field of organic chemistry, that is, may include acyl such as lower, alkanoyl (e.g. formyl, acetyl, propionyl, butyryl, isobutyryl, valeryl, isovaleryl, pivaloyl, hexanoyl, etc.), lower alkoxycarbonyl (e.g. methoxycarbonyl, ethoxycarbonyl, propoxycarbonyl, butoxycarbonyl, t-butoxycarbonyl, etc.), and the like.

Suitable "protected carboxy" may include an esterified carboxy group.

Suitable examples of the ester moiety of an "esterified carboxy" may be the ones such as lower alkyl ester (e.g. methyl ester, ethyl ester, propyl ester, isopropyl ester, butyl ester, isobutyl ester, tert-butyl ester, pentyl ester, hexyl ester, 1-cyclopropylethyl ester, etc.) which may have at least one suitable substituent(s), for example, lower alkanoyloxy(lower)alkyl ester (e.g. acetoxymethyl ester, propionyloxymethyl ester, butyryloxymethyl ester, valeryloxymethyl ester, pivaloyloxymethyl ester, hexanoyloxymethyl ester, 1(or 2)-acetoxyethyl ester, 1(or 2 or 3)-acetoxypropyl ester, 1(or 2 or 3 or 4)-acetoxybutyl ester, 1(or 2)-propionyloxyethyl ester, 1(or 2 or 3)-propionyloxypropyl ester, 1(or 2)-butyryloxyethyl ester, 1(or 2)-isobutyryloxyethyl ester, 1(or 2)-pivaloyloxyethyl ester, 1(or 2)-hexanoyloxyethyl ester, isobutyryloxymethyl ester, 2-ethylbutyryloxymethyl ester, 3,3-dimethylbutyryloxymethyl ester, 1(or 2)-pentanoyloxyethyl ester, etc.) lower alkanesulfonyl(lower)alkyl ester (e.g. 2-mesylethyl ester, etc.), mono(or di or tri)-halo(lower)alkyl ester (e.g. 2-iodoethyl ester, 2,2,2-trichloroethyl ester, etc.), lower alkoxycarbonyloxy(lower)alkyl ester (e.g. methoxycarbonyloxymethyl ester, ethoxycarbonyloxymethyl ester, 2-methoxycarbonyloxyethyl ester, 1-ethoxycarbonyloxyethyl ester, 1-isopropoxycarbonyloxyethyl ester, etc.), phthalidylidene(lower)alkyl ester, or (5-lower alkyl-2-oxo-1,3-dioxol-4-yl)(lower)alkyl ester (e.g. (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.; lower alkenyl ester (e.g. vinyl ester, allyl ester, etc.); lower alkynyl ester (e.g. ethynyl ester, propynyl ester, etc.); ar(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc.); aryl ester which may have at least one suitable substituent(s) (e.g. phenyl ester, 4-chlorophenyl ester, tolyl ester, tert-butylphenyl ester, xylyl ester, mesityl ester, cumenyl ester, etc.); phthalidyl ester; and the like.

Preferable examples of the esterified carboxy as mentioned above may include lower alkoxycarbonyl (e.g. methoxycarbonyl, ethoxycarbonyl, propoxycarbonyl, isopropoxycarbonyl butoxycarbonyl, isobutoxycarbonyl, tert-butoxycarbonyl, pentyloxycarbonyl, tert-pentyloxycarbonyl, hexyloxycarbonyl, 1-cyclopropylethoxycarbonyl, etc.).

Suitable "carboxy protective group" may be the ester moiety of the above defined "protected carboxy" and may include lower alkyl (e.g. methyl, ethyl, etc.), ar(lower)alkyl (e.g. benzyl, etc.), and the like.

Suitable "amino which may have suitable substituent(s)" is conventional one used in a pharmaceutical field and may include amino, mono or di(lower)alkylamino (e.g. methylamino, dimethylamino, ethylamino, diethylamino, butylamino, t-butylamino, etc.), arylamino (e.g. phenylamino, etc.), lower alkylarylamino (e.g. isobutylphenylamino, etc.), and the like.

Suitable "heterocyclic group containing nitrogen atom" may include saturated or unsaturated monocyclic or polycyclic heterocyclic group containing at least one nitrogen atom. Especially preferable heterocyclic group may be 5- or 6- membered aliphatic heteromonocyclic group (e.g. morpholinyl, pyrrolidinyl, imidazolidinyl, piperidyl, piperazinyl, etc.), unsaturated condensed heterocyclic group such as dibenzo[6 or 7-membered unsaturated]heteromonocyclic group (e.g. phenoxazinyl, phenothiazinyl, 10,11-dihydro-5H-dibenzoazepinyl, etc.), and the like.

Suitable "amidated carboxy" may carbamoyl which may have suitable substituent(s) and may include carbamoyl, mono or di(lower)alkylcarbamoyl (e.g. methylcarbamoyl, dimethylcarbamoyl, ethylcarbamoyl diethylcarbamoyl, butylcarbamoyl, t-butylcarbamoyl, etc.), lower alkylarylcarbamoyl (e.g. isobutylphenylcarbamoyl, etc.), and the like.

Particularly, the preferred embodiments of $R^1$, $R^2$, $R^3$, A, Q, X, Y and Z are as follows. $R^1$ is carboxy; lower alkoxycarbonyl, more preferably $C_1$-$C_4$ alkoxycarbonyl (e.g. methoxycarbonyl, ethoxycarbonyl, etc.); or ar(lower)alkoxycarbonyl, more preferably mono- or di- or triphenyl($C_1$-$C_4$)alkoxycarbonyl (e.g. benzyloxycarbonyl, etc.), $R^2$ is hydrogen;

lower alkyl, more preferably $C_1$-$C_4$ alkyl (e.g. methyl, etc.); or halogen (e.g. chloro, etc.), $R^3$ is aryl which may be substituted by lower alkyl, more preferably phenyl substituted by $C_1$-$C_4$ alkyl (e.g. isobutylphenyl, etc.);

ar(lower)alkyl which may be substituted by one to three substituents selected from the group consisting of lower alkyl, halogen, cyano, carboxy, protected carboxy, and amidated carboxy, more preferably mono- or di- or triphenyl(lower)alkyl which may be substituted by one or two the groups selected from lower alkyl, halogen, cyano, carboxy, phenyl(lower)-alkoxycarbonyl, mono or di(lower)alkylcarbamoyl, phenylcarbamoyl and lower alkylphenylcarbamoyl, most preferably mono- or di- or triphenyl($C_1$-$C_6$)alkyl which may be substituted by the group selected from ($C_1$-$C_4$)alkyl, halogen, cyano, carboxy, phenyl($C_1$-$C_4$)alkoxycarbonyl, mono or di($C_1$-$C_4$)alkylcarbamoyl, phenylcarbamoyl and ($C_1$-$C_4$)alkylphenylcarbamoyl (e.g. benzyl, isobutylbenzyl, isobutylphenylethyl, isobutylphenylpropyl, isobutylphenylpentyl, bis(isobutylphenyl)methyl, bis(chlorophenyl)methyl, (cyano)(isobutylphenyl)methyl, (carboxy)(isobutylphenyl)methyl, (benzyloxycarbonyl)(isobutylphenyl)methyl, (N,N-diethylcarbamoyl)(isobutylphenyl)methyl, (t-butylcarbamoyl)(isobutylphenyl)methyl, (phenylcarbamoyl)(isobutylphenyl)methyl, (isobutylphenylcarbamoyl)(isobutylphenyl)methyl, etc.);

5- or 6- membered aliphatic heteromonocycliccarbonyl (e.g. piperidylcarbonyl, etc.); or unsaturated condensed heterocyclic group (e.g. phenoxazinyl, phenothiazinyl, 10,11-dihydro-5H-dibenzo[b,f]azepinyl, etc.), A is lower alkylene which may be substituted by oxo, more preferably $C_1$-$C_4$ alkylene which may be substituted by oxo (e.g. ethylene, trimethylene, oxotrimethylene, etc.); or lower alkenylene, more preferably $C_2$-$C_4$ alkenylene (e.g. propenylene, etc.), Q is carbonyl; or lower alkylene, more preferably $C_1$-$C_4$ alkylene (e.g. methylene, etc.), X is

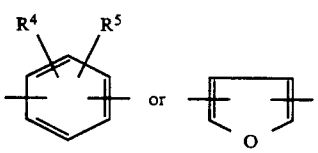

in which $R^4$ is hydrogen; or lower alkyl, more preferably $C_1$-$C_4$ alkyl (e.g. methyl, etc.) , $R^5$ is hydrogen; lower alkyl, more preferably $C_1$-$C_4$ alkyl (e.g. methyl, etc.); or ar(lower)alkylamino which may be substituted by the group(s) selected from lower alkyl or lower alkoxycarbonyl, more preferably $C_1$-$C_4$ alkylbenzylamino or N-$C_1$-$C_4$ alkoxycarbonyl-N-$C_1$-$C_4$ alkylbenzylamino (e.g. isobutylbenzylamino, N-t-butoxycarbonyl-N-isobutylbenzylamino, etc.), Y is bond; or lower alkylene, more preferably $C_1$-$C_4$ alkylene (e.g. methylene, etc.), and Z is lower alkylene, more preferably $C_1$-$C_4$ alkylene (e.g. methylene, etc.);

O; or

N-$R^6$ in which $R^6$ is hydrogen; lower alkyl, preferably $C_1$-$C_4$ alkyl (e.g. methyl, ethyl, etc.); lower alkoxycarbonyl, preferably $C_1$-$C_4$alkoxycarbonyl (e.g. t-butoxycarbonyl, etc.);

ar(lower)alkyl which may be substituted by lower alkyl, more preferably mono- or di- or triphenyl(lower)alkyl which may be substituted by lower alkyl, most preferably mono- or di- or triphenyl($C_1$-$C_6$)alkyl which may be substituted by $C_1$-$C_4$ alkyl (e.g. benzyl, isobutylbenzyl, etc.).

Also, the preferred embodiments of $R^1$, $R^2$, $R^3$, A, Q, X, Y and Z are as follows.

$R^1$ is carboxy, or protected carboxy such as esterified carboxy, for example, lower alkoxycarbonyl;

$R^2$ is hydrogen, lower alkyl or halogen;

$R^3$ is a group of the formula:

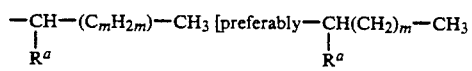

more preferably

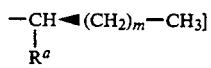

in which $R^a$ is aryl which may have suitable substituent(s) as explained above [preferably phenyl which may have suitable substituent(s), more preferably lower alkylphenyl] and m is an integer of 1 to 6;

A is lower alkylene;

Q is carbonyl;

X is phenylene;

Y is bond; and

Z is —O— or —NH—.

The processes 1 to 10 for preparing the object compound (I) of the present invention are explained in detail in the following.

PROCESS 1

The object compound (I-a) or a salt thereof can be prepared by reacting the compound (II) or a salt thereof with the compound (III) or a salt thereof.

This reaction is usually carried out in a solvent such as alcohol [e.g. methanol, ethanol, etc.], dichloromethane, benzene, N,N-dimethylformaraide, tetrahydrofuran, diethyl ether or any other solvent which does not adversely affect the reaction.

The reaction may be carried out in the presence of an inorganic or an organic base such as an alkali metal hydroxide [e.g. sodium hydroxide, potassium hydroxide, etc.], an alkali metal carbonate [e.g. sodium carbonate, potassium carbonate, etc.], an alkali metal bicarbonate [e.g. sodium bicarbonate, potassium bicarbonate, etc.], alkali metal hydride (e.g. sodium hydride, potassium hydride, etc.), tri(lower)alkylamine [e.g. trimethylamine, triethylamine, diisopropylethylamine, etc.], pyridine or its derivative [e.g. picoline, lutidine, 4-dimethylaminopyridine, etc.], or the like. In case that the base to be used is liquid, it can also be used as a solvent.

The reaction temperature is not critical, and the reaction can be carried out under cooling, at room temperature or under warming or heating.

PROCESS 2

The object compound (I) or a salt thereof can be prepared by reacting the compound (IV) or a salt thereof with the compound (V) or a. salt thereof.

This reaction can be carried out in substantially the same manner as Process 1, and therefore the reaction mode and reaction conditions [e.g. solvents, reaction temperature, etc.] of this reaction are to be referred to those as explained in Process 1.

PROCESS 3

The object compound (I-b) or a salt thereof can be prepared by reacting the compound (VI) or a salt thereof with the compound (VII) or a salt thereof.

This reaction can be carried out in substantially the same manner as Process 1, and therefore the reaction mode and reaction conditions [e.g. solvents, reaction temperature, etc.] of this reaction are to be referred to those as explained in Process 1.

PROCESS 4

The object compound (I-c) or a salt thereof can be prepared by reacting the compound (VII) or a salt thereof with the compound (III) or a salt thereof.

This reaction can be carried out in substantially the same manner as Process 1, and therefore the reaction mode and reaction conditions [e.g. solvents, reaction temperature, etc.] of this reaction are to be referred to those as explained in Process 1.

The present reaction includes, within its scope, the case that when $R^1$ is carboxy, it is protected during the reaction or at the post-treating step of the present process.

PROCESS 5

The object compound (I-e) or a salt thereof can be prepared by subjecting the compound (I-d) or a salt thereof to elimination reaction of the carboxy protective group.

In the present elimination reaction, all conventional methods used in the elimination reaction of the carboxy protective group, for example, hydrolysis, reduction, elimination using Lewis acid, etc. are applicable. When the carboxy protective group is an ester, it can be eliminated by hydrolysis or elimination using Lewis acid. The hydrolysis is preferably carried out in the presence of a base or an acid.

Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4.3.0]non-5-one, 1,4-diazabicyclo[2.2.2]octane, 1,5-diazabicycloE5.4.0]undecene-5 or the like. The hydrolysis using a base is often carried out in water or a hydrophilic organic solvent or a mixed solvent thereof.

Suitable acid may include an organic acid (e.g. formic acid, acetic acid, propionic acid, etc.) and an inorganic acid (e.g. hydrochloric acid, hydrobromic acid, sulfuric acid, etc.).

The present hydrolysis is usually carried out in an organic solvent, water or a mixed solvent thereof.

The reaction temperature is not critical, and it may suitable be selected in accordance with the kind of the carboxy protective group and the elimination method.

The elimination using Lewis acid is preferable to eliminate substituted or unsubstituted ar(lower)alkyl ester and carried out by reacting the compound (Ig) or a salt thereof with Lewis acid such as boron trihalide (e.g. boron trichloride, boron trifluoride, etc.), titanium tetrahalide (e.g. titanium tetrachloride, titanium tetrabromide, etc.), tin tetrahalide (e.g. tin tetrachloride, tin tetrabromide, etc.), aluminum halide (e.g. aluminum chloride, aluminum bromide, etc.), trihaloacetic acid (e.g. trichloroacetic acid, trifluoroacetic acid, etc.) or the like. This elimination reaction is preferably carried out in the presence of cation trapping agents (e.g. anisole, phenol, etc.) and is usually carried out in a solvent such as nitroalkane (e.g. nitromethane, nitroethane, etc.), alkylene halide (e.g. methylene chloride, ethylene chloride, etc.), diethyl ether, carbon disulfide or any other solvent which does not adversely affect the reaction. These solvents may be used as a mixture thereof.

The reduction elimination can be applied preferably for elimination of the protective group such as halo(lower)alkyl (e.g. 2-iodoethyl, 2,2,2-trichloroethyl, etc.) ester, ar(lower)alkyl (e.g. benzyl, etc.) ester or the like.

The reduction method applicable for the elimination reaction may include, for example, reduction by using a combination of a metal (e.g. zinc, zinc amalgam, etc.) or a salt of chromium compound (e.g. chromous chloride, chromous acetate, etc.) and an organic or an inorganic acid (e.g. acetic acid, propionic acid, hydrochloric acid, etc.); and conventional catalytic reduction in the pressure of a conventional metallic catalyst (e.g. palladium carbon, Raney nickel, etc.).

The reaction temperature is not critical, and the reaction is usually carried out under cooling, at ambient temperature or under warming.

PROCESS 6

The object compound (I-g) or a salt thereof can be prepared by subjecting the compound (I-f) or a salt thereof to elimination reaction of the carboxy protective group.

This reaction can be carried out in substantially the same manner as Process 5, and therefore the reaction mode and reaction conditions [e.g. bases, acids, reducing agents, catalysts, solvents, reaction temperature, etc.] of this reaction are to be referred to those as explained in Process 5.

PROCESS 7

The object compound (I-h) or a salt thereof, can be prepared by reacting a compound (I-g) or its reactive derivative at the carboxy group or a salt thereof with a compound (IX) or its reactive derivative at the amino group or a salt thereof.

Suitable reactive derivative at the amino group of the compound (IX) may include Schiff's base type imino or its tautomeric enamine type isomer formed by the reaction of the compound (IX) wit a carbonyl compound such as aidehyde, ketone or the like; a silyl derivative formed by the reaction of the compound (IX) with a silyl compound such as bis(trimethylsilyl)acetamide, mono(trimethylsilyl)acetamide, bis(trimethylsilyl)urea or the like; a derivative formed by reaction of the compound (IX) with phosphorus trichloride or phosgene, and the like.

Suitable reactive derivative at the carboxy group of the compound (I-g) may include an acid halide, an acid anhydride, an activated amide, an activated ester, and the like. Suitable examples of the reactive derivatives may be an acid chloride; an acid azide; a mixed acid anhydride within acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminomethyl $[(CH_3)_2N^+=CH-]$ ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (I-g) to be used.

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformarnide, pyridine or any other organic solvent which does not adversely influence the reaction. These conventional solvent may also be used in a mixture with water.

In this reaction, when the compound (I-g) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; diphenyl phosphorylazide; thionyl chloride; oxalyl chloride; lower alkyl haloformate [e.g. ethyl chloroformate, isopropyl chloroformate, etc.]; triphenylphosphine; 2-ethyl-7-hydroxybenzisoxazoliurn salt; 2-ethyl-5-(m-sulfophenyl)isoxazolium hydroxide intramolecular salt; 1-(p-chlorobenzenesulfonyloxy)-6-chloro-1H-benzotriazole; so-called viismeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling to warming.

PROCESS 8

The object compound (I-j) or a salt thereof can be prepared by subjecting the compound (I-i) or a salt thereof to elimination reaction of the amino protective group.

This reaction can be carried out in substantially the same manner as Process 5, and therefore the reaction mode and reaction conditions [e.g. bases, acids, reducing agents, catalysts, solvents, reaction temperature, etc]of this reaction are to be referred to those as explained in Process 5.

PROCESS 9

The object compound (I-k) or a salt thereof can be prepared by reacting the compound (I-j) or a salt thereof with the compound (X) or a salt thereof.

This reaction can be carried out in substantially the same manner as Process 1, and therefore the reaction mode and reaction conditions [e.g. solvents, reaction temperature, etc.] of this reaction are to be referred to those as explained. in Process 1.

The present reaction includes, within its scope, the case that when $R^1$ is carboxy, it is protected. during the reaction or at the post-treating step of the present process.

PROCESS 10

The object compound (I-d) or a salt thereof can be prepared by subjecting the compound (I-e) or a salt thereof to introduction reaction of the carboxy protective group.

The reaction can be carried out in substantially the same manner as Process 1, and therefore the reaction mode and reaction conditions [e.g. solvents, reaction temperature, etc.] of this reaction are to be referred to those as explained in Process 1.

Some of the starting compounds (II), (III), (IV) and (VI) are new and can be prepared by the following methods or conventional manners, the details of which are shown in Preparations mentioned below, or a conventional manner.

Method A-(1)

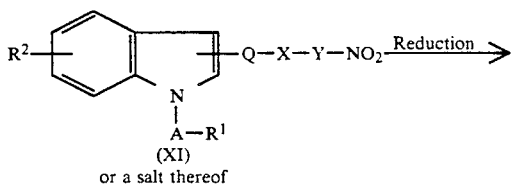

or a salt thereof

-continued

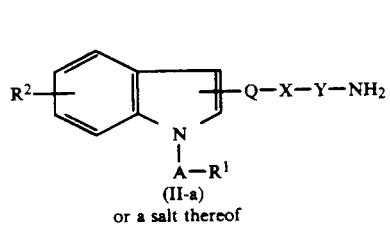
(II-a)
or a salt thereof

Method A-(2)

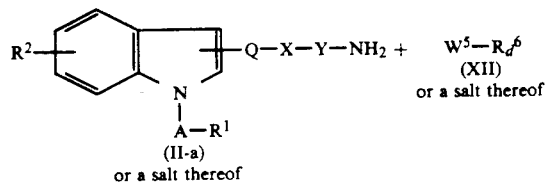
(II-a)
or a salt thereof

+ W⁵—R_d⁶
(XII)
or a salt thereof

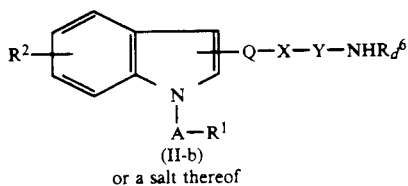
(II-b)
or a salt thereof

Method A-(3)

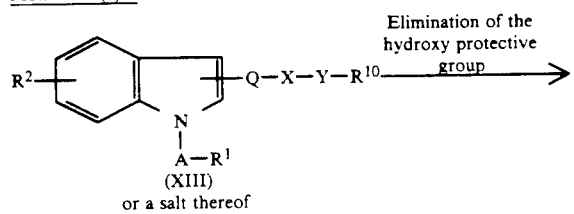
(XIII)
or a salt thereof

Elimination of the hydroxy protective group →

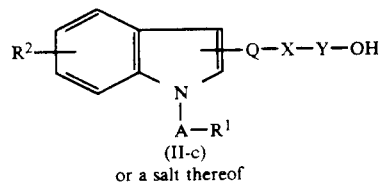
(II-c)
or a salt thereof

Method A-(4)

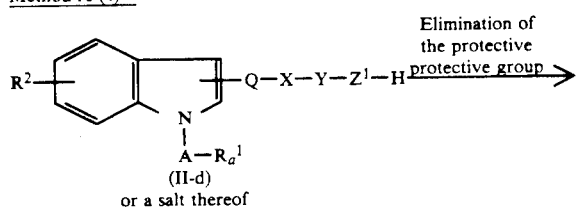
(II-d)
or a salt thereof

Elimination of the protective group →

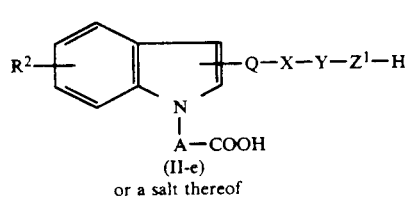
(II-e)
or a salt thereof

Method B-(1)

-continued

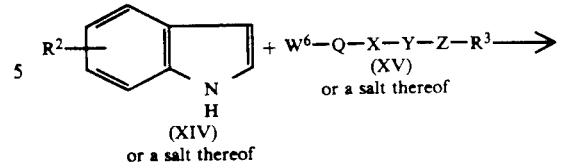
+ W⁶—Q—X—Y—Z—R³
(XV)
or a salt thereof

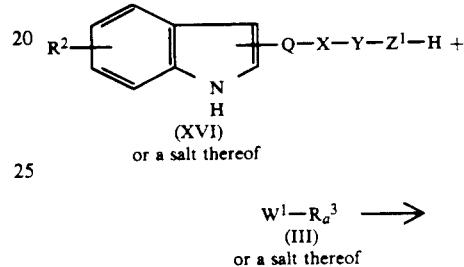
(IV)
or a salt thereof

Method B-(2)

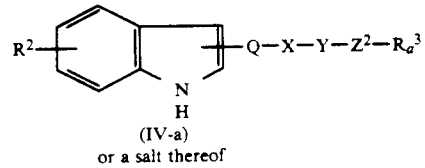
(XVI)
or a salt thereof

W¹—R_a³ →
(III)
or a salt thereof

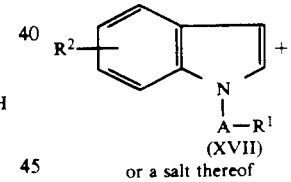
(IV-a)
or a salt thereof

Method C

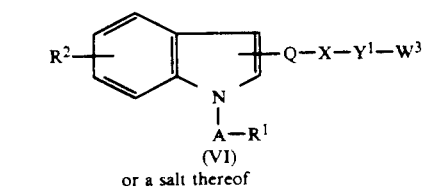
(XVII)
or a salt thereof

W⁶—Q—X—Y¹—W³ →
(XVIII)
or a salt thereof

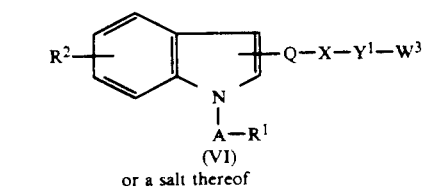
(VI)
or a salt thereof wherein
$R^1$, $R_a^1$, $R^2$, $R^3$, $R_a^3$, $R_d^6$, A, Q, X, Y, $Y^1$, $Z^1$, $Z^2$, $W^1$ and $W^3$ are each as defined above,
$R^{10}$ is protected hydroxy, and
$W^5$ and $W^6$ are each acid residue.

Methods A, B and C can be carried out in a conventional manner.

The object compound (I) of the present invention can be isolated and purified in a conventional manner, for example, extraction, precipitation, fractional crystallization, recrystallization, chromatography, and the like.

The object compound (I) thus obtained can be converted to its salt by a conventional method.

The object compound (I) of the present invention is useful as a testosterone 5α-reductase inhibitor and effective to testosterone 5α-reductase mediated diseases such as prostatism, prostatic hypertrophy, prostatic cancer, alopecia, hirsutism (e.g. female hirsutism, etc.), androgenic alopecia (or male-pattern baldness), acne (e.g. acne vulgaris, pimple etc.), other hyperandrogenism, and the like.

In order to illustrate the usefulness of the object compounds (I), pharmacological activity of representative compounds of the present invention is shown below.

[1]Test Compound (1) 4-[3-[3-[Bis(4-isobutylphenyl)methylamino]benzoyl]indol-1-yl]butyric acid
(2) 4-[3-[3-[Bis(4-isobutylphenyl)methylamino]benzoyl]-2-methylindol-1-yl]butyric acid
(3) 4-[3-[4-[Bis(4-isobutylphenyl)methoxy]benzoyl]indol-1-yl]butyric acid
(4) 4-[3-[4-[1-(4-Isobutylphenyl)ethoxy]benzoyl]indol-1-yl]butyric acid
(5) 4-[3-[3-[2,2-Bis(4-isobutylphenyl)ethyl]]benzoyl]indol-1-yl]butyric acid
(6) 4-[3-[3-(10,11-Dihydro-5H-dibenz[b,f]azepin-5-ylmethyl)benzoyl]indol-1-yl]butyric acid
(7) 4-[3-[3,5-Bis[(4-isobutylbenzyl)amino]benzoyl]indol-1-yl]butyric acid dihydrochloride
(8) 4-[3-[4-1-(4-Isobutylphenyl)pentyloxy]benzoyl]indol-1-yl]butyric acid

[2]Inhibitory activity on testosterone 5α-reductase in rats

Test Methods i) Materials 1,2,6,7-$^3$H-Testosterone (85-105 Ci/mmol):

1,2,6,7-$^3$H-Testosterone (85-105 Ci/mmol) is a mixture of 1,2,6,7-$^3$H-testosterone and testosterone which includes 85-105 Ci of 1,2,6,7-$^3$H-testosterone per mmol of testosterone and is purchased from New England Nuclear, Boston, Mass., U.S.A..

Aquazol-2 (Aquazol-2 Universal LSC Cocktail): trademark, purchased from New England Nuclear, Boston, Mass., U.S.A.

ii) Preparation of prostatic testosterone 5α-reductase

Mature Spraque-Dawley male rats (7-8 weeks old) were sacrificed by diethyl ether. The ventral prostates were dissected to be free of their capsules and their combined volume was measured by displacement in several milliliters of ice-cold medium A (0.32M sucrose, 0.1 mM dithiothreitol and 20 mM sodium phosphate, pH 6.5). Unless specified, all the following procedures were carried out at 0°-4° C. The prostates were drained, minced, and then homogenized in 3-4 tissue volumes of medium A with Pyrex-glass homogenizer. The homogenate was fractioned by differential centrifugations at 3,000 g for 15 minutes. The resulting pellets were resuspended in medium A. The suspension (20-30 mg protein/ml) was stored at −80° C.

iii) Testosterone 5α-reductase assay

The reaction solution contains 1 mM dithiothreitol, 40 mM sodium phosphate pH 6.5, 50 μM NADPH, 1,2,6,7-$^3$H-testosterone/testosterone (2.2×10$^{-9}$M) and the suspension prepared above (0.8 mg of protein) in a total volume of 565 μl. Test Compound was added in 10 μl of 10% ethanol whereas control tubes received the same volume of 10% ethanol. The reaction was started with the addition of the enzyme suspension. After incubation at 37° C. for 30 minutes, the reaction was extracted with 1 ml of ethyl acetate. Fifty μl of ethyl acetate phase was chromatographed on a Merck silica plastic sheet Kieselgel 60 F$_{254}$, using ethyl acetate:

cyclohexane (1:1) as the developing solvent system. The plastic sheet was air dried and cut the testosterone and the 5α-dihydrotestosterone areas. The radioactivity was counted in 5 ml of Aquazol-2 in Packard scintillation counter (PACKARD TRI - CARB 4530), and an inhibitory ratio was calculated.

Test Results

| Compound | IC$_{50}$ (M) |
|---|---|
| (1) | $5.5 \times 10^{-9}$ |
| (2) | $8.6 \times 10^{-9}$ |
| (3) | $3.5 \times 10^{-9}$ |
| (4) | $3.1 \times 10^{-9}$ |
| (5) | $7.4 \times 10^{-9}$ |
| (6) | $9.3 \times 10^{-10}$ |
| (7) | $3.7 \times 10^{-9}$ |
| (8) | $6.6 \times 10^{-10}$ |

For therapeutic or preventive administration, the object compound (I) of the present invention are used in the form of conventional pharmaceutical preparation which contains said compound as an active ingredient, in admixture with pharmaceutically acceptable carriers such as an organic or inorganic solid or liquid excipient which is suitable for oral, parenteral and external administration. The pharmaceutical preparation may be in solid form such as tablet, granule, powder, capsule, or liquid form such as solution, suspension, syrup, emulsion, lemonade, lotion and the like.

If needed, there may be included in the above preparations auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the compound (I) may vary from and also depend upon the age, conditions of the patient, a kind of diseases or conditions, a kind of the compound (I) to be applied, etc. In general amounts between 0.01 mg and about 500 mg or even more per day may be administered to a patient. An average single dose of about 0.05 mg, 0.1 mg, 0.25 mg, 0.5 mg, 1 mg, 20 mg, 50 mg, 100 mg of the object compound (I) of the present invention may be used in treating diseases.

The following Preparations and Examples are given for the purpose of illustrating the present invention.

PREPARATION 1

A solution of 3-nitrobenzoyl chloride (4.76 g) in dichloromethane (20 ml) was added to a suspension of aluminum chloride (3.42 g) in dichloromethane (50 ml) at 25° C., and the mixture was stirred at the same temperature for an hour. A solution of indole (3.0 g) in dichloromethane (20 ml) was added to the mixture at 25° C. After stirring for an hour at 25° C., the reaction mixture was poured into a mixture of ethyl acetate and ice water. The organic layer was separated, washed with water, and dried over magnesium sulfate. After evaporation of solvent, the crystalline residue was recrystallized from ethyl acetate to give 3-(3-nitrobenzoyl)indole (2.37 g) as pale red crystals. The mother liquid was purified by column chromatography on silica gel (20 g) with chloroform as eluent to give another crystals of 3-(3-nitrobenzoyl)indole (0.277 g).

NMR (CDCl$_3$-CD$_3$OD, $\delta$): 7.21-7.35 (2H, m), 7.42-7.55 (1H, m), 7.68-7.79 (2H, m), 8.13 (1H, dif-dd, J=7.5 Hz), 8.24-8.35 (1H, m), 8.40 (1H, dif-dd, J=7.5 Hz), 8.60 (1H, dif-d)

PREPARATION 2

A mixture of 3-(3-nitrobenzoyl)indole (2.09 g), ethyl 4-bromobutyrate (1.614 g) and potassium carbonate (3.118 g) in N,N-dimethylformamide (20 ml) was stirred at 25° C. overnight. The reaction mixture was poured into a mixture of ethyl acetate and 1N hydrochloric acid. The organic layer was separated, washed with water and brine, and dried over magnesium sulfate. After evaporation of solvent, the crystalline residue was recrystallized from a mixture of ethyl acetate and hexane to give ethyl 4-[3-(3-nitrobenzoyl)indol-1-yl]butyrate (2.71 g) as colorless crystals.

NMR (CDCl$_3$, $\delta$): 1.20 (3H, t, J=7.5 Hz), 2.12-2.40 (4H, m), 4.10 (2H, q, J=7.5 Hz), 4.30 (2H, t, J=7.5 Hz), 7.30-7.50 (3H, m), 7.58 (1H, s), 7.70 (1H, t, J=5 Hz), 8.27 (1H, dif-dd, J=7.5 Hz), 8.35-8.48 (2H, m), 8.68 (1H, dif-d)

PREPARATION 3

A mixture of ethyl 4-[3-(3-nitrobenzoyl)indol-1-yl]butyrate (1.60 g), 1N aqueous sodium hydroxide (11 ml) and 1,4-dioxane (50 ml) was stirred at 25° C. for 14 hours. After evaporation of the organic solvent, 1N hydrochloric acid (20 ml) was added to the aqueous solution and the mixture was extracted with ethyl acetate. The extract was washed with water, dried over magnesium sulfate, and evaporated in vacuo. The crystalline residue was recrystallized from a mixture of ethyl acetate and hexane to give 4-[3-(3-nitrobenzoyl)indol-1-yl]butyric acid (1.28 g) as colorless crystals.

NMR (CDCl$_3$-CD$_3$OD, $\delta$): 2.10 (2H, m), 2.35 (2H, t, J=7.5 Hz), 4.30 (2H, t, J=7.5 Hz), 7.30-7.55 (3H, m), 7.60 (1H, s), 7.72 (1H, t, J=7.5 Hz), 8.16 (1H, dif-dd, J=7.5 Hz), 8.31-8.48 (2H, m), 8.65 (1H, dif-d)

PREPARATION 4

A mixture of 4-[3-(3-nitrobenzoyl)indol-1-yl]butyric acid (1.20 g), 10% palladium on carbon (300 mg), methanol (12 ml) and 1,4-dioxane (12 ml) was stirred under hydrogen atmosphere (3 atm) at 25° C. for 45 minutes. The mixture was filtered and the filtrate was evaporated to give 4-[3-(3-aminobenzoyl)indol-1-yl]butyric acid (982 mg) as yellow oil.

NMR (CDCl$_3 \propto$ CH$_3$OD, $\delta$): 2.15-2.45 (4H, m), 4.32 (2H, t, J=7.5 Hz), 6.97 (1H, m), 7.15-7.60 (6H, m), 7.72 (1H, s), 8.45 (1H, m)

PREPARATION 5

The following compound was obtained according to a similar manner to that of Preparation 1.

3-(4-Nitrobenzoyl)indole

NMR (CDCl$_3$-CD$_3$OD, $\delta$): 7.2-7.45 (2H, m), 7.5-7.6 (2H, m), 7.72 (2H, d, J=7.5 Hz), 8.2-8.3 (1H, m), 8.31 (2H, d, J=7.5 Hz)

PREPARATION 6

The following compound was obtained according to a similar manner to that of Preparation 2.

Ethyl 4-[3-(4-nitrobenzoyl)indol-1-yl]butyrate

NMR (CDCl$_3$, $\delta$): 1.20 (3H, t, J=7.5 Hz), 2.2-2.4 (4H, m), 4.10 (2H, q, J=7.5 Hz), 4.27 (2H, t, J=7.5 Hz), 7.35-7.5 (3H, m), 7.52 (1H, s), 7.95 (2H, d, J=8 Hz), 8.35 (2H, d, J=8 Hz), 8.4-8.5 (1H, m)

PREPARATION 7

The following compound was obtained according to a similar manner to that of Preparation 3.

4-[3-(4-Nitrobenzoyl)indol-1-yl]butyric acid

NMR (CDCl$_3$-CD$_3$OD, $\delta$): 1.8-2.0 (2H, m), 2.15 (2H, t, J=7.5 Hz), 4.12 (2H, t, J=7.5 Hz), 7.1-7.25 (2H, m), 7.45-7.55 (1H, m), 7.81 (1H, s), 7.85 (2H, d, J=8 Hz), 8.10-8.15 (1H, m), 8.18 (2H, d, J=8 Hz)

PREPARATION 8

The following compound was obtained according to a similar manner to that of Preparation 4.

4-[3-(4-Aminobenzoyl)indol-1-yl]butyric acid

NMR (CDCl$_3$-CD$_3$OD, $\delta$) : 2.20 (2H, quintet, J=7.5 Hz), 2.33 (2H, t, J=7.5 Hz), 4.36 (2H, t, J=7.5 Hz), 6.75 (2H, d, J=8 Hz), 7.20-7.40 (2H, m), 7.50 (1H, dd, J=2, 8 Hz), 7.65-7.80 (1H, m), 7.70 (2H, d, J=8 Hz), 8.25 (1H, dd, J=2, 8 Hz)

PREPARATION 9

To a suspension of isopropyltriphenylphosphonium iodide (24.7 g) in tetrahydrofuran (100 ml) was added a solution of potassium tert-butoxide (7.71 g) in tetrahydrofuran (50 ml) at 25° C. over 20 minutes, and the mixture was stirred for 30 minutes at the same temperature. A solution of 3-cyanobenzaldehyde (5.0 g) in tetrahydrofuran (50 ml) was added at 0° C. over 20 minutes, and the mixture was stirred at 25° C. for 1 hour. The mixture was poured into a mixture of ethyl acetate and 1N hydrochloric acid. The organic layer was separated, washed with water and brine, and dried over magnesium sulfate. The residue was chromatographed on silica gel (200 g) eluting with 10% ethyl acetate in hexane to give 3-(2-methyl-1-propenyl)benzonitrile (4.21 g) as a pale yellow oil.

NMR (CDCl$_3$, $\delta$): 1.83 (3H, d, J=1.5 Hz), 1.91 (3H, d, J=1.5 Hz), 6.22 (1H, s), 7.31-7.56 (4H, m)

PREPARATION 10

The following compound was obtained according to a similar manner to that of Preparation 9.

1-(2-Methyl-1-propenyl)-3-nitrobenzene

NMR (CDCl$_3$, $\delta$): 1.88 (3H, d, J=1.5 Hz), 1.93 (3H, d, J=1.5 Hz), 6.30 (1H, S), 7.49-7.60 (2H, m), 7.95-8.13 (2H, m)

PREPARATION 11

To a solution of 3-(2-methyl-1-propenyl)benzonitrile (5.80 g) in methanol (50 ml) was added 10% palladium on activated carbon (1 g), and the mixture was stirred under hydrogen atmosphere (3 atm) at 25° C. for 1 hour. The catalyst was filtered off and the liltrate was evaporated to give 3-isobutylbenzonitrile (5.52 g) as a pale yellow oil.

NMR (CDCl₃, δ): 0.90 (6H, d, J=7.5 Hz), 1.70–1.98 (1H, m), 2.50 (2H, d, J=7.5 Hz), 7.31–7.60 (4H, m)

PREPARATION 12

To a solution of 3-isobutylbenzonitrile (7.0 g) in toluene (150 ml) was added a 1.5M solution of diisobutylaluminum hydride in toluene (88 ml) at 25° C. over 30 minutes and the mixture was stirred at 25° C. for 2 hours. Another 1.5M solution of diisobutylaluminum hydride in toluene (30 ml) was added, and the mixture was stirred at 25° C. for 1 hour. The mixture was poured into a mixture of ether, aqueous ammonium chloride and 1N hydrochloric acid. The organic layer was separated, washed with water and brine, and dried over magnesium sulfate. After evaporation of the solvent, the residue was chromatographed on silica gel (150 g) eluting with a mixture of toluene and hexane (2:1) to give 3-isobutylbenzaldehyde (4.72 g) as a colorless oil.

NMR (CDCl₃, δ): 0.90 (6H, d, J=7.5 Hz), 1.80–2.05 (1H, m), 2.58 (2H, d, J=7.5 Hz), 7.35–7.50 (2H, m), 7.60–7.79 (2H, m), 10.00 (1H, s)

PREPARATION 13

To a solution of 1-(2-methyl-l-propenyl)-3-nitrobenzene (4.57 g) in a mixture of methanol (50 ml) and 6N hydrochloric acid (14 ml) was added 10% palladium on activated carbon (1 g), and the mixture was stirred under hydrogen atmosphere (3 atm) at 25° C. for 3 hours. The catalyst was filtered off, and the filtrate was evaporated. The residue was poured into a mixture of ethyl acetate and aqueous sodium bicarbonate. The organic layer was separated, washed with water and brine, and dried over magnesium sulfate. Evaporation of the solvent gave 3-isobutylphenylamine (3.98 g) as a brown oil.

NMR (CDCl₃-CD₃OD, δ): 0.93 ( 6H, d, J=7.5 Hz ), 1.75–2.05 (1H, m), 2.52 (2H, d, J=7.5 Hz), 7.13–7.32 (3H, m), 7.32–7.55 (1H, m)

PREPARATION 14

To a solution of 3-isobutylphenylamine (3.80 g) in 48% hydrobromic acid (10 ml) was added aqueous sodium nitrite (2.11 g, 2 ml) below 10° C. over 20 minutes. The reaction mixture was added to a solution of cuprous bromide (7.3 g) in 48% hydrobromic acid(5 ml) at 25° C. After stirred at 25° C. for 1 hour, the mixture was extracted with hexane two times. The extracts were combined, washed with water and brine, and dried over magnesium sulfate. After evaporation of the solvent, the residue was chromatographed on silica gel (150 g) eluting with hexane to give 1-bromo-3-isobutylbenzene (2.61 g) as a colorless oil.

NMR (CDCl₃, δ): 0.92 (6H, d, J=7.5 Hz), 1.72–1.98 (1H, m), 2.43 (2H, d, J=7.5 Hz), 7.00–7.22 (2H, m), 7.22–7.43 (2H, m)

PREPARATION 15

A mixture of 1-bromo-3-isobutylbenzene (3.16 g), magnesium (1.08 g), 1,2-dibromoethane (2.78 g) and iodine (10 mg) in tetrahydrofuran (10 ml) was refluxed for 1.5 hours. The mixture was cooled to 25° C., and a solution of 3-isobutylbenzaldehyde (2.40 g) in tetrahydrofuran (10 ml) was added at 25° C. After stirred for 1 hour at the same temperature, the mixture was poured into a mixture of ethyl acetate and 1N hydrochloric acid. The organic layer was separated, washed with water and brine, and dried over magnesium sulfate. After evaporation of the solvent, the residue was chromatographed on silica gel (200 g) eluting with 5% ethyl acetate in hexane to give bis(3-isobutylphenyl)methanol (2.90 g) as a colorless oil.

NMR (CDCl₃, δ): 0.89 (12H, d, J=7.5 Hz), 1.70–1.95 (2H, m), 2.46 (4H, d, J=7.5 Hz), 5.80 (1H, s), 6.97–7.09 (2H, m), 7.09–7.30 (6H, m)

PREPARATION 16

A mixture of bis(3-isobutylphenyl)methanol (2.87 g) and oxaly chloride (1 ml) in dichloromethane (10 ml) was stirred at 25° C. for 2 hours. After evaporation of the solvent, the oily residue was distilled to give bis(3-isobutylphenyl)chloromethane (2.45 g) as pale yellow oil.

bp: 150° C. (0.7 mmHg)

NMR (CDCl₃, δ): 0.8.9 (12H, d, J=7.5 Hz), 1.70–1.95 (2H, m), 2.45 (4H, d, J=7.5 Hz), 6.10 (1H, s), 7.02–7.14 (2H, m), 7.16–7.30 (6H, m)

PREPARATION 17

Benzyl 3-chloroformylpropionate was prepared from benzyl hydrogen succinate (1.96 g) and oxalyl chloride (0.9 ml) in an usual manner. A solution of sodium phenolate, which was prepared from phenol (1.77 g) and sodium hydride (60% dispersion in mineral oil, 1.13 g) in tetrahydrofuran (20 ml), was added to a solution of the acid chloride in tetrahydrofuran (20 ml) at 0° C. After stirred at 0° C. for 30 minutes, the mixture was poured into a mixture of ethyl acetate and 1N hydrochloric acid. The organic layer was separated, washed with water, and dried over magnesium sulfate. After evaporation of the solvent, the residue was chromatographed on silica gel (50 g eluting with a mixture of ethyl acetate and hexane (1:10→1:5) to give benzyl phenyl succinate (2.15 g) as colorless crystals.

NMR (CDCl₃, δ): 2.64–2.96 (4H, m), 5.17 (2H, s), 7.05 (2H, m), 7.2–7.45 (8H, m)

PREPARATION 18

To a solution of 4-[2,2-bis(4-isobutylphenyl)ethyl]benzoic acid (400 mg) in dichloromethane (10 ml) were added oxalyl chloride (0.1 ml) and a drop of N,N-dimethylformamide at 0° C. After stirred at 20° C. for 1 hour, the,mixture was evaporated to give 4-[2,2-bis(4-isobutylphenyl)ethyl]benzoyl chloride (450 mg) as pale yellow oil.

NMR (CDCl₃, δ): 0.88 (12H, d, J=7.5 Hz), 1.70–1.95 (2H, m), 2.41 (4H, d, J=7.5 Hz), 3.40 (2H, d, J=7.5 Hz), 4.16 (1H, t, J=7.5 Hz), 6.95–7.18 (10H, m), 7.90 (2H, d, J=8 Hz)

PREPARATION 19

To a suspension of powdered potassium hydroxide (168 g) in toluene (300 ml) was added 4-isobutylacetophenone (52.9 g), 18-crown-6 (79 mg) and methyliodide (149 ml). The mixture was stirred at 70° C. for 2 hours. The precipitate was filtered off and the filtrate was evaporated. The residue oil was distillated under reduced pressure to give 2,2-dimethyl-4'-isobutylpropiophenone as a colourless oil (23.0 g).

bp: 100°–105° C. (0.2 mmHg)

NMR (CDCl₃, δ): 0.90 (6H, d, J=7 Hz), 1.36 (9H, s), 1.90 (1H, m), 2.50 (2H, d, J=7 Hz), 7.17 (2H, d, J=8 Hz), 7.68 (2H, d, J=8 Hz)

PREPARATION 20

Propionyl chloride (13.0 ml) was added to a suspension of aluminum chloride (20.0 g) in dichloromethane (200 ml) at 0° C. After the mixture was stirred at 0° C for 1 hour, isobutylbenzene (23.6 ml) was added to the mixture. The mixture was stirred at 0° C. for 2 hours and poured into ice water. The organic layer was washed with water, dried over magnesium sulfate and evaporated. The residual oil was distilled under reduced pressure to give 4'-isobutylpropiophenone as a colourless oil (24.4 g).

NMR (CDCl$_3$, δ): 0.92 (6H, d, J=7 Hz), 1.21 (3H, t, J=7 Hz), 1.90 (1H, m), 2.53 (2H, d, J=7 Hz), 3.00 (2H, q, J=7 Hz), 7.23 (2H, d, J=5 Hz), 7.90 (2H, d, J=8 Hz)

PREPARATION 21

Sodium borohydride (4.72 g) was added to a solution of 2,2-dimethyl-4'-isobutylpropiophenone (22.7 g) in isopropyl alcohol (150 ml), The mixture was stirred at 50° C. for 2 hours and poured into ice water. After acidified with 6N-hydrochloric acid, the mixture was extracted with ethyl acetate. The organic layer was washed with water, dried over magnesium sulfate and evaporated to give 2,2-dimethyl-1-(4-isobutylphenyl)-propanol as a colourless oil (21.6 g).

NMR (CDCl$_3$, δ): 0.90 (6H, d, J=7 Hz), 0.92 (9H, s), 1.85 (1H, m), 2.45 (2H, d, J=7 Hz), 4.38 (1H, s), 7.08 (2H, d, J=8 Hz), 7.23 (2H, d, J=8 Hz)

PREPARATION 22

The following compound was obtained according to a similar manner to that of Preparation 21.

1-(4-Isobutylphenyl)propanol as a colourless oil

NMR (CDCl$_3$, δ): 0.88 (6H, d, J=7 Hz), 0.89 (3H, t, J=7 Hz), 1.6-2.0 (3H, m), 2.47 (2H, d, J=7 Hz), 4.57 (1H, t, J=7 Hz), 7.13 (2H, d, J=8 Hz), 7.25 (2H, d, J=8 Hz)

PREPARATION 23

To a mixture of 2,2-dimethyl-1-(4-isobutylphenyl)-propanol (22.8 g) and carbon tetrabromide (61.8 g) in tetrahydrofuran (250 ml) was added triphenylphosphine (48.9 g) under nitrogen atmosphere at 0° C. The mixture was stirred at room temperature for 6 hours. After the white solid was filtered off, the liltrate was evaporated. n-Hexane (250 ml) was added to the residue and the precipitate was filtered off. The filtrate was evaporated and the residual oil was distilled under reduced pressure to give 1-(1-bromoneopentyl)-4-isobutylbenzene as a colourless oil (10.3 g).

bp: 120°-125° C. (0.2 mmHg)

NMR (CDCl$_3$, δ): 0.90 (6H, d, J=7 Hz), 1.05 (9H, s), 1.86 (1H, m), 2.45 (2H, d, J=7 Hz), 4.85 (1H, s), 7.05 (2H, d, J=8 Hz), 7.28 (2H, d, J=8 Hz)

PREPARATION 24

The following compounds were obtained according to a similar manner to that of Preparation 23.

(1) 1-(1-Bromopropyl)-4-isobutylbenzene

NMR (CDCl$_3$, δ): 0.90 (6H, d, J=7 Hz), 1.01 (3H, t, J=7 Hz), 1.7-2.0 (1H, m), 2.0-2.4 (2H, m), 2.45 (2H, d, J=7 Hz), 4.89 (1H, t, J=7 Hz), 7.11 (2H, d, J=8Hz), 7.30 (2H, d, J=8Hz), (2) 2-Bromo-2-(4-isobutylphenyl)acetonitrile NMR (CDCl$_3$, δ): 0.90 (6H, d, J=7 Hz), 1.89 (1H, m), 2.51 (2H, d, J=7 Hz), 5.50 (1H, s), 7.21 (2H, d, J=9 Hz), 7.47 (2H, d, J=9 Hz)

(3) Benzyl 2-bromo-2-(4-isobutylphenyl)acetate

NMR (CDCl$_3$, δ): 0.90 (6H, d, J=7 Hz), 1.85 (1H, m), 2.48 (2H, d, J=7 Hz), 5.20 (2H, dd, J=11 Hz), 5.38 (1H, s), 7.12 (2H, d, J=9 Hz), 7.31 (5H, s), 7.43 (2H, d, J=9 Hz)

PREPARATION 25

A solution of methylmagnesium bromide in ether (4 ml) was added to a solution of 3-isobutylbenzaldehyde (1.0 g) in tetrahydrofuran (10 ml) at 0° C. After stirred at 0° C. for 30 minutes, the mixture was partitioned between ether and 1N hydrochloric acid. The organic layer was separated, washed with water and brine, and dried over magnesium sulfate. After evaporation of the solvent, the residue was chromatographed on silica gel (30 g) eluting with a mixture of ethyl acetate and hexane (1:10) to give 1-(3-isobutylphenyl)ethanol (1.12 g) as an oil.

NMR (CDCl$_3$, δ): 1.50 (3H, d, J=8 Hz), 1.90 (6H, d, J=8 Hz), 1.78-2.00 (1H, m), 2.48 (2H, d, J=8 Hz), 4.87 (1H, q, J=8 Hz), 7.00-7.32 (4H, m)

PREPARATION 26

A mixture of 1-(3-isobutylphenyl)ethanol (1.1 g), triphenylphosphine (3.24 g) and carbon tetrabromide (4.09 g) in ether (20 ml) was stirred at 25° C. for 1 hour. The precipitates were filtered off, and the liltrate was evaporated to give 1-(1-bromoethyl)-3-isobutylbenzene (1.49 g) as an oil.

NMR (CDCl$_3$, δ): 1.90 (6H, d, J=8 Hz), 1.75-1.98 (1H, m), 2.04 (3H, d, J=8 Hz), 2.48 (2H, d, J=8 Hz), 5.20 (1H, q, J=8 Hz), 7.00-7.10 (1H, m), 7.18-7.30 (2H, m), 7.40-7.75 (1H, m)

PREPARATION 27

A mixture of methyl 3-hydroxybenzoate (939 mg), 1-(1-bromoethyl)-3-isobutylbenzene (1.49 g) and potassium carbonate (1.71 g) in N,N-dimethylformamide (20 ml) was stirred at 25° C. overnight. The mixture was partitioned between ether and 1N hydrochloric acid. The organic layer was separated, washed with water and brine, dried over magnesium sulfate, and evaporated. The residue was chromatographed on silica gel (30 g) eluting with a mixture of ethyl acetate and hexane (1:10) to give methyl 3-[1-(3-isobutylphenyl)ethyl]benzoate (1.45 g) as an oil.

NMR (CDCl$_3$, δ): 0.85 (3H, d, J=8 Hz), 0.87 (3H, d, J=8 Hz), 1.65 (3H, d, J=8 Hz), 1.70-1.95 (1H, m), 2.46 (2H, d, J=8 Hz), 3.87 (3H, s), 5.34 (1H, q, J=8 Hz), 6.98-7.10 (2H, m), 7.13-7.30 (4H, m), 7.52-7.58 (2H, m)

PREPARATION 28

1N aqueous solution of sodium hydroxide (6 ml) was added to a solution of methyl 3-[1-( 3-isobutylphenyl ) ethoxy]benzoate ( 1.40 g ) in a mixture of 1.4-dioxane ( 12 ml ) and methanol ( 6 ml ). The reaction mixture was stirred at 25° C. for 18 hours, and then poured into a mixture of ether and 1N hydrochloric acid. The organic layer was separated, washed with water and brine, dried over magnesium sulfate, and evaporated. The crystalline residue was washed with hexane to give 3-[1-(3-isobutylphenyl ) ethoxy]benzoic acid ( 1.20 g) as colorless crystals.

NMR (CDCl$_3$, δ): 0.84 (3H, d, J=8 Hz), 0.87 ( 3H, d, J=8 Hz), 1.67 (3H, d, J=8 Hz), 1.72-1.95 (1H,m), 2.46 (2H, d, J=8 Hz), 5.25 (1H, q, J=8 Hz), 7.00-7.34 (6H, m), 7.58-7.66 (2H, m)

PREPARATION 29

A mixture of indole (11.7 g), ethyl 4-bromobutyrate (58.5 g) and potassium carbonate (41.5 g) in N,N-dimethylformamide (500 ml) was heated at 50° C. for 10 hours. The mixture was filtered and the filtrate was poured into a mixture of ethyl acetate and ice water. The organic layer was separated, washed with water, and dried over magnesium sulfate. After evaporation of the solvent, the residue was chromatographed on silica gel (1 kg) eluting with a mixture of methanol, chloroform and hexane (1:50:50) to give ethyl 4-(1-indolyl)butyrate (2.86 g) as a blue oil.

NMR (CDCl$_3$, δ): 1.24 (3H, t, J=7 Hz), 2.0–2.4 (4H, m), 4.13 (2H, q, J=7 Hz), 4.22 (2H, t, J=7 Hz), 6.50 (1H, d, J=3 Hz), 7.0–7.3 (3H, m), 7.36 (1H, d, J=7.5 Hz), 7.63 (1H, d, J=7.5 Hz)

PREPARATION 30

The following compounds were obtained according to a similar manner to that of Preparation 1.

(1) 5-Chloro-3-(3-nitrobenzoyl)indole mp: 265°–266° C.

NMR (DMSO-d$_6$, δ): 7.32 (1H, dd, J=2.5, 8 Hz), 7.57 (1H, d, J=5 Hz), 7.86 (1H, t, J=8 Hz), 8.17–8.29 (3H, m), 8.41–8.50 (2H, m)

(2) 2-Methyl-3-(3-nitrobenzoyl)indole mp: 219°–221° C. (dec.)

NMR (CDCl$_3$–CD$_3$OD, δ): 2.48 (3H, s), 6.88–7.18 (3H, m), 7.29 (1H, d, J=8 Hz), 7.60 (1H, t, J=8 Hz), 7.95 (1H, dif-dd, J=8 Hz), 8.31 (1H, dif-dd, J=8 Hz), 8.46 (1H, dif-d)

(3) Ethyl 4-[3-[3-(chloromethyl)benzoyl]indol-1-yl]butyrate mp: 87°–88° C.

NMR (CDCl$_3$, δ): 1.21 (3H, t, J=7 Hz), 2.1–2.4 (4H, m), 4.11 (2H, q, J=7 Hz), 4.26 (2H, t, J=7 Hz), 4.66 (2H, s), 7.3–7.7 (6H, m), 7.78 (1H, d, J=7.5 Hz), 7.86 (1H, broad s), 8.4–8.5 (1H, m)

(4) 3-(3,5-Dinitrobenzoyl)indole mp: 274°–275° C.

NMR (DMSO-d$_6$, δ): 7.4–7.5 (2H, m), 7.58 (1H, m), 8.22 (1H, d, J=4 Hz), 8.28 (1H, m), 8.83 (2H, J=2 Hz), 9.00 (1H, t, J=2 Hz)

(5) 3-(3-Methoxybenzoyl)indole

NMR (DMSO-d$_6$, δ): 4.52 (3H, s), 6.92–7.02 (1H, m), 7.12–7.40 (6H, m), 7.63 (1H, s), 8.15–8.22 (1H, m)

(6) 3-(4-Methoxybenzoyl)indole mp: 203°–205° C.

NMR (DMSO-d$_6$, δ): 3.70 (3H, s), 6.93 (2H, d, J=8 Hz), 7.00–7.19 (2H, m), 7.30–7.44 (1H, 7.67 (2H, d), 7.31 (1H, s), 8.02–8.15 (1H,

PREPARATION 31

3-[2,2-Bis(4-isobutylphenyl)ethyl]benzoic acid (1 g) was converted to 3-[2,2-bis(4-isobutylphenyl)ethyl]benzoyl chloride (1.13 g) with oxalyl chloride as an usual manner. To a solution of indole (0.918 g) in tetrahydrofuran (15 ml) was added 3M solution of methyl magnesium bromide in ether (3 ml) at 20° C., and the mixture was stirred at 20° C. for 1 hour. A solution of 3-[2,2-bis(4-isobutylphenyl)ethyl]benzoyl chloride (1.13 g) in tetrahydrofuran (15 ml) was added to the mixture at 20° C. After stirred at 20° C. for 1 hour, the mixture was poured into a mixture of 1N-hydrochloric acid and ethyl acetate. The organic layer was separated, washed with water, aqueous sodium bicarbonate and brine, and dried over magnesium sulfate. After evaporation of the solvent, the residue was purified by column chromatography on silica gel (50 g) eluting with a mixture of hexane and ethyl acetate (20:1) to give 3-[3-[2,2-bis(4-isobutylphenyl)ethyl]benzoyl]indole (468 mg) as pale red crystals.

mp: 72°–76° C.

NMR (CDCl$_3$, δ): 0.88 (12H, d, J=7.5 Hz), 1.67–1.92 (2H, m), 2.41 (4H, d, J=7.5 Hz), 3.39 (2H, d, J=7.5 Hz), 4.20 (1H, t, J=7.5 Hz), 6.93–7.47 (14H, m), 7.61 (1H, dif-dd, J=8 Hz), 8.35–8.47 (1H, m), 8.57 (1H, broad s)

PREPARATION 32

To a solution of indole (366 mg) in tetrahydrofuran (5 ml) was added 3M solution of methyl magnesium bromide in ether (1.5 ml) at 20° C., and the mixture was stirred at 20° C. for 1 hour. A solution of 4-[2,2-bis(4-isobutylphenyl)ethyl]benzoyl chloride (450 mg) in tetrahydrofuran (5 ml) was added to the mixture at 20° C. After stirred at 20° C. for 30 minutes, the mixture was poured into a mixture of 1N hydrochloric acid and ethyl acetate. The organic layer was separated, washed with water, aqueous sodium bicarbonate and brine, and dried over magnesium sulfate. After evaporation of the solvent, the residue was purified by column chromatography on silica gel (10 g) eluting with a mixture of hexane and ethyl acetate (20:1) to give 3-[4-[2,2-bis(4-isobutylphenyl)ethyl]benzoyl]indole (90 mg) as colorless crystals.

mp: 157°–160° C.

NMR (CDCl$_3$, δ): 0.87 (12H, d, J=7.5 Hz), 1.72–1.95 (2H, m), 2.42 (2H, d, J=7.5 Hz), 3.41 (2H, d, J=7.5 Hz), 4.19 (1H, t, J=7.5 Hz), 6.94–7.20 (11H, m), 7.25–7.46 (1H, m), 7.46–7.50 (1H, m), 7.59–7.72 (3H, m), 8.30–8.44 (1H, m), 8.61 (1H, s)

PREPARATION 33

A mixture of oxalyl chloride (562 mg) and N,N-dimethylformamide (0.57 ml) in dichloromethane (10 ml) was stirred at 25° C. for 1 hour. The mixture was cooled to −40° C., and a solution of 3-[1-(3-isobutylphenyl)ethoxy]benzoic acid (1.1 g) in dichloromethane (5 ml) was added to the mixture. The reaction mixture was stirred at −40° C. for 1 hour, and then was partitioned between hexane and ice-water. The organic layer was separated, washed with water and brine, dried over magnesium sulfate, and evaporated to give the acid chloride. A solution of methylmagnesium bromide in ether (3M, 3.1 ml) was added to a solution of indole (1.94 g) in tetrahydrofuran (20 ml) at 25° C. The reaction mixture was stirred at 25° C for 1 hour, and then a solution of the acid chloride in tetrahydrofuran (10 ml) was added at the same temperature. After stirred at 25° C. for 1 hour, the mixture was poured into a mixture of ethyl acetate and 1N hydrochloric acid. The organic layer was separated, washed with water and brine, dried over magnesium sulfate, and evaporated. The residue was chromatographed on silica gel (30 g) eluting with a mixture of ethyl acetate and hexane (10:1–4:1) to give 3-[3-[1-(3-isobutylphenyl)ethoxy]benzoyl]indole (650 mg) as an oil.

NMR (CDCl$_3$, δ): 0.75–0.80 (6H, m), 1.60–1.90 (4H, m), 2.42 (2H, d, J=8 Hz), 5.32 (1H, q, J=8 Hz), 6.95–7.45 (12H, m), 8.16–8.30 (1H, m)

PREPARATION 34

The following compounds were obtained according to a similar manner to that of Preparation 33.

(1) 3-[2,3-Dimethyl-4-[1-(4-isobutylphenyl)ethoxy]benzoyl]indole

NMR (DMSO-d$_6$, δ): 0.86 (6H, d, J=8 Hz), 1.60 (3H, d, J=8 Hz), 1.70–1.95 (1H, m), 2.18 (3H, s), 2.27 (3H, s), 2.44 (2H, d, J=8 Hz), 5.55 (1H, q, J=8 Hz), 6.78 (1H, d, J=10 Hz), 7.10 (1H, d, J=10 Hz), 7.16 (2H, d, J=9 Hz), 7.18–7.30 (2H, m), 7.36 (2H, d, J=9 Hz), 7.45–7.55 (2H, m), 8.12–8.20 (1H, m)

(2) 3-[3-(10,11-Dihydro-5H-dibenz[b,f]azepin-5-ylmethyl)-benzoyl]indole

NMR (DMSO-d$_6$, δ): 3.16 (4H, s), 5.06 (2H, s), 6.92 (2H, t, J=5 Hz), 7.05–7.30 (8H, m), 7.40–7.60 (4H, m), 7.65 (1H, dd, J=1, 8 Hz), 7.82 (1H, t, J=8 Hz), 7.82 (1H, t, J=1 Hz), 8.20–8.28 (1H, m)

PREPARATION 35

To a solution of ethyl 4-[3-(3-nitrobenzoyl)indol-1-yl]butyrate (0.5 g) in tetrahydrofuran (10 ml) were added sodium borohydride (99.4 mg) and boron trifluoride etherate (0.485 ml) at −25° C., and the mixture was stirred at the same temperature for 2 hours. The mixture was poured into a mixture of ethyl acetate and ice water. The organic layer was separated, washed with water and brine, and dried over magnesium sulfate. After evaporation of the solvent, the residue was chromatographed on silica gel (25 g) eluting with a mixture of ethyl acetate and hexane (1:4) to give ethyl 4-[3-(3-nitrobenzyl)indol-1-yl]butyrate (173 mg) as a yellow oil.

NMR (CDCl$_3$, δ): 1.24 (3H, t, J=7.5 Hz), 2.15 (2H, q, J=7.5 Hz), 2.30 (2H, t, J=7.5 Hz), 4.0–4.2 (6H, m), 6.88 (1H, s), 7.06 (1H, t, J=7.5 Hz), 7.21 (1H, t, J=7.5 Hz), 7.3–7.5 (3H, m), 7.60 (1H, d, J=7.5 Hz), 8.05 (1H, d, J=7.5 Hz), 8.14 (1H, broad s)

PREPARATION 36

The following compound was obtained according to a similar manner to that of Preparation 35.

3-(3-Nitrobenzyl)indole mp : 106°–107° C.

NMR (CDCl$_3$, δ): 4.23 (2H, s), 6.99 (1H, d, J=2 Hz), 7.07 (1H, dt, J=1.5, 7.5 Hz), 7.20 (1H, dt, J=1.5, 7.5 Hz), 7.3–7.5 (2H, m), 7.60 (1H, d, J=7.5 Hz), 8.0–8.2 (1H, m), 8.05 (1H, broad d, J=7.5 Hz), 8.14 (1H, broad s)

PREPARATION 37

The following compounds were obtained according to a similar manner to that of Preparation 2.

(1) Ethyl 3-[3-(3-nitrobenzoyl)indol-1-yl]propionate mp: 102°–103° C.

NMR (CDCl$_3$, δ): 1.20 (3H, t, J=7.5 Hz), 2.88 (2H, t, J=6 Hz), 4.13 (2H, q, J=7.5 Hz), 4.53 (2H, t, J=6 Hz), 7.3–7.5 (3H, m), 7.68 (1H, s), 7.70 (1H, t, J=7.5 Hz), 8.4–8.5 (2H, m), 8.62 (1H, t, J=2 Hz)

(2) Ethyl 5-[3-(3-nitrobenzoyl)indol-1-yl]valerate mp: 77°–78° C.

NMR (CDCl$_3$, δ): 1.23 (3H, t, J=7.5 Hz), 1.6–1.8 (2H, m), 1.8–2.1 (2H, m), 2.33 (2H, t, J=7 Hz), 4.09 (2H, q, J=7.5 Hz), 4.22 (2H, t, J=7 Hz), 7.3–7.5 (3H, m), 7.58 (1H, s), 7.71 (1H, t, J=7.5 Hz), 8.17 (1H, dt, J=2, 7.5 Hz), 8.4–8.5 (2H, m), 8.65 (1H, t, J=2 Hz)

(3) Ethyl 4-[5-chloro-3-(3-nitrobenzoyl)indol-1-yl]butyrate mp: 111°–113° C.

NMR (CDCl$_3$, δ): 1.22 (3H, t, J=7.5 Hz), 2.10–2.28 (2H, m), 2.32 (2H, t, J=7.5 Hz), 4.10 (2H, q, J=7.5 Hz), 4.25 (2H, t, J=7.5 Hz), 7.33 (1H, dd, J=2.5, 8 Hz), 7.40 (1H, d, J=8 Hz), 7.56 (1H, s), 7.72 (1H, t, J=8 Hz), 8.15 (1H, dif-dd, J=8 Hz), 8.36–8.46 (2H, m), 8.63 (1H, dif-d)

(4) Ethyl 4-[2-methyl-3-(3-nitrobenzoyl)indol-1-yl]butyrate mp: 92°–93° C.

NMR (CDCl$_3$, δ): 0.76 (3H, t, J=7.5 Hz), 2.05–2.25 (2H, m), 2.44 (2H, t, J=7.5 Hz), 2.69 (3H, s), 4.15 (2H, q, J=7.5 Hz), 4.25 (2H, t, J=7.5 Hz), 7.00–7.28 (3H, m), 7.41 (1H, d, J=8 Hz), 7.65 (1H, t, J=8 Hz), 8.10 (1H, dif-dd, J=8 Hz), 8.40 (1H, dif-dd, J=8 Hz), 8.58 (1H, dif-d)

Ethyl 4-[3-(3,5-dinitrobenzoyl)indol-1-yl]butyrate mp: 132°–133° C.

NMR (CDCl$_3$, δ): 1.23 (3H, t, J=6 Hz), 2.1–2.4 (4H, m), 4.10 (2H, q, J=7.5 Hz), 4.32 (2H, t, J=6 Hz), 7.3–7.6 (3H, m), 7.58 (1H, s), 8.3–8.5 (1H, m), 8.98 (2H, d, J=2 Hz), 9.20 (1H, t, J=2 Hz)

Ethyl 4-[3-(5-nitro-2-furoyl)indol-1-yl]butyrate mp: 97°–98° C.

NMR (CDCl$_3$, δ): 1.26 (3H, t, J=7.5 Hz), 2.2–2.5 ( 4H, m), 4.16 (2H, q, J=7.5 Hz), 4.36 (2H, t, J=6 Hz), 7.3–7.6 (5H, m), 8.47 (1H, s), 8.5–8.6 (1H, m)

(7) Ethyl 4-[3-(3-methoxybenzoyl)indol-1-yl]butyrate

NMR (CDCl$_3$, δ): 1.22 (3H, t, J=7.5 Hz), 2.15–2.40 (4H, m), 3.87 (3H, s), 4.12 (2H, q, J=7.5 Hz), 4.26 (2H, t, J=7.5 Hz), 7.06–7.15 (1H, m), 7.30–7.48 (6H, m), 7.59 (1H, s), 8.39–8.49 (1H, m)

(8) Ethyl 4-3-[4-methoxybenzoyl)indol-1-yl]butyrate

NMR (CDCl$_3$, δ): 1.20 (3H, t, J=7.5 Hz), 2.08–2.38 (4H, m), 3.38 (3H, s), 4.10 (2H, q, J=7.5 Hz), 4.23 (2H, t, J=7.5 Hz), 6.99 (2H, d, J=8 Hz), 7.28–7.48 (3H, m), 7.58 (1H, s), 7.85 (2H, d, J=8 Hz), 8.32–8.45 (1H, m)

PREPARATION 38

A solution of 3-(3-nitrobenzyl)indole (280 mg) in N,N-dimethylforma/nide (5 ml) was added to a suspension of sodium hydride (60% dispersion in mineral oil, 66.6 mg) in N,N-dimethylformamide (10 ml) at 0° C. The mixture was stirred at 25° C. for 40 minutes, and a solution of benZyl phenyl succinate (316 mg) in N,N-dimethylformamide was added at −40° C. After stirred at −40° C. for 20 minutes, the reaction mixture was poured into a mixture of ethyl acetate and 1N hydrochloric acid. The organic layer was separated, washed with water and brine, and dried over, magnesium sulfate. After evaporation of the solvent, the crude crystals were washed with hot isopropyl ether to give benzyl 4-[3-(3-nitrobenzyl)indol-1-yl]-4-oxobutyrate (364 mg).
mp: 100°–101° C.

NMR (CDCl$_3$, δ): 2.91 (2H, t, J=6 Hz), 3.24 (2H, t, J=6 Hz), 4.16 (2H, s), 5.16 (2H, s), 7.2–7.4 (9H, m), 7.48 (1H, t, J=7.5 Hz), 7.61 (1H, d, J=7.5 Hz), 8.11 (1H, d, J=8 Hz), 8.16 (1H, broad s), 8.44 (1H, d, J=8 Hz)

PREPARATION 39

Aluminum chloride (3.3 g) was added to a solution of ethyl 4-[3-(3-methoxybenzoyl)indolyl-1-yl]butyrate (3.0 g) in a mixture of ethanethiol (10 ml) and dichloromethane (10 ml) at 0° C., and the mixture was stirred at 25° C. for 1 hour. After evaporation of the solvent, 1N hydrochloric acid and ethyl acetate were added to the residue. The mixture was stirred at 25° C. for 30 minutes. The organic layer was separated, washed with water and brine, and dried over magnesium sulfate. After evaporation of the solvent, the residue was chromatographed on silica gel (100 g) eluting with chloroform to give ethyl 4-[3-(3-hydroxybenzoyl)indol-1-yl]butyrate (2.65 g) as an oil.

NMR (CDCl$_3$, δ): 1.22 (3H, t, J=7.5 Hz), 2.22–2.38 (4H, m), 4.12 (2H, q, J=7.5 Hz), 4.23 (2H, t, J=7.5 Hz), 7.00–7.12 (1H, m), 7.28–7.48 (6H, m), 7.62 (1H, s), 8.35–8.46 (1H, m)

PREPARATION 40

The following compound was obtained according to a similar manner to that of Preparation 39.

Ethyl 4-[3-(4-hydroxybenzoyl)indol-1-yl]butyrate mp: 129°–131° C.

NMR (CDCl$_3$, δ): 1.20 (3H, t, J=7.5 Hz), 2.08–2.40 (4H, m), 4.10 (2H, q, J=7.5 Hz), 6.91 (2H, d, J=8.0 Hz), 7.25–7.50 (3H, m), 7.60 (1H, s), 7.75 (2H, d, J=8.0 Hz), 8.30–8.42 (1H, m)

PREPARATION 41

Zinc iodide (0.21 g) was added to a mixture of 4-isobutylbenzaldehyde (6.5 g) and trimethylsilylcyanide (5.0 g). The mixture was stirred at room temperature for 30 minutes and partitioned between ethyl acetate and 7% hydrochloric acid. The organic layer was washed with 7% hydrochloric acid and water and dried over magnesium sulfate. The solvent was removed in vacuo to give 2-hydroxy-2-(4-isobutylphenyl)acetonitrile as a yellow oil (8.15 g).

NMR (CDCl$_3$, δ): 0.92 (6H, d, J=7 Hz), 1.87 (1H, m), 2.50 (2H, d, J=7 Hz), 5.50 (1H, s), 7.23 (2H, d, J=9 Hz), 7.42 (2H, d, J=9 Hz)

PREPARATION 42

2-Hydroxy-2-(4-isobutylphenyl)acetonitrile (7.35 g) was added to conc. hydrochloric acid (30 ml). The mixture was refluxed for 2 hours and poured into ice water (100 ml). The organic layer was extracted with ethyl acetate (20 ml), washed with water, dried over magnesium sulfate and evaporated. The residue was crystallized with n-hexane to give 2-hydroxy-2-(4-isobutylphenyl)acetic acid as a white solid (2.75 g).

NMR (CDCl$_3$, δ): 7.34 (2H, d, J=9 Hz), 7.15 (2H, d, J=9 Hz), 5.22 (1H, s), 2.48 (2H, d, J=7 Hz), 1.85 (1H, m), 0.90 (6H, d, J=7 Hz)

PREPARATION 43

To a solution of 2-hydroxy-2-(4-isobutylphenyl)acetic acid (3.8 g) in N,N-dimethylformamide (30 ml) was added potassium carbonate (7.6 g) and benzylbromide (2.2 ml). The mixture was stirred at room temperature for 4.5 hours and poured into ice water and 7% hydrochloric acid. The organic layer was extracted with ethyl acetate, washed with aqueous sodium bircarbonate solution and water, dried over magnesium sulfate and evaporated. The residual white powder was collected with n-hexane by filtration to give benzyl 2-hydroxy-2-(4-isobutylphenyl)acetate as a white powder (4.42 g).

NMR (CDCl$_3$, δ): 0.90 (6H, d, J=7 Hz), 1.85 (1H, m), 2,47 (2H, d, J=7 Hz), 3.40 (1H, d, J=6 Hz), 5.10 (2H, dd, J=11 Hz), 7.1–7.4 (9H, m)

PREPARATION 44

A mixture of ethyl 4-[5-chloro-3-(3-nitrobenzoyl)indol-1-yl]butyrate (2.00 g), 1N aqueous sodium hydroxide (7.5 ml), methanol (35 ml) and 1,4-dioxane (35 ml) was stirred at 25° C. for 6 hours. After evaporation of the organic solvent, 1N hydrochloric acid (15 ml) was added to the aqueous solution and the mixture was extracted with ethyl acetate. The extract was washed with water, dried over magnesium sulfate, and evaporated in vacuo. The crystalline residue was washed with hot ethanol to give 4-[5-chloro-3-(3-nitrobenzoyl)indol-1-yl]butyric acid (1.77 g) as colorless crystals.

mp: 198°–200° C.

NMR (DMSO-d$_6$, δ): 2.06 (2H, m), 2.30 (2H, t, J=7.5 Hz), 4.36 (2H, t, J=7.5 Hz), 7.45 (1H, dd, J=2.5, 8 Hz), 7.80 (1H, d, J=8 Hz), 7.91 (1H, t, J=8 Hz), 8.25–8.35 (3H, m), 8.45–8.55 (2H, m)

PREPARATION 45

The following compounds were obtained according to a similar manner to that of Preparation 44.

(1) 4-[2-Methyl-3-(3-nitrobenzoyl)indol-1-yl]butyric acid mp: 135°–138° C.

NMR (CDCl$_3$, δ): 2.08–2.25 (2H, m), 3.50 (2H, t, J=7.5 Hz), 2.66 (3H, s), 4.26 (2H, t, J=7.5 Hz), 7.00–7.30 (3H, m), 7.49 (1H, d, J=8.0 Hz), 7.65 (1H, t, J=8.0 Hz), 8.10 (1H, dif-dd, J=8.0 Hz), 8.40 (1H, dif-dd, J=8.0 Hz), 8.60 (1H, dif-d)

(2) 4-[3-(3-Hydroxybenzoyl)indol-1-yl]butyric acid

NMR (DMSO-d$_6$, δ): 1.75–1.95 (2H, m), 2.00 (2H, t, J=7.5 Hz), 3.97 (2H, t, J=7.5 Hz), 6.65–6.77 (1H, m), 6.88–7.08 (5H, m), 7.13–7.23 (1H, m), 7.51 (1H, s), 8.00–8.08 (1H, m)

(3) 4-[3-(4-Hydroxybenzoyl)indolyl-1-yl]butyric acid mp: 180°–182° C.

NMR (CDCl$_3$-CD$_3$OD, δ): 2.10–2.40 (4H, m), 4.25 (2H, t, J=7.5 Hz), 6.90 (2H, d, J=8.0 Hz), 7.25–7.51 (1H, m), 7.65 (1H, s), 7.75 (2H, d, J=8.0 Hz), 8.25–8.40 (1H, m)

PREPARATION 46

The following compounds were obtained according to a similar manner to that of Preparation 4.

(1) 3-(3-Aminobenzoyl)indole

NMR (DMSO-d$_6$, δ): 6.77 (1H, dt, J=8, 1 Hz), 6.90 (1H, dt, J=8, 1 Hz), 6.98 (1H, t, J=1 Hz), 7.16 (1H, t, J=8 Hz), 7.20–7.35 (2H, m), 7.6–7.5 (1H, m), 7.90 (1H, s), 8.2–8.3 (1H, m)

(2) Ethyl 3-[3-(3-aminobenzoyl)indol-1-yl]propionate

NMR (CDCl$_3$, δ): 1.18 (3H, t, J=7.5 Hz), 2.86 (2H, t, J=6 Hz), 4.10 (2H, q, J=7.5 Hz), 4.49 (2H, t, J=6 Hz), 6.90 (1H, dt, J=7.5, 2.5 Hz), 7.1–7.4 (6H, m), 7.70 (1H, s), 8.4–8.5 (1H, m)

(3) Ethyl 5-[3-(3-aminobenzoyl)indol-1-yl]valerate

NMR (CDCl$_3$, δ): 1.22 (3H, t, J=7.5 Hz), 1.6–1.8 (2H, m), 1.8–2.0 (2H, m), 2.32 (2H, t, J=7 Hz), 4.11 (2H, q, J=7.5 Hz), 4.18 (2H, t, J=7 Hz), 6.90 (1H, d, J=7.5 Hz), 7.1–7.5 (6H, m), 7.62 (1H, s), 8.4–8.5 (1H, m)

(4) 4-[3-(3-Aminobenzoyl)-5-chloroindol-1-yl]butyric acid mp: 178°–187° C.

NMR (CDCl$_3$-CD$_3$OD, δ): 2.10–2.25 (2H, m), 2.32 (2H, t, J=7.5 Hz), 4.26 (2H, t, J=7.5 Hz), 6.98 (1H, dif-dd, J=8 Hz), 7.15–7.45 (5H, m), 7.70 (1H, s), 8.40 (1H, d, J=2.5 Hz)

(5) 4-[3-(3-Aminobenzoyl)-2-methylindol-1-yl]butyric acid mp: 138°–154° C.

NMR (CDCl$_3$-CD$_3$OD, δ): 2.00–2.20 (2H, m), 2.40 (2H, t, J=7.5 Hz), 2.55 (3H, S), 4.22 (2H, t, J=7.5 Hz), 6.70–7.00 (1H, m), 7.00–7.32 (5H, m), 7.32–7.45 (2H, m)

(6) Ethyl 4-[3-(3-aminobenzyl)indol-1-yl]butyrate

NMR (CDCl$_3$, δ): 1.23 (3H, t, J=7.5 Hz), 2.13 (2H, m), 2.28 (2H, m), 4.01 (2H, s), 4.02–4.20 (4H, m), 6.54 (1H, dd, J=1.5, 7.5 Hz), 6.62 (1H, d, J=1.5 Hz), 6.77 (1H, dd, J=1.5, 7.5 Hz), 6.82 (1H, s), 7.0–7.4 (4H, m), 7.52 (1H, d, J=7.5 Hz)

(7) Ethyl 4-[3-(3,5-diaminobenzoyl)indol-1-yl]butyrate

NMR (CDCl$_3$, δ): 1.20 (3H, t, J=7.5 Hz), 2.1–2.4 (4H, m), 4.09 (3H, t, J=7.5 Hz), 4.21 (2H, t, J=6 Hz), 6.21 (1H, t, J=2 Hz), 6.53 (2H, d, J=2 Hz), 7.2–7.5 (3H, m), 7.64 (1H, s), 8.3–8.5 (1H, m)

(8) Ethyl 4-[3-(5-amino-2-furoyl)indol-1-yl]butyrate mp: 152°–153° C.

NMR (CDCl$_3$-CD$_3$OD, δ): 1.23 (3H, t, J=7.5 Hz), 2.1–2.5 (4H, m), 4.15 (2H, q, J=7.5 Hz), 4.27 (2H, t, J=6 Hz), 7.2–7.5 (5H, m), 7.97 (1H, s), 8.3–8.5 (1H, m)

(9) Ethyl 4-[3-(3-aminobenzoyl)indol-1-yl]butyrate

NMR (CDCl$_3$, δ): 1.23 (3H, t, J=7 Hz), 2.1–2.4 (4H, m), 4.10 (2H, q, J=7 Hz), 4.24 (2H, t, J=7 Hz), 6.90 (1H, dt, J=7.5, 2 Hz), 7.1–7.5 (6H, m), 7.62 (1H, s), 8.4–8.5 (1H, m)

PREPARATION 47

To a solution of benzyl 4-[3-(3-nitrobenzyl)indol-1-yl]-4-oxobutyrate (320 mg) in a mixture of 1,4-dioxane (6 ml) and methanol (3 ml) was added 10% palladium on activated carbon (60 mg), and the mixture was shaken under hydrogen atmosphere (3 atm) at 25° C. for 1.5 hours. The catalyst was filtered off and the filtrate was evaporated. The crude crystals were washed with hot chloroform and hot ethyl acetate to give 4-[3-(3-aminobenzyl)indol-1-yl]-4-oxobutyric acid (157 mg).

mp: 178° C.

NMR (CD$_3$OD-CDCl$_3$, δ): 2.82 (2H, t, J=6 Hz), 3.22 (2H, t, J=6 Hz), 3.96 (2H, s), 6.6–6.8 (3H, m), 7.10 (1H, t, J=7.5 Hz), 7.2–7.4 (3H, m), 7.45 (1H, d, J=7.5 Hz), 8.38 (1H, d, J=7.5 Hz)

PREPARATION 48

A mixture of ethyl 4-[3-(3,5-diaminobenzoyl)indol-1-yl]butyrate (1.99 g), di-tert-butyldicarbonate (8.30 g) and triethylamine (0.165 g) in dichloromethane (40 ml) was refluxed for 12 hours. After evaporation of the solvent, the residue was dissolved in ethyl acetate. The solution was washed with 1N hydrochloric acid, water, aqueous solution of sodium bicarbonate, and water in successively. After dryness over magnesium sulfate and evaporation of the solvent, the residue was chromatographed on silica gel (120 g) eluting with a mixture of ethyl acetate and hexane (1:2) to give ethyl 4-[3-[3,5-bis(tert-butoxycarbonylamino)benzoyl]indol-1-yl]butyrate (2.34 g) as an oil.

NMR (CDCl$_3$, δ): 1.22 (3H, t, J=7.5 Hz), 1.52 (18H, s), 2.2–2.4 (4H, m), 4.12 (2H, q, j=7.5 Hz), 4.26 (2H, t, J=6 Hz), 6.69 (2H, broad s), 7.3–7.5 (3H, m), 7.47 (1H, d, J=2 Hz), 7.76 (1H, s), 7.85 (1H, t, J=2 Hz), 8.4–8.5 (1H, m)

PREPARATION 49

To a solution of 3-(3-aminobenzoyl)indole (1.2 g) in N,N-dimethylformamide (12 ml) were added diisopropylethylamine (1.77 ml) and a solution of bis(4-isobutylphenyl)chloromethane (1.92 g) in N,N-dimethylformamide (5 ml) at 25° C., and the mixture was allowed to stand at the same temperature for 14 hours. The reaction mixture was partitioned between ethyl acetate and water, and the organic layer was washed with water and brine, dried over magnesium sulfate, and evaporated. The residue was chromatographed on silica gel (50 g) eluting with a mixture of ethyl acetate and chloroform (1:20) to give 3-[3-bis(4-isobutylphenyl)methylamino]benzoyl]indole (1.25 g) as pale yellow amorphous powder.

NMR (CDCl$_3$, δ): 0.90 (12H, d, J=8 Hz), 1.74–1.98 (2H, m), 2.46 (4H, d, J=8 Hz), 5.48 (1H, s), 6.75 (1H, d, J=8 Hz), 6.98 (1H, s), 7.04–7.42 (14H, m), 8.40–8.48 (1H, m), 8.57 (1H, broad s)

PREPARATION 50

To a solution of bis(4-chlorophenyl)methanol (2.0 g) and carbon tetrabromide (5.2 g) in tetrahydrofuran (30 ml) was added triphenylphosphine (4.2 g). The mixture was stirred at room temperature for 1 hours. After the mixture was filtered off, the solvent was removed in vacuo. The residue was dissolved in n-hexane (30 ml) and filtered off. The filtrate was evaporated and the residue was purified by distillation at reduced pressure to give bis(4-chlorophenyl)bromomethane as an oil (2.43 g).

NMR (CDCl$_3$, δ): 6.20 (1H, s), 7.2–7.4 (8H, m)

PREPARATION 51

The following compounds were obtained according to a similar manner to that of Preparation 48.

(1)
4-[3-[3-(tert-Butoxycarbonylamino)benzoyl]indol-1-yl]butyric acid

NMR (CDCl$_3$, δ): 1.51 (9H, s), 2.15–2.42 (4H, m), 4.27 (2H, t, J=7 Hz), 7.30–7.55 (7H, m), 7.64 (1H, s), 7.83 (1H, s), 8.40–8.50 (1H, m)

(2) Ethyl 4-[3-[3-(tert-butoxycarbonylamino)benzoyl]-indol-1-yl]butyrate

NMR (CDCl₃, δ): 1.22 (3H, t, J=7 Hz), 1.52 (9H, s), 2.17-2.40 (4H, m), 4.12 (2H, q, J=7 Hz), 4.26 (2H, t, J=7 Hz), 6.71 (1H, broad s), 7.30-7.55 (5H, m), 7.63-7.80 (3H, m), 8.40-8.50 (1H, m)

PREPARATION 52

A solution of 4-[3-[3-(tert-butoxycarbonylamino)-benzoyl]indolyl-1-yl]butyric acid (296 mg) in N,N-dimethylformamide (5 ml) was added to a suspension of sodium hydride (62 mg) in N,N-dimethylformamide (2 ml) at 0° C. The mixture was stirred at 20° C. for 1 hour, and then ethyl iodide (546 mg) was added. The mixture was stirred at 20° C. for 20 hours, and partitioned between ethyl acetate and 0.1N hydrochloric acid. The organic layer was washed with water and brine, dried over magnesium sulfate, and evaporated. The residue was chromatographed on silica gel eluting with a mixture of hexane and ethyl acetate (4:1) to obtain ethyl 4-[3-[3-(N-ethyl-N-tert-butoxycarbonylamino)benzoyl]indol-1-yl]butyrate (220 mg) as an oil.

NMR (CDCl₃, δ): 1.14-1.28 (6H, m), 1.48 (9H, s), 2.13-2.38 (4H, m), 3.73 (2H, q, J=7 Hz), 4.11 (2H, q, J=7 Hz), 4.27 (2H, J=7 Hz), 7.30-7.50 (5H, m), 7.62-7.73 (3H, s), 8.38-8.48 (1H, m)

PREPARATION 53

The following compound was obtained according to a similar manner to that of Preparation 52.

Methyl 4-[3-[3-(N-methyl-N-tert-butoxycarbonylamino)benzoyl]indol-1-yl]butyrate

NMR (CDCl₃, δ): 1.50 (9H, s), 2.15-2.42 (4H, m), 3.33 (3H, s), 3.66 (3H, s), 4.27 (2H, t, J=7 Hz), 7.30-7.52 (5H, m), 7.56-7.70 (2H, m), 7.76 (1H, s), 8.40-8.50 (1H, m)

PREPARATION 54

A solution of ethyl 4-[3-[3-(tert-butoxycarbonylamino)benzoyl]indol-1-yl]butyrate (1.73 mg) in tetrahydrofuran (20 ml) was added to a suspension of sodium hydride (307 mg) in tetrahydrofuran (10 ml) at 0° C. The mixture was stirred at 0° C. for 15 minutes, and then a solution of methyl iodide (1.64 g) in tetrahydrofuran (5 ml) was added. The mixture was stirred at 0° C. for 2 hours, and partitioned between ethyl acetate and 0.1N hydrochloric acid. The organic layer was washed with water and brine, dried over magnesium sulfate, and evaporated. The residue was chromatographed on silica gel eluting with a mixture of hexane and ethyl acetate (3:1) to obtain ethyl 4-[3-[3-(N-methyl-N-tert-butoxycarbonylamino)benzoyl]indol-1-yl]butyrate (1.03 g) as an oil.

NMR (CDCl₃, δ): 1.22 (3H, t, J=7 Hz), 1.50 (9H, s), 2.15-2.40 (4H, m), 3.32 (3H, s), 4.12 (2H, q, J=7 Hz), 4.27 (2H, t, J=7 Hz), 7.30-7.50 (5H, m), 7.56-7.65 (1H, m), 7.68 (1H, s), 7.76 (1H, s), 8.40-8.50 (1H, m)

PREPARATION 55

To a solution of ethyl 4-[3-[3-(N-ethyl-N-tert butoxycarbonylamino)benzoyl]indol-1-yl]butyrate (220 mg) in 1,4-dioxane (2 ml) was added 4N hydrogen chloride in 1,4-dioxane (2 ml) at 0° C., and the mixture was stirred at 20° C. for 1 hour. After evaporation of the solvent, the residue was partitioned between ethyl acetate and aqueous sodium bicarbonate. The organic layer was washed with water and brine, dried over magnesium sulfate, and evaporated to obtain ethyl 4-[3-[(3-ethylaminobenzoyl)indol-1-yl]butyrate (157 mg) as an oil.

NMR (CDCl₃, δ): 1.21 (3H, t, J=7 Hz), 1.30 (3H, t, J=7 Hz), 2.10-2.40 (4H, m), 3.23 (2H, q, J=7 Hz), 4.10 (2H, q, J=7 Hz), 4.25 (2H, t, J=7 Hz), 6.80-6.90 (1H, m), 7.10-7.20 (2H, m), 7.24-7.50 (7H, m), 7.63 (1H, s), 8.40-8.50 (1H, m)

PREPARATION 56

The following compounds were obtained according to a similar manner to that of Preparation 55.

(1) Methyl 4-[3-(3-methylaminobenzoyl)indol-1-yl]-butyrate

NMR (CDCl₃, δ): 2.12-2.40 (4H, m), 2.91 (3H, s), 3.66 (3H, s), 4.25 (2H, t, J=7 Hz), 6.84-7.94 (1H, m), 7.13-7.50 (6H, m), 7.63 (1H, s), 8.40-8.50 (1H, m)

(2) Ethyl 4-[3-(3-methylaminobenzoyl)indol-1-yl]butyrate

NMR (CDCl₃, δ): 1.21 (3H, t, J=7 Hz), 2.10-2.38 (4H, m), 2.88 (3H, s), 4.10 (2H, q, J=7 Hz), 4.25 (2H, t, J=7 Hz), 6.77-6.87 (1H, m), 7.07-7.18 (2H, m), 7.23-7.50 (4H, m), 7.62 (1H, s), 8.40-8.50 (1H, m)

PREPARATION 57

To a solution of 10,11-dihydro-5H-dibenz[b,f]azepine (2.44 g) in tetrahydrofuran (25 ml) was added potassium tert-butoxide (2.02 g) at 0° C. The mixture was stirred at 0° C. for 15 minutes, and then a solution of methyl 3-(chloromethyl)benzoate (3.57 g) in tetrahydrofuran (15 ml) was added. The mixture was stirred at 25° C. for 1 hour, and then evaporated. The residue was partitioned between ethyl acetate and 0.1N hydrochloric acid. The organic layer was washed with water and brine, dried over magnesium sulfate, and evaporated. The residue was chromatographed on silica gel eluting with a mixture of hexane and ethyl acetate (40:1) to give methyl 3-(10,11-dihydro-5H-dibenz[b,f]azepin-5-ylmethyl)benzoate (1.10 g) as an oil.

NMR (CDCl₃, δ): 3.24 (4H, s), 3.39 (3H, s), 5.00 (2H, s), 6.80-6.96 (2H, m), 7.00-7.15 (6H, m), 7.30 (1H, t, J=8 Hz), 7.66 (1H, dd, J=1, 8 Hz), 7.83 (1H, dd, J=1.8 Hz), 8.10 (1H, t, J=1 Hz)

PREPARATION 58

1N aqueous solution of sodium hydroxide (9 ml) was added to a solution of methyl 3-(10,11-dihydro-5H-dibenz[b,f]azepin-5-ylmethyl)benzoate (1.06 g) in a mixture of 1,4-dioxane (25 ml) and methanol (15 ml) at 25° C. The mixture was stirred at 25° C. for 3 hours, and then at 50° C. for 30 minutes. After evaporation of the solvent, the residue was partitioned between ethyl acetate and 0.1N hydrochloric acid. The organic layer was separated, washed with water and brine, dried over magnesium sulfate, and evaporated to give 3-(10,11-dihydro-5H-dibenz[b,f]azepin-5-ylmethyl)benzoic acid (1.01 g) as powder.

NMR (CDCl₃, δ): 3.26 (4H, s), 5.02 (2H, s), 6.85-6.96 (2H, m), 7.00-7.20 (6H, m), 7.32 (1H, t, J=8 Hz), 7.64 (1H, dd, J=1, 8 Hz), 7.90 (1H, dd, J=1, 8 Hz), 8.17 (1H, t, J=1 Hz)

PREPARATION 59

A solution of 5-nitro-2-furoyl chloride, which was prepared with 5-nitro-2-furoic acid (2.0 g) and oxalyl chloride (1.4 ml) in an usual manner, in dichloromethane (10 ml) was added to a suspension at aluminum chloride (1.78 g) at 25° C. The mixture was stirred at 25° C. for 30 minutes, and then a solution of indole (1.49 g) in dichloromethane (15 ml) was added at 25° C. The mixture was stirred at 25° C. for 1 hour, and poured into ice water. The precipitates were filtered and washed with water, ethyl acetate and hot ethanol to give 3-(5-nitro-2-furoyl)indole (1.08 g) as yellow powder.

mp: 311–312° C.

NMR (DMSO-$d_6$, $\delta$): 7.2–7.4 (2H, m), 7.5–7.5 (1H, m), 7.61 (1H, d, J=5 Hz), 7.85 (1H, d, J=5 Hz), 8.2–8.4 (1H, m), 8.57 (1H, m)

PREPARATION 6

To a solution of phenoxazine (2.20 g) in tetrahydrofuran (30 ml) was added potassium tert-butoxide (2.69 g) at 0° C. The mixture was stirred at 0° C. for 10 minutes, and then a solution of methyl 3-(chloromethyl)benzoate (2.44 g) in tetrahydrofuran (20 ml) was added. The mixture was stirred at 25° C. for 30 minutes, and then evaporated. The residue was partitioned between ethyl acetate and 0.1N hydrochloric acid. The organic layer was washed with water and brine, dried over magnesium sulfate, and evaporated. The residue was purified by chromatography on silica gel eluting with a mixture of hexane and ethyl acetate (40:1–20:1) and recrystallization from a mixture of hexane and ethyl acetate to give e methyl 3-(phenoxazin-10-ylmethyl)benzoate (1.12 g) as crystals.

NMR (CDCl$_3$, $\delta$): 3.92 (3H, s), 4.82 (2H, s), 6.26–6.35 (2H, m), 6.65–6.75 (6H, m), 7.37–7.56 (2H, m), 7.90–8.05 (2H, m)

PREPARATION 61

To a solution of phenothiazine (1.00 g) in tetrahydrofuran (10 ml) was added potassium tert-butoxide (617 mg) at 0° C. The mixture was stirred at 0° C. for 20 minutes, and then a solution of methyl 3-(chloromethyl)benzoate (1.02 g) in tetrahydrofuran (10 ml) was added. The mixture was stirred at 25° C. for 3 hours, and then potassium tert-butoxide (1.02 g) was added. The mixture was stirred at 25° C. for 1 hour, and then evaporated. The residue was partitioned between ethyl acetate and 0.1N hydrochloric acid. The organic layer was washed with water and brine, dried over magnesium sulfate, and evaporated. The residue was chromatographed on silica gel eluting with a mixture of .hexane and ethyl acetate (40:1) to give tert-butyl 3-(phenothiazin-10-ylmethyl)benzoate (598 mg) as crystals.

NMR (CDCl$_3$, $\delta$): 1.60 (9H, s), 5.13 (2H, s), 6.63 (2H, d, J=8 Hz), 6.80–7.05 (4H, m), 7.12 (1H, dd, J=1, 8 Hz), 7.25–7.50 (2H, m), 7.86 (1H, d, J=8 Hz), 8.04 (1H, broad s)

PREPARATION 62

The following compounds were obtained according to a similar manner to that of Preparation 28.

(1) 3-(Phenoxazin-10-ylmethyl)benzoic acid

NMR (CDCl$_3$-CD$_3$OD=1:1, $\delta$): 4.84 (2H, s), 6.34 (2H, broad s), 6.65–6.75 (6H, m), 7.38–7.55 (2H, m), 7.92–8.06 (2H, m)

(2) 3-(Phenothiazin-10-ylmethyl)benzoic acid

NMR (CDCl$_3$, $\delta$): 5.16 (2H, s), 6.62 (2H, d, J=8 Hz), 6.80–7.06 (4H, m), 7.12 (2H, dd, J=1, 8 Hz), 7.33–7.68 (2H, m), 7.76–8.15 (2H, m)

PREPARATION 63

The following compounds were obtained according to a similar manner to that of Preparation 33.

(1) 3-[3-(Phenoxazin-10-ylmethyl)benzoyl]indole

NMR (DMSO-$d_6$, $\delta$): 5.20 (2H, s), 6.56–6.88 (7H, m), 7.18–7.34 (2H, m), 7.46–7.75 (5H, m), 7.85 (2H, d, J=2 Hz), 8.20–8.35 (1H, m)

(2) 3-[3-(Phenothiazin-10-ylmethyl)benzoyl]indole

NMR (CDCl$_3$-CD$_3$OD=1:1, $\delta$): 5.23 (2H, s), 6.70–7.85 (17H, m), 8.32=8.40 (1H, m)

PREPARATION 64

To a solution of 4,4'-dichlorobenzophenone (2.51 g) in isopropyl alcohol (15 ml) was added sodium borohydride (0.45 g). The mixture was stirred for 4 hours at 50° C. and poured into diluted hydrochloric acid (60 ml). The organic layer was extracted with ethyl acetate (20 ml) and washed with water (30 ml×2). The solution was dried over magnesium sulfate. The solvent was removed in vacuo to give colorless oil of bis(4-chlorophenyl)methanol (2.50 g)

NMR (CDCl$_3$, $\delta$): 5.70 (1H, s), 7.2–7.4 (8H, m)

EXAMPLE 1

A mixture of 4-[3-(3-aminobenzoyl)indol-1-yl]butyric acid (880 mg), bis(4-isobutylphenyl)methyl chloride (1.03 g) and diisopropylethylamine (0.945 g) in dichloromethane (20 ml) was stirred at 25° C. overnight, and bis(4-isobutylphenyl)methyl chloride (170 mg) and diisopropylethylamine (86 mg) were added thereto. After stirring at 25° C. for 3 hours, the reaction mixture was poured into cold 1N hydrochloric acid. The organic layer was separated, washed with water, and dried over magnesium sulfate. After evaporation of the solvent, the residue was chromatographed on silica gel (100 g) with a mixture of chloroform and methanol (50:1) as eluent and freeze-dried from benzene to give 4-[3-[3-[bis(4-isobutylphenyl)methylamino]benzoyl]indol-1-yl]butyric acid (820 mg) as pale yellow powder.

NMR (CDCl$_3$, $\delta$): 0.89 (12H, d, J=7.5 Hz), 1.85 (2H, m), 2.17 (2H, m), 2.28–2.50 (6H, m), 4.20 (2H, t, J=7.5 Hz), 5.51 (1H, s), 6.78 (1H, broad d), 7.00–7.48 (15H, m), 8.45 (1H, m)

EXAMPLE 2

The following compound was obtained according to a similar manner to that of Example 1.

4-[3-[4-[Bis(4-isobutylphenyl)methylamino]benzoyl]indol-1-yl]butyric acid

NMR (CDCl$_3$, $\delta$): 0.92 (12H, d, J=7.5 Hz), 1.2–1.9 (2H, m), 2.18 (2H, quintet, J=7.5 Hz), 2.38 (2H, t, J=7.5 Hz), 2.45 (4H, d, J=7.5 Hz), 4.22 (2H, t, J=7.5 Hz), 5.54 (1H, s), 6.55 (2H, d, J=8 Hz), 7.08 (2H, d, J=8 Hz), 7.22 (2H, d, J=8 Hz), 7.25–7.40 (2H, m), 7.55 (1H, s), 7.70 (2H, d, J=8 Hz), 8.30 (1H, m)

EXAMPLE 3

The following compounds were obtained according to a similar manner to that of Example 1.

(i) Ethyl 3-[3-[3-[bis(4-isobutylphenyl)methylamino]benzoyl]indol-1-yl]propionate NMR (CDCl$_3$, δ): 0.88 (12H, d, J=7 Hz), 1.16 (3H, t, J=7.5 Hz), 1.84 (2H, m), 2.43 (4H, d, J=7 Hz), 2.80 (2H, t, J=7 Hz), 4.08 (2H, q, J=7 Hz), 4.41 (2H, t, J=7 Hz), 5.53 (1H, s), 6.71 (1H, d, J=7.5 Hz), 7.0–7.4 (6H, m), 7.10 (4H, d, J=8 Hz), 7.25 (4H, d, J=8 Hz), 7.54 (1H, s), 8.4–8.5 (1H, m)

(2) Ethyl 5-[3-[3-[bis(4-isobutylphenyl)methylamino]benzoyl]indol-1-yl]valerate

NMR (CDCl$_3$, δ): 0.89 (12H, d, J=7 Hz), 1.19 (3H, t, J=7.5 Hz), 1.5–1.7 (2H, m), 1.7–2.0 (4H, m), 2.30 (2H, t, J=7.5 Hz), 2.45 (4H, d, J=7 Hz), 4.0–4.2 (4H, m), 5.53 (1H, s), 6.71 (1H, d, J=7.5 Hz), 7.09 (4H, d, J=8 Hz), 7.25 (4H, d, J=8 Hz), 7.0–7.4 (6H, m), 7.46 (1H, s), 8.4–8.5 (1H, m)

(3) 4-[3-[3-[Bis(4-isobutylphenyl)methylamino]benzoyl]-5-chloroindol-1-yl]butyric acid mp: 150°–152° C.

NMR (CDCl$_3$, δ): 0.85 (12H, d, J=7.5 Hz), 1.70–1.95 (2H, m), 2.05–2.20 (2H, m), 2.31 (2H, m), 2.43 (4H, d, J=7.5 Hz), 4.14 (2H, t, J=7.5 Hz), 5.50 (1H, s), 6.70 (1H, d, J=8 Hz), 6.95–7.40 (13H, m), 7.45 (1H, s), 8.41 (1H, s)

(4) 4-[3-[3-[Bis(4-isobutylphenyl)methylamino]benzoyl]-2-methylindol-1-yl]butyric acid NMR (CDCl$_3$, δ): 0.85 (12H, d, J=7.5 Hz), 1.70–1.93 (2H, m), 2.00–2.20 (2H, m), 2.44–2.52 (9H, m), 4.19 (2H, t, J=7.5 Hz), 5.49 (1H, s), 6.63–6.75 (1H, m), 6.92–7.55 (15H, m)

(5) 4-[3-[3-Bis(3-isobutylphenyl)methylamino]benzoyl]indol-1-yl]butyric acid

NMR (CDCl$_3$, δ): 0.78 (12H, d, J=7.5 Hz), 1.50–1.82 (2H, m), 1.95–2.18 (2H, m), 2.18–2.40 (6H, m), 4.08 (2H, t, J=7.5 Hz), 5.42 (1H, s), 6.61–6.78 (1H, m), 6.90–7.38 (15H, m), 8.28–8.40 (1H, m)

(6) Ethyl 4-[3-[3-[bis(4-isobutylphenyl)methylamino]benzyl]indol-1-yl]butyrate

NMR (CDCl$_3$, δ): 0.88 (12H, d, J=7 Hz), 1.22 (3H, t, J=6 Hz), 1.82 (2H, m), 2.12 (2H, quin, J=6 Hz), 2.26 (2H, t, J=6 Hz), 2.42 (4H, d, J=7 Hz), 3.95 (2H, s), 4.0–4.2 (2H, m), 4.10 (2H, q, J=6 Hz), 5.40 (1H, s), 6.36 (1H, d, J=7.5 Hz), 6.52 (1H, broad s), 6.62 (1H, d, J=7.5 Hz), 6.76 (1H, s), 7.06 (4H, d, J=8 Hz), 7.22 (4H, d, J=8 Hz), 6.9–7.4 (4H, m), 7.48 (1H, d, J=7.5 Hz)

(7) 4-[3-[3-[Bis(4-isobutylphenyl)methylamino]benzyl]indol-1-yl]-4-oxobutyric acid NMR (CDCl$_3$, δ): 0.87 (12H, d, J=7 Hz), 1.82 (2H, m), 2.41 (4H, d, J=7 Hz), 2.86 (2H, t, J=6 Hz), 3.18 (2H, t, J=6 Hz), 3.88 (2H, s), 5.37 (1H, s), 6.40 (1H, d, J=7.5 Hz), 6.46 (1H, broad s), 6.61 (1H, d, J=7.5 Hz), 7.0–7.5 (13H, m), 8.40 (1H, d, J=7.5 Hz)

(8) Ethyl 4-[3-[5-[bis(4-isobutylphenyl)methylamino]-2-furoyl]indol-1-yl]butyrate (9) Ethyl 4-[3-[3-bis(4-isobutylphenyl)methylamino]benzoyl]indol-1-yl]butyrate NMR (CDCl$_3$, δ): 0.88 (12H, d, J=7.5 Hz), 1.20 (3H, t, J=8 Hz), 1.85 (2H, m), 2.2–2.4 (4H, m), 2.45 (4H, d, J=8 Hz), 4.08 (2H, q, J=8 Hz), 4.18 (2H, t, J=7.5 Hz), 5.52 (1H, s), 6.72 (1H, d, J=8 Hz), 7.0–7.5 (15H, m), 8.45 (1H, m)

(10) 4-[3-[3-[1-(4-Isobutylphenyl)ethylamino]benzoyl]indol-1-yl]butyric acid

NMR (CDCl$_3$, δ): 8.43 (1H, m), 7.45 (1H, s), 7.0–7.4 (10H, m), 6.67 (1H, d, J=7.5 Hz), 4.52 (1H, q, J=7 Hz), 4.20 (2H, m), 2.43 (2H, d, J=537 7.5 Hz), 2.35 (2H, m), 2.1–2.3 (2H, m), 1.7–2.0 (1H, m), 1.51 (3H, d, J=7 Hz), 0.90 (6H, d, J=7.5 Hz)

(11) 4-[3-[4-[1-(4-Isobutylphenyl)ethylamino]benzoyl]indol-1-yl]butyric acid

NMR (CDCl$_3$, δ): 8.30 (1H, m), 7.70 (2H, d, J=9 Hz), 7.51 (1H, s), 7.2–7.5 (5H, m), 7.10 (2H, d, J=9 Hz), 6.5–6.7 (2H, m), 4.56 (1H, q, J=7 Hz), 4.23 (2H, m), 2.45 (2H, d, J=7.5 Hz), 2.35 (2H, m), 1.7–2.0 (1H, m), 1.60 (3H, d, J=7 Hz), 0.87 (6H, d, J=7.5 Hz).

(12) Ethyl 4-[3-[3-[(cyano)(4-isobutylphenyl)methylamino]benzoyl]indol-1-yl]butyrate NMR (CDCl$_3$δ): 8.5–8.4 (1H, m), 7.75 (1H, s), 7.2–7.6 (10H, m), 6.9–7.0 (1H, m), 5.50 (1H, s), 4.25 (2H, t, J=7 Hz), 4.05 (2H, q, J=7 Hz), 2.51 (2H, d, J=7 Hz), 2.2–2.4 (4H, m), 1.90 (1H, m), 1.18 (3H, t, J=7 Hz), 0.92 (6H, d, J=7 Hz)

(13) Ethyl 4-[3-[3-[(benzyloxycarbonyl)(4-isobutylphenyl)methylamino]benzoyl]indol-1-yl]butyrate NMR (CDCl$_3$, δ): 0.90 (6H, d, J=7 Hz), 1.20 (3H, t, J=7 Hz), 1.85 (1H, m), 2.1–2.4 (4H, m), 2.46 (2H, d, J=7 Hz), 4.08 (2H, q, J=7 Hz), 4.15–4.3 (2H, m), 5.15 (2H, s), 5.17 (1H, s), 6.7–6.9 (1H, m), 7.1–7.5 (15H, m), 7.50 (1H, s), 8.4–8.5 (1H, m)

(14) Ethyl 4-[3-[3-[bis(4-chlorophenyl)methylamino]benzoyl]indol-1-yl]butyrate

NMR (CDCl$_3$, δ): 1.22 (3H, t, J=7 Hz), 2.0–2.4 (4H, m), 4.0–4.2 (4H, m), 5.52 (1H, s), 6.7–6.8 (1H, m), 6.95–7.1 (1H, m), 7.1–7.5 (14H, m), 8.4–8.5 (1H, m)

(15) 4-[3-[3-[(Benzyloxycarbonyl)(4-isobutylphenyl)methylamino]benzoyl]indol-1-yl]butyric acid NMR (CDCl$_3$, δ): 0.87 (6H, d, J=7 Hz), 1.82 (1H, m), 2.1–2.4 (4H, m), 2.44 (2H, d, J=7 Hz), 4.20 (2H, t, J=7 Hz), 5.17 (2H, s), 5.20 (1H, s), 6.2–6.3 (1H, m), 7.0–7.4 (15H, m), 7.49 (1H, s), 8.4–8.5 (1H, m)

EXAMPLE 4

A mixture of ethyl 4-[3-(3-aminobenzoyl)indol-1-yl]butyrate (1.0 g) and p-isobutylbenzyl chloride (1.56 g) and potassium carbonate (1.18 g) in N,N-dimethylformamide (20 ml) was heated at 100° C. for 23 hours. More p-isobutylbenzyl chloride (0.52 g) and potassium carbonate (0.394 g) were added, and the mixture was heated at 100° C. for 30 minutes. The reaction mixture was poured into ice water and was extracted with ethyl acetate. The extract was washed with water, and dried over magnesium sulfate. After evaporation of the solvent, the residue was chromatographed on silica gel (100 g) eluting with a mixture of ethyl acetate and hexane (1:4→1:3) to give ethyl 4-[3-[3-[bis(4-isobutylbenzyl)amino]benzoyl]indol-1-yl]butyrate (1.06 g, Compound I) and ethyl 4-[3-3-(4-isobutylbenzyl)aminobenzoyl]indol-1-yl]butyrate (184 mg, Compound II).

Compound I

NMR (CDCl$_3$, δ): 0.90 (12H, d, J=7 Hz), 1.20 (3H, t, J=7 Hz), 1.84 (2H, m), 2.10 (2H, quin, J=7 Hz), 2.23 (2H, t, J=7 Hz), 2.45 (4H, d, J=7 Hz), 4.0–4.2 (4H, m), 4.67 (4H, s), 6.92 (1H, broad d, J=7.5 Hz), 7.0–7.5 (15H, m), 8.4–8.5 (1H, m)

Compound II

NMR (CDCl$_3$, δ): 0.90 (6H, d, J=7 Hz), 1.21 (3H, t, J=7 Hz), 1.85 (1H, m), 2.1–2.4 (4H, m), 2.46 (2H, d, J=7 Hz), 4.10 (2H, q, J=7 Hz), 4.21 (2H, t, J=7 Hz), 4.35 (2H, s), 6.82 (1H, d, J=7.5 Hz), 7.1–7.5 (10H, m), 7.57 (1H, s), 8.4–8.5 (1H, m)

EXAMPLE 5

A solution of 4-[3-(3-hydroxybenzoyl)indol-1-yl]butyric acid (500 mg) in N,N-dimethylformamide (5 ml) was added to a suspension of sodium hydride (60% dispersion in mineral oil, 136 mg) in N,N-dimethylformamide (10 ml) at 25°. The mixture was stirred at 25° C. for 1 hour, and a solution of bis (4-isobutylphenyl)-bromomethane (1.11 g) in tetrahydrofuran (10 ml) was added at 0° C. After stirred at 25° C. overnight, the mixture was poured into a mixture of ethyl acetate and 1N hydrochloric acid. The organic layer was separated, washed with water and brine, and dried over magnesium sulfate. After evaporation of the solvent, the residue was chromatographed on silica gel (20 g) eluting with 2% methanol in chloroform to give 4-[3-[3-[bis(4-isobutylphenyl)methoxy]benzoyl]indol-1-yl]butyric acid (120 mg) as colorless crystals.

mp: 154°–156° C.

NMR (CDCl$_3$, δ): 0.88 (12H, d, J=7.5 Hz), 1.70–1.95 (2H, m), 2.08–2.26 (2H, m), 2.34 (t, 2H, J=7.5 Hz), 2.44 (4H, d, J=8 Hz), 4.20 (2H, t, J=7.5 Hz), 6.26 (1H, s), 6.90–7.40 (15H, m), 7.44 (1H, s), 8.37–8.45 (1H, m)

EXAMPLE 6

The following compounds were obtained according to a similar manner to that of Example 5.

(1) 4-[3-[4-[Bis(4-isobutylphenyl)methoxy]benzoyl]indol-1-yl]butyric acid

NMR ( CDCl$_3$, δ): 0.88 (12H, d, J=7.5 Hz), 1.79–1.98 (2H, m), 2.10–2.30 (2H, m), 2.30–2.50 (6H, m), 4.25 (2H, t, J=7.5 Hz), 6.28 (1H, s), 7.02 (2H, d, J=8.0 Hz), 7.12 (4H, d, J=8 Hz), 7.20–7.45 (7H, m), 7.55 (1H, s), 7.75 (2H, d, J=8 Hz), 8.28–8.40 (1H, m)

(2) 4-[3-[4-[1-(4-Isobutylphenyl)ethoxy]benzoyl]indol-1-yl]butyric acid

NMR (CDCl$_3$, δ): 0.90 (6H, d, J=7.5 Hz), 1.69 (3H, d, J=7.5 Hz), 1.75–1.98 (1H, m), 2.12–2.32 (2H, m), 2.32–2.52 (4H, m), 4.29 (2H, t, J=7.5 Hz), 6.98 (2H, d, J=8 Hz), 7.15 (2H, d, J=8 Hz), 7.25–7.50 (5H, m), 7.89 (2H, d, J=8 Hz), 8.30–8.42 (1H, m)

EXAMPLE 7

A mixture of ethyl 4-[3-(3-hydroxybenzoyl)indol-1-yl]butyrate (984 mg), benzyl 2-bromo-2-(4-isobutylphenyl)acetate (362 mg) and diisopropylethylamine (362 mg) in dichloromethane (10 ml) was stirred at 25° C. for 20 hours, and then refluxed for 70 hours. The mixture was partitioned between ethyl acetate and 1N hydrochloric acid. The organic layer was separated, washed with water and brine, dried over magnesium sulfate, and evaporated. The residue was chromatographed on silica gel (20 g) eluting with a mixture of ethyl acetate and hexane (1:4) to give ethyl 4-[3-[3-[(benzyloxycarbonyl)(4-isobutylphenyl)methoxy]benzoyl]indol-1-yl]butyrate (1.05 g) as an oil.

NMR (CDCl$_3$, δ): 0.91 (6H, d, J=7 Hz), 1.20 (3H, t, J=7 Hz), 1.75–1.98 (1H, m), 2.10–2.37 (4H, m), 2.48 (2H, d, J=7 Hz), 4.10 (2H, q, J=7 Hz), 4.22 (2H, t, J=7 Hz), 5.17 (2H, s), 5.75 (1H, s), 7.08–7.55 (17H, m), 8.40–8.50 (1H, m)

EXAMPLE 8

The following compound was obtained according to a similar manner to that of Example 7.

Ethyl 4-[3-[4-[(benzyloxycarbonyl)(4-isobutylphenyl)methoxy]benzoyl]indol-1-yl]butyrate NMR (CDCl$_3$, δ): 0.91 (6H, d, J=7 Hz), 1.21 (3H, t, J=7 Hz), 1.88 (1H, m), 2.1–2.4 (4H, m), 2.50 (2H, d, J=7 Hz), 4.10 (2H, q, J=7 Hz), 4.25 (2H, t, J=7 Hz), 5.20 (2H, dd, J=11 Hz), 5.37 (1H, s), 7.01 (2H, d, J=9 Hz), 7.20 (2H, d, J=9 Hz), 7.2–7.5 (5H, m), 7.50 (2H, d, J=9 Hz), 7.56 (1H, s), 7.80 (2H, d, J=9 Hz), 8.40 (1H, m)

EXAMPLE 9

A mixture of 3-[3-[2,2-bis(4-isobutylphenyl)ethyl]-benzoyl]indole (442 mg), ethyl 4-bromobutyrate (185 mg) and potassium carbonate (360 mg) in N,N-dimethylformamide (10 ml) was stirred at 20° C. for 4 hours. Ethyl 4-bromobutyrate (185 mg) and potassium carbonate (120 mg) were added, and resulting mixture was stirred at 20° C. for 16 hours. The reaction mixture was poured into a mixture of ethyl acetate and 1N-hydrochloric acid. The organic layer was separated, washed with water and brine, and dried over magnesium sulfate. After evaporation of the solvent, the residue was purified by column chromatography on silica gel (20 g) eluting with a mixture of hexane and ethyl acetate (10:1) to give ethyl 4-[3-[3-[2,2-bis(4-isobutylphenyl)ethyl]-benzoyl]indol-1-yl]butyrate (480 mg) as an oil.

NMR (CDCl$_3$, δ): 0.82 (12H, d, J=7.5 Hz), 1.18–1.48 (3H, m), 1.70–1.94 (2H, m), 2.15–2.50 (8H, m), 3.45 (2H, d, J=7.5 Hz), 4.00–4.35 (5H, m), 6.95–7.70 (16H, m), 8.35–8.49 (1H, m)

EXAMPLE 10

The following compounds were obtained according to a similar manner to that of Example 9.

(1) Ethyl 4-[3-[4-[2,2-bis(4-isobutylphenyl)ethyl]benzoyl]indol-1-yl]butyrate NMR (CDCl$_3$, δ): 0.88 (12H, d, J=7.5 Hz), 1.16–1.32 (3H, m), 1.72–1.92 (2H, m), 2.08–2.58 (8H, m), 3.36–3.54 (4H, m),, 4.03–4.32 (3H, m), 6.98–7.18 (10H, m), 7.29–7.48 (3H, m), 7.51 (1H, s), 7.63 (2H, d, J=8.0 Hz), 8.30–8.41 (1H, m)

(2) Ethyl 4-[3-[3-[1-(3-isobutylphenyl)ethoxy]benzoyl]indol-1-yl]butyrate

NMR (CDCl$_3$, δ): 0.83 (3H, d, J=8 Hz), 0.85 (3H, d, J=8 Hz), 1.20 (3H, t, J=8 Hz), 1.65 (3H, d, J=8 Hz), 1.70–1.92 (1H, m), 2.08–2.23 (2H, m), 2.28 (2H, t, J=8 Hz), 2.44 (2H, d, J=8 Hz), 4.06–4.32 (2H, m), 4.10 (2H, q, J=8 Hz), 5.36 (1H, q, J=8 Hz), 7.00–7.42 (12H, m), 8.36–8.47 (1H, m)

(3) Ethyl 4-[3-[2,3-dimethyl-4-[1-(4-isobutylphenyl)ethoxy]benzoyl]indol-1-yl]butyrate NMR (CDCl$_3$, δ): 0.90 (6H, d, J=8 Hz), 1.20 (3H, t, J=7 Hz), 1.66 (3H, d, J=8 Hz), 1.73–1.97 (1H, m), 2.10–2.25 (2H, m), 2.28 (2H, t, J=8 Hz), 2.30 (3H, s), 2.32 (3H, s), 2.47 (2H, d, J=8 Hz), 4.10 (2H, q, J=8 Hz), 4.18 (2H, t, J=8 Hz), 5.34 (1H, q, J=7 Hz), 6.62 (1H, d, J=10 Hz), 7.10 (1H, d, J=10 Hz), 7.13 (2H, d, J=10 Hz), 7.25–7.43 (6H, m), 8.28–8.38 (1H, m)

(4) Ethyl 4-[3-[3-[bis(4-isobutylphenyl)methylamino]benzoyl]indol-1-yl]-2-butenoate NMR (CDCl$_3$, δ): 0.88 (12H, d, J=8 Hz), 1.30 (3H, t, J=7 Hz), 1.73–1.96 (2H, m), 2.44 (4H, d, J=8 Hz), 3.28 (2H, dd, J=2, 7 Hz), 4.20 (2H, q, J=7 Hz), 5.54 (1H, s), 6.00 (1H, dt, J=14, 7 Hz), 6.73 (1H, broad d, J=8 Hz), 7.0–7.4 (14H, m), 7.45–7.52 (1H, m), 7.76 (1H, s), 8.36–8.44 (1H, m)

(5) Ethyl 4-[3-[3-(10,11-dihydro-5H-dibenz[b,f]azepin-5-ylmethyl)benzoyl]indol-1-yl]butyrate NMR (CDCl$_3$, δ): 1.20 (3H, t, J=8 Hz), 2.08–2.22 (2H, m), 2.30 (2H, t, J=8 Hz), 3.22 (4H, s), 4.08 (2H, q, J=8 Hz), 4.20 (2H, t, J=8 Hz), 5.05 (2H, s), 6.85–6.96 (2H, m), 7.04–7.20 (5H, m), 7.25–7.50 (6H, m), 7.62 (2H, t, J=8 Hz), 7.86 (1H, t, J=1 Hz), 8.35–8.47 (1H, m)

EXAMPLE 11

A mixture of ethyl 4-[3-[3-(chloromethyl)benzoyl]indol-1-yl]butyrate (42.1 mg), 4-isobutylaniline (18.0 mg) and potassium carbonate (30.3 mg) in N,N-dimethylformamide (5 ml) was heated at 50° C. for 20 hours and at 100° C. for 2.5 hours. The mixture was worked up in an usual manner and purified by this layer silica gel chromatography eluting with a mixture of chloroform, hexane and ethyl acetate (6:2:1) to give ethyl 4-[3-[3-[(4-isobutylphenyl)aminomethyl]benzoyl]indol-1-yl]butyrate (23 mg) as an oil.

EXAMPLE 12

The following compound was obtained according to a similar manner to that of Example 11.

Ethyl 4-[3-[3-[(3-isobutylphenyl)aminomethyl]benzoyl]indol-1-yl]butyrate

NMR (CDCl$_3$, δ): 0.85 (6H, d, J=7 Hz), 1.20 (3H, t, J=7.5 Hz), 1.81 (1H, m), 2.1–2.3 (2H, m), 2.3–2.5 (4H, m), 4.08 (2H, q, J=7.5 Hz), 4.0–4.2 (2H, m), 4.44 (2H, s), 6.5–6.7 (3H, m), 7.11 (1H, t, J=7.5 Hz), 7.3–7.6 (6H, m), 7.74 (1H, d, J=7.5 Hz), 7.85 (1H, broad s), 8.4–8.5 (1H, m)

EXAMPLE 13

A mixture of ethyl 4-[3-[3-(chloromethyl)benzoyl]indol-1-yl]butyrate (42.5 mg) and 4-isobutylphenol (18.3 mg) and potassium carbonate (30.6 mg) in N,N-dimethylformamide (3 ml) was heated at 100° C. for 1 hour and 50° C. for 10 hours. The mixture was worked up in an usual manner and purified by thin layer silica gel chromatography eluting with a mixture of ethyl acetate and hexane (1:2) to give ethyl 4-[3-[3-(4-isobutylphenoxymethyl)benzoyl]indol-1-yl]butyrate (46.7 mg) as an oil.

NMR (CDCl$_3$, δ): 0.89 (6H, d, J=7 Hz), 1.21 (3H, t, J=7 Hz), 1.82 (1H, m), 2.1–2.4 (4H, m), 2.42 (2H, d, J=7 Hz), 4.10 (2H, q, J=7 Hz), 4.24 (2H, t, J=7 Hz), 5.14 (2H, s), 6.91 (2H, d, J=8 Hz), 7.08 (2H, d, J=8 Hz), 7.3–7.5 (3H, m), 7.5–7.6 (2H, m), 7.65 (1H, d, J=7.5 Hz), 7.78 (1H, d, J=7.5 Hz), 7.90 (1H, s), 8.4–8.5 (1H, m)

EXAMPLE 14

The following compound was obtained according to a similar manner to that of Example 13.

Ethyl 4-[3-[3-(3-isobutylphenoxymethyl)benzoyl]indol-1-yl]butyrate

NMR (CDCl$_3$, δ): 0.89 (6H, d, J=7 Hz), 1.20 (3H, t, J=7 Hz), 1.85 (1H, m), 2.1–2.4 (4H, m), 2.44 (2H, d, J=7 Hz), 4.10 (2H, q, J=7 Hz), 4.22 (2H, t, J=7 Hz), 5.15 (2H, s), 6.7–6.9 (3H, m), 7.1–7.3 (1H, m), 7.3–7.6 (5H, m), 7.65 (1H, d, J=7.5 Hz), 7.78 (1H, d, J=7.5 Hz), 7.80 (1H, s), 8.4–8.5 (1H, m)

EXAMPLE 15

A mixture of ethyl 4-[3-(4-hydroxybenzoyl)indol-1-yl]butyrate (0.50 g), 1-bromo-2,2-dimethyl-1-(4-isobutylphenyl)propane (0.74 g) and potassium carbonate (0.59 g) in N,N-dimethylformamide (10 ml) was stirred at 60° C. for 20 hours. The reaction mixture was filtered, and the filtrate was poured into a mixture of ethyl acetate and 0.5N hydrochloric acid. The organic layer was separated, washed with water, and dried over magnesium sulfate. After evaporation of the solvent, the residue was purified by column chromatography on silica gel eluting a mixture of n-hexane and ethyl acetate (5:1) to give ethyl 4-[3-[4-[2,2-dimethyl-1-(4-isobutylphenyl)-propyloxy]benzoyl]indol-1-yl]butyrate (376 mg) as an oil.

NMR (CDCl$_3$, δ): 0.88 (6H, d, J=7 Hz), 1.03 (9H, s), 1.20 (3H, t, J=7.5 Hz), 1.74–1.96 (1H, m), 2.10–2.35 (4H, m), 2.45 (2H, d, J=7 Hz), 4.10 (2H, q, J=7.5 Hz), 4.22 (2H, t, J=7 Hz), 4.81 (1H, s), 6.88 (2H, d, J=9 Hz), 7.08 (2H, d, J=8.5 Hz), 7.20–7.45 (5H, m), 7.51 (1H, s), 7.70 (2H, d, J=9 Hz), 8.31–8.41 (1H, m)

EXAMPLE 16

The following compound was obtained according to a similar manner to that of Example 15.

Ethyl 4-[3-[4-[1-(4-isobutylphenyl)propoxy]benzoyl]indol-1-yl]butyrate

NMR (CDCl$_3$, δ) : 0.89 (6H, d, J=7 Hz), 1.02 (3H, t, J=7.5 Hz), 1.20 (3H, t, J=7.5 Hz), 1.75–2.10 (3H, m), 2.15–2.35 (4H, m), 2.46 (2H, d, J=7 Hz), 4.10 (2H, q, J=7.5 Hz), 4.23 (2H, t, J=7 Hz), 5.10 (1H, t, J=7 Hz), 6.93 (2H, d, J=9 Hz), 7.12 (2H, d, J=8.5 Hz), 7.22–7.45 (5H, m), 7.53 (1H, s), 7.75 (2H, d, J=9 Hz), 8.32–8.40 (1H, m)

EXAMPLE 17

A solution of ethyl 4-[3-[3,5-bis(tertbutoxycarbonylamino)benzoyl]indol-1-yl]butyrate ( 300 mg) in N,N-dimethylformamide (5 ml) was added to a suspension of sodium hydride (60% dispersion in mineral oil, 54 mg) in N,N-dimethylformamide (5 ml) at 0° C. The mixture was stirred at 0° C. for 30 minutes, and a solution of 4-isobutylbenzyl chloride (38.8 mg) in N,N-dimethylformamide (5 ml) was added at 0° C. The reaction mixture was stirred at 0° C. for 3 hours, and poured into a mixture of 0.1N hydrochloric acid and ethyl acetate. The organic layer was separated, washed with water, aqueous solution of sodium bicarbonate and brine in successively. After dryness over magnesium sulfate and evaporation of the solvent, the residue was chromatographed on silica gel (25 g) eluting with a mixture of ethyl acetate and hexane (1:4) to give ethyl 4-[3-[3,5-bis[N-( 4-isobutylbenzyl )-N-tert-butoxycarbonylamino] benzoyl]indol-1-yl]butyrate (155 mg) as an oil.

NMR (CDCl$_3$, δ) : 0.86 (12H, d, J=7 Hz), 1.22 (2H, t, J=7.5 Hz), 1.40 (18H, s), 1.7–1.9 (1H, m), 2.1–2.4 (4H, m), 2.42 (4H, d, J=7 Hz), 4.11 (2H, q, J=7.5 Hz), 4.21 (2H, t, J=6 Hz), 4.76 (4H, s), 7.0–7.2 (9H, m), 7.3–7.5 (3H, m), 7.5–7.7 (3H, m), 8.4–8.5 (1H, m)

EXAMPLE 18

1-(3-Dimethylaminopropyl)-3-ethylcarbodiimide hydrochloride (30 mg) was added to a mixture of ethyl 4-[3-[4-[(carboxy)(4-isobutylphenyl)methoxy]benzoyl]indol-1-yl]butyrate (70 mg), 4-isobutylaniline (20 mg) and 1-hydroxybenzotriazole (20 mg) in dichloromethane (3 ml). After stirred at 25° C. for 4 hours, the mixture was partitioned between ethyl acetate and 1N hydrochloric acid. The organic layer was separated, washed with water and brine, and dried over magnesium sulfate. After evaporation of the solvent, the residue was chromatographed on silica gel (5 g) eluting with chloroform to give ethyl 4-[3-[4-[(4-isobutylphenyl)[(4-isobutylphenyl)carbamoyl]methoxy]benzoyl]indol-1-yl]butyrate (85 mg) as an oil.

NMR (CDCl$_3$, δ) : 0.8–1.0 (12H, m), 1.20 (3H, t, J=7 Hz), 1.83 (2H, m), 2.1–2.6 (8H, m), 4.10 (2H, q, J=7 Hz), 4.25 (2H, t, J=7 Hz), 5.72 (1H, s), 7.0–7.6 (14H, m), 7.82 (2H, d, J=9 Hz), 8.3–8.5 (2H, m)

EXAMPLE 19

The following compounds were obtained according to a similar manner to that of Example 18.

(1) Ethyl 4-[3-[4-[(4-isobutylphenyl)(phenylcarbamoyl)methoxy]benzoyl]indol-1-yl]butyrate NMR (CDCl$_3$, δ) : 0.86 (6H, d, J=7 Hz), 1.21 (3H, J=7 Hz), 1.85 (1H, m), 2.1–2.4 (4H, m), 2.48 (2H, d, J=7 Hz), 4.10 (2H, q, J=7 Hz), 4.25 (2H, t, J=7 Hz), 5.72 (1H, s), 7.1–7.6 (15H, m), 7.83 (2H, d, J=9 Hz), 8.36 (2H, m)

(2) Ethyl 4-[3-[4-[(4-isobutylphenyl)(tert-butylcarbamoyl)methoxy]benzoyl]indol-1-yl]butyrate NMR (CDCl$_3$, δ) : 0.90 (6H, d, J=7 Hz), 1.21 (3H, t, J=7 Hz), 1.46 (9H, s), 1.87 (1H, m), 2.1–2.5 (4H, m), 2.47 (2H, d, J=7 Hz), 4.11 (2H, q, J=7 Hz), 4.26 (2H, t, J=7 Hz), 5.48 (1H, s), 6.45 (1H, s), 7.04 (2H, d, J=9 Hz), 7.17 (2H, d, J=9 Hz), 7.2–7.5 (3H, m), 7.42 (2H, d, J=9 Hz), 7.55 (1H, s), 7.83 (2H, d, J=9 Hz), 8.37 (1H, m)

(3) Ethyl 4-[3-[4-[(4-isobutylphenyl)(N,N-dimethylcarbonyl)methoxy]benzoyl]indol-1-yl]butyrate NMR (CDCl$_3$, δ) : 0.8–1.0 (9H, m), 1.13 (3H, t, J=7 Hz), 1.20 (3H, t, J=7 Hz), 1.38 (1H, m), 2.1–2.4 (4H, m), 2.49 (2H, d, J=7 Hz), 3.2–3.5 (4H, m), 4.12 (2H, q, J=7 Hz), 4.26 (2H, t, J=7 Hz), 5.90 (1H, s), 7.10 (2H, d, J=9 Hz), 7.20 (2H, d, J=9 Hz), 7.2–7.4 (3H, m), 7.45 (2H, d, J=9 Hz), 7.58 (1H, s), 7.84 (2H, d, J=9 Hz), 8.40 (1H, m)

(4) Ethyl 4-[3-[3-[(4-isobutylphenyl)][(4-isobutylphenyl)carbamoyl]methylamino]benzoyl]indol-1-yl]butyrate NMR (CDCl$_3$, δ) : 0.88 (12H, d, J=7 Hz), 1.20 (3H, t, J=7 Hz), 1.7–2.0 (2H, m), 2.1–2.4 (4H, m), 2.4–2.5 (4H, m), 4.0–4.2 (4H, m), 4.95 (1H, s), 6.91 (1H, m), 7.0–7.5 (14H, m), 7.53 (1H, s), 8.4–8.5 (1H, m), 8.72 (1H, s)

(5) Ethyl-4-[3-[3-[(4-isobutylphenyl)(phenylcarbamoyl)methylamino]benzoyl]indol-1-yl]butyrate NMR (CDCl$_3$, δ) : 0.89 (6H, d, J=7 Hz), 1.20 (3H, t, J=7 Hz), 1.7–2.0 (1H, m), 2.1–2.4 (4H, m), 2.45 (2H, d, J=7 Hz), 4.0–4.2 (4H, m), 4.95 (1H, s), 6.93 (1H, m), 7.0–7.5 (15H, m), 7.53 (1H, s), 8.4–8.5 (1H, m), 8.75 (1H, s)

(6) Ethyl 4-[3-[3[(4-isobutylphenyl)(tert-butylcarbamoyl)methylamino]benzoyl]indol-1-yl]butyrate NMR (CDCl$_3$, δ) : 0.86 (6H, d, J=7 Hz), 1.20 (3H, t, J=7 Hz), 1.29 (9H, s), 1.83 (1H, m), 2.1–2.4 (4H, m), 2.45 (2H, d, J=7 Hz), 4.08 (2H, q, J=7 Hz), 4.25 (2H, m), 4.80 (1H, s), 6.38 (1H, s), 6.93 (1H, m), 7.0–7.5 (10H, m), 7.62 (1H, s), 8.4–8.5 (1H, m)

(7) Ethyl 4-[3-[3-[(4-isobutylphenyl)(diethylcarbamoyl)methylamino]benzoyl]indol-1-yl]butyrate NMR (CDCl$_3$, δ) : 0.85 (6H, d, J=7 Hz), 0.92 (3H, t, J=7 Hz), 1.08 (3H, t, J=7 Hz), 1.81 (1H, m), 2.1–2.4 (4H, m), 2.42 (2H, d, J=7 Hz), 3.2–3.5 (4H, m), 4.08 (2H, q, J=7 Hz), 4.23 (2H, m), 5.30 (1H, s), 6.88 (1H, m), 7.0–7.5 (10H, m), 7.62 (1H, s), 8.4–8.5 (1H, m)

(8) Ethyl 4-[3-[3-[(4-isobutylphenyl)][(4-isobutylphenyl)carbamoyl]methoxy]benzoyl]indol-1-yl]butyrate NMR (CDCl$_3$, δ) : 0.82–0.95 (12H, m), 1.19 (3H, t, J=7 Hz), 1.70–1.95 (2H, m), 2.08–2.35 (4H, m), 2.38–2.50 (4H, m), 4.08 (2H, q, J=7 Hz), 4.19 (2H, t, J=7 Hz), 5.70 (1H, s), 7.05–7.22 (5H, m), 7.29–7.56 (11H, m), 8.36–8.48 (1H, m)

(9) Ethyl-4-[3-[3-[(4-isobutylphenyl)(phenylcarbamoyl)methoxy]benzoyl]indol-1-yl]butyrate NMR (CDCl$_3$, δ) : 0.88 (6H, d, J=7 Hz), 1.18 (3H, t, J=7 Hz), 1.72–1.96 (2H, m), 2.08–2.35 (4H, m), 2.46 (2H, t, J=7 Hz), 4.08 (2H, q, J=7 Hz), 4.18 (2H, t, J=7 Hz), 5.71 (1H, s), 7.08–7.62 (17H, m), 8.38–8.50 (2H, m)

(10) Ethyl 4-[3-[3-[(t-butylcarbamoyl)(4-isobutylphenyl)methoxy]benzoyl]indol-1-yl]butyrate NMR (CDCl$_3$, δ) : 0.88 (6H, d, J=7 Hz), 1.20 (3H, t, J=7 Hz), 1.35 (9H, s), 1.75–1.97 (1H, m), 2.12–2.37 (4H, m), 2.45 (2H, d, J=7 Hz), 4.09 (2H, q, J=7 Hz), 4.25 (2H, t, J=7 Hz), 5.46 (1H, s), 6.52 (1H, s), 7.07–7.19 (3H, m), 7.30–7.48 (8H, m), 7.51 (1H, s), 8.37–8.47 (1H, m)

(11) Ethyl 4-[3-[3-(diethylcarbamoyl)(4-isobutylphenyl)methoxy]benzoyl]indol-1-yl]butyrate NMR (CDCl$_3$, δ) : 0.83–0.98 (9H, m), 1.08 (3H, t, J=7 Hz), 1.21 (3H, t, J=7 Hz), 1.75–1.98 (1H, m), 2.12–2.38 (4H, m), 2.48 (2H, d, J=7 Hz), 3.26–3.45 (4H, m), 4.10 (2H, q, J=7 Hz), 4.27 (2H, t, J=7 Hz), 5.92 (1H, s), 7.13–7.50 (11H, m), 7.62 (1H, s), 8.40–8.50 (1H, m)

EXAMPLE 20

Ethyl 4-[3-4-[(benzyloxycarbonyl)(4-isobutylphenyl)methoxy]benzoyl]indol-1-yl]butyrate (0.36 g) was dissolved in a mixture of 1,4-dioxane (10 ml) and ethanol (10 ml), and 10% palladium on carbon (0.2 g) was added. The mixture was stirred under hydrogen atmosphere at 25° C. for 2 hours. Removal of the catalyst and evaporation of the solvent gave ethyl 4-[3-[4-[(carboxy)(4-isobutylphenyl)methoxy]benzoyl]indol-1-yl]butyrate (0.23. g) as powder.

NMR (CDCl$_3$, δ) : 0.90 (6H, d, J=7 Hz), 1.88 (1H, m), 2.1–2.4 (4H, m), 2.50 (2H, d, J=7 Hz), 4.29 (2H, t, J=7 Hz), 5.70 (1H, s), 7.06 (2H, d, J=9 Hz), 7.20 (2H, d, J=9 Hz), 7.2–7.5 (3H, m), 7.52 (2H, d, J=9 Hz), 7.58 (1H, s), 7.82 (2H, d, J=9 Hz), 8.38 (1H, m).

EXAMPLE 21

The following compounds were obtained according to a similar manner to that of Example 20.

(1) Ethyl 4-[3-[3-[(carboxy)(4-isobutylphenyl)methylamino]benzoyl]indol-1-yl]butyrate NMR (CDCl$_3$, δ) : 0.88 (6H, d, J=7 Hz), 1.21 (3H, t, J=7 Hz), 1.35 (1H, m), 4.1–4.3 (2H, m), 5.06 (1H, s), 6.75–6.9 (1H, m), 7.0–7.5 (10H, m), 7.60 (1H, s), 8.4–8.5 (1H, m)

(2) Ethyl 4-[3-[3-[(carboxy)(4-isobutylphenyl)methoxy]benzoyl]indol-1-yl]butyrate NMR (CDCl$_3$, δ) : 0.90 (6H, d, J=7 Hz), 1.22 (3H, t, J=7 Hz), 1.76–1.98 (1H, m), 2.15–2.36 (2H, m), 2.38–2.55 (4H, m), 4.02–4.36 (4H, m), 5.62 (1H, s), 7.16–7.60 (12H, m), 8.46–8.56 (1H, m)

EXAMPLE 22

To a solution of ethyl 3-[3-[3-[bis(4-isobutylphenyl)methylamino]benzoyl]indol-1-yl]propionate (507 mg) in a mixture of 1,4-dioxane (8 ml) and methanol (2 ml) was added 1N aqueous sodium hydroxide (2 ml), and the mixture was stirred at 25° C. for 5 hours. After evaporation of the organic solvent, the residue was acidified (pH 2) with 1N hydrochloric acid, and extracted with ethyl acetate. The extract was washed with water and dried over magnesium sulfate. After evaporation of the solvent, the residue was chromatographed on silica gel (20 g) eluting with chloroform to give 3-[3-[3-[bis(4-isobutylphenyl)methylamino]benzoyl]indol-1-yl]propionic acid (375 mg) as an oil.

NMR (CDCl$_3$, δ) : 0.88 (12H, d, J=7 Hz), 1.82 (2H, m), 2.42 (4H, d, J=7 Hz), 2.85 (2H, t, J=6 Hz), 4.38 (2H, t, J=6 Hz), 5.52 (1H, s), 6.71 (1H, d, J=7.5 Hz), 7.0–7.4 (6H, m), 7.08 (4H, d, J=8 Hz), 7.25 (4H, d, J=8 Hz), 7.52 (1H, s), 8.4–8.5 (1H, m)

EXAMPLE 23

The following compounds were obtained according to a similar manner to that of Example 22.

(1) 5-[3-[3-[Bis(4-isobutylphenyl)methylamino]benzoyl]indol-1-yl]valeric acid

NMR (CDCl$_3$, δ) : 0.87 (12H, d, J=7 Hz), 1.5–1.7 (2H, m), 1.7–2.0 (4H, m), 2.34 (2H, t, J=6 Hz), 2.44 (4H, d, J=7 Hz), 4.10 (2H, t, J=6 Hz), 5.5 (1H, s), 6.71 (1H, broad d, J=7.5 Hz), 7.0–7.4 (6H, m), 7.10 (4H, d, J=8 Hz), 7.25 (4H, d, J=8 Hz), 7.48 (1H, s), 8.4–8.5 (1H, m)

(2) 4-[3-[3-[Bis(4-isobutylphenyl)methylamino]benzoyl]indol-1-yl]butyric acid

NMR (CDCl$_3$, δ) : 0.88 (12H, d, J=7 Hz), 1.82 (2H, m), 2.12 (2H, quin, J=6 Hz), 2.32 (2H, t, J=6 Hz), 2.42 (4H, d, J=7 Hz), 3.96 (1H, s), 4.12 (1H, t, J=6 Hz), 5.39 (1H, s), 6.34 (1H, dd, J=1, 7.5 Hz), 6.49 (1H, broad s), 6.61 (1H, d, J=7.5 Hz), 6.76 (1H, s), 6.9–7.4 (4H, m), 7.05 (4H, d, J=8 Hz), 7.20 (4H, d, J=8 Hz), 7.48 (1H, d, J=7.5 Hz)

(3) 4-[3-[3-[(4-Isobutylbenzyl)amino]benzoyl]indol-1-yl]butyric acid

NMR (CDCl$_3$, δ) : 0.88 (6H, d, J=7 Hz), 1.84 (1H, m), 2.17 (2H, quin, J=7 Hz), 2.35 (2H, t, J=7 Hz), 2.45 (2H, d, J=7 Hz), 4.21 (2H, t, J=7 Hz), 4.33 (2H, s), 6.82 (1H, d, J=7.5 Hz), 7.0–7.4 (10H, m), 7.55 (1H, s), 8.4–8.5 (1H, m)

(4) 4-[3-[3-[(4-Isobutylphenyl)aminomethyl]benzoyl]indol-1-yl]butyric acid

NMR (CDCl$_3$, δ) : 0.88 (6H, d, J=7 Hz), 1.80 (1H, m), 2.1–2.3 (4H, m), 2.39 (2H, d, J=7 Hz), 4.27 (2H, t, J=6 Hz), 4.37 (2H, s), 6.76 (2H, d, J=8 Hz), 7.02 (2H,

(5)
4-[3-[3-[(3-Isobutylphenyl)aminomethyl]benzoyl]indol-1-yl]butyric acid

NMR (CDCl$_3$, δ) : 0.88 (6H, d, J=7 Hz), 1.82 (1H, m), 2.1–2.3 (4H, m), 2.39 (2H, d, J=7 Hz), 4.23 (2H, t, J=6 Hz), 4.39 (2H, s), 6.5–6.7 (3H, m), 7.13 (1H, t, J=7.5 Hz), 7.2–7.6 (6H, m), 7.76 (1H, d, J=7.5 Hz), 7.88 (1H, broad s), 8.4–8.5 (1H, m)

(6)
4-[3-[3,5-Bis[N-(4-isobutylbenzyl)-N-tert-butoxycarbonylamino]benzoyl]indol-1-yl]butyric acid NMR (CDCl$_3$, δ) : 0.86 (12H, d, J=7 Hz), 1.39 (18H, s), 1.81 (2H, m), 2.1–2.4 (4H, m), 2.42 (4H, d, J=7 Hz), 4.23 (2H, t, J=6 Hz), 4.75 (4H, s), 7.0–7.2 (9H, m), 7.2–7.5 (3H, m), 7.49 (2H, d, J=2 Hz), 7.59 (1H, s), 8.4–8.5 (1H, m)

(7)
4-[3-[5-[Bis(4-isobutylphenyl)methylamino]-2-furoyl]indol-1-yl]butyric acid NMR (CDCl$_3$, δ) : 0.81 (12H, d, J=7 Hz), 1.71 (2H, m), 1.9–2.0 (2H, m), 2.0–2.2 (2H, m), 2.30 (4H, d, J=7 Hz), 4.30 (2H, m), 6.12 (1H, d, J=8 Hz), 6.76 (4H, d, J=8 Hz), 7.00 (4H, d, J=8 Hz), 7.3–7.5 (5H, m), 7.8–7.9 (1H, m), 7.93 (1H, s), 8.5–8.6 (1H, m)

(8)
4-[3-[3-[Bis(4-isobutylphenyl)methylamino]benzoyl]indol-1-yl]butyric acid NMR (CDCl$_3$, δ) : 0.89 (12H, d, J=7.5 Hz), 1.85 (2H, m), 2.17 (2H, m), 2.28–2.50 (6H, m), 4.20 (2H, t, J=7.5 Hz), 5.51 (1H, s), 6.78 (1H, broad d), 7.00–7.48 (15H, m), 8.45 (1H, m)

(9)
4-[3-[3-[2,2-Bis(4-isobutylphenyl)ethyl]benzoyl]indol-1-yl]butyric acid

NMR (CDCl$_3$, δ): 0.82 (12H, d, J=7.5 Hz), 1.65–1.96 (2H, m), 2.10–2.30 (2H, m), 2.30–2.45 (6H, m), 3.39 (2H, d, J=7.5 Hz), 4.15–4.32 (3H, m), 7.00 (4H, d, J=8.0 Hz), 7.10 (4H, d, J=8.0 Hz), 7.18–7.48 (6H, m), 7.48–7.62 (2H, m), 8.30–8.42 (1H, m)

(10)
4-[3-[4-[2,2-Bis(4-isobutylphenyl)ethyl]benzoyl]indol-1-yl]butyric acid NMR (CDCl$_3$, δ) : 0.88 (12H, d, J=7.5 Hz), 1.70–1.92 (2H, m), 2.10–2.30 (2H, m), 2.30–2.50 (6H, m), 3.38 (2H, d, J=7.5 Hz), 4.10–4.34 (3H, m), 6.93–7.18 (10H, m), 7.28–7.45 (3H, m), 7.50 (1H, s), 7.62 (2H, d, J=8.0 Hz), 8.30–8.40 (1H, m)

(11)
4-[3-[3-[Bis(4-isobutylbenzyl)amino]benzoyl]indol-1-yl]butyric acid

NMR (CDCl$_3$, δ) : 0.89 (12H, d, J=7 Hz), 1.84 (2H, m), 2.11 (2H, quin, J=7 Hz), 2.30 (2H, t, J=7 Hz), 2.44 (4H, d, J=7 Hz), 4.10 (2H, t, J=7 Hz), 4.66 (4H, s), 6.91 (1H, broad d, J=7.5 Hz), 7.1–7.5 (15H, m), 8.4–8.5 (1H, m)

(12)
4-[3-[3-[(4-Isobutylphenoxy)methyl]benzoyl]indol-1-yl]butyric acid

NMR (CDCl$_3$, δ) : 0.88 (6H, d, J=7 Hz), 1.81 (1H, m), 2.19 (2H, quin, J=7 Hz), 2.3–2.5 (4H, m), 4.24 (2H, t, J=7 Hz), 5.13 (2H, s), 6.89 (2H, d, J=8 Hz), 7.06 (2H, d, J=8 Hz), 7.3–7.5 (3H, m), 7.5–7.6 (2H, m), 7.62 (1H, broad d, J=7.5 Hz), 7.77 (1H, broad d, J=7.5 Hz), 7.88 (1H, broad s), 8.4–8.5 (1H, m)

(13)
4-[3-[3-[(3-Isobutylphenoxy)methyl]benzoyl]indol-1-yl]butyric acid

NMR (CDCl$_3$, δ) : 0.88 (6H, d, J=7 Hz), 1.84 (1H, m), 2.18 (2H, quin, J=7 Hz), 2.36 (2H, t, J=7 Hz), 2.44 (2H, d, J=7 Hz), 4.22 (2H, t, J=7 Hz), 5.14 (2H, s), 6.7–6.9 (3H, m), 7.1–7.3 (1H, m), 7.3–7.6 (5H, m), 7.63 (1H, d, J=7.5 Hz), (1H, d, J=7.5 Hz), 7.88 (1H, broad s), 8.4–8.5 (1H, m)

(14)
4-[3-[4-[2,2-Dimethyl-1-(4-isobutylphenyl)propyloxy]benzoyl]indol-1-yl]butyric acid NMR (CDCl$_3$, δ) : 0.87 (6H, d, J=7 Hz), 1.02 (9H, s), 1.83 (1H, m), 2.18 (2H, m), 2.38 (2H, m), 2.43 (2H, d, J=7 Hz), 4.21 (2H, t, J=7 Hz), 4.79 (1H, s), 6.88 (2H, d, J=8 Hz), 7.07 (2H, d, J=8 Hz), 7.21 (2H, d, J=8 Hz), 7.2–7.5 (3H, m), 7.52 (1H, s), 7.70 (2H, d, J=8 Hz), 8.32 (1H, m)

(15)
4-[3-[4-[1-(4-Isobutylphenyl)propoxy]benzoyl]indol-1-yl]butyric acid

NMR (CDCl$_3$, δ) : 0.88 (6H, d, J=7 Hz), 1.00 (3H, t, J=7.5 Hz), 1.75–2.10 (3H, m), 2.12–2.28 (2H, m), 2.32–2.50 (4H, m), 4.23 (2H, t, J=7 Hz), 5.08 (1H, t, J=7 Hz), 6.92 (2H, d, J=9 Hz), 7.11 (2H, d, J=8.5 Hz), 7.13–7.45 (5H, m), 7.54 (1H, s), 7.73 (2H, d, J=9 Hz), 8.38–8.48 (1H, m)

(16)
4-[3-[3-[1-(3-Isobutylphenyl)ethoxy]benzoyl]indol-1-yl]butyric acid

NMR (DMSO-d$_6$, δ) : 0.70 (3H, d, J=8 Hz), 0.74 (3H, d, J=8 Hz), 1.60 (3H, d, J=8 Hz), 1.62–1.80 (1H, m), 1.90–2.10 (2H, m), 2.40 (2H, d, J=8 Hz), 4.30 (2H, m), 5.58 (1H, q, J=8 Hz), 7.00–7.45 (10H, m), 7.75 (1H, d, J=8 Hz), 7.87 (1H, s), 8.24 (1H, dd, J=2, 8 Hz)

(17)
4-[3-[2,3-Dimethyl-4-[1-isobutylphenyl)ethoxy]benzoyl]indol-1-yl]butyric acid NMR (DMSO-d$_6$, δ) : 0.85 (6H, d, J=8 Hz), 1.58 (3H, J=7 Hz), 1.70–2.05 (3H, m), 2.18 (3H, s), 2.19–2.23 (2H, m), 2.24 (3H, s), 2.44 (2H, d, J=8 Hz), 4.24 (2H, q, J=8 Hz), 5.52 1H, q, J=7 Hz), 6.78 (1H, d, J=10 Hz), 7.10 (1H, d, J=10 Hz), 7.16 (2H, d, J=10 Hz), 7.20–7.32 (2H, m), 7.45 (2H, d, J=10 Hz), 7.61 (1H, d, J=10 Hz), 7.61 (1H, s), 8.18 (1H, dd, J=2, 10 Hz)

(18)
4-[3-[4-[(4-Isobutylphenyl)[(4-isobutylphenyl)carbamoyl]methoxy]benzoyl]indol-1-yl]butyric acid NMR (CDCl$_3$, δ) : 8.3–8.4 (2H, m), 7.83 (2H, d, J=9 Hz), 7.0–7.6 (14H, m), 5.71 (1H, s), 4.25 (2H, t, J=7 Hz), 2.1–2.6 (8H, m), 1.83 (2H, m), 0.8–1.0 (12H, m)

(19)

4-[3-[4-[(4-Isobutylphenyl)(phenylcarbamoyl)methoxy]benzoyl]indol-1-yl]butyric acid NMR (CDCl$_3$, δ) : 0.90 (6H, d, J=7 Hz), 1.85 (1H, m), 2.1-2.5 (4H, m), 2.45 (2H, d, J=7 Hz), 4.25 (2H, t, J=7 Hz), 5.73 (1H, s), 7.0-7.6 (15H, m), 7.82 (2H, d, J=9 Hz), 8.38 (2H, m)

(20)

4-[3-[4-[(4-Isobutylphenyl)(tert-butylcarbamoyl)methoxy]benzoyl]indol-1-yl]butyric acid NMR (CDCl$_3$, δ) : 0.90 (6H, d, J=7 Hz), 1.35 (9H, s), 1.86 (1H, m), 2.1-2.5 (4H, m), 2.48 (2H, d, J=7 Hz), 4.28 (2H, t, J=7 Hz), 5.50 (1H, s), 6.45 (1H, s), 7.05 (2H, d, J=9 Hz), 7.17 (2H, d, J=9 Hz), 7.3-7.5 (3H, m), 7.42 (2H, d, J=9HZ) , 7.55 (1H, s), 7.83 (2H, d, J=9 Hz), 8.37 (1H, m)

(21)

4-[3-[4-[(4-Isobutylphenyl)(diethylcarbamoyl)methoxy]benzoyl]indol-1-yl]butyric acid NMR (CDCl$_3$, δ) : 0.8-1.0 (9H, m), 1.10 (3H, t, J=7 Hz), 1.85 (1H, m), 2.1-2.4 (4H, m), 2.50 (2H, d, J=7 Hz), 3.2-3.5 (4H, m), 4.26 (2H, t, J=7 Hz), 5.96 (1H, s), 7.10 (2H, d, J=9 Hz), 7.18 (2H, d, J=9 Hz), 7.2-7.4 (3H, m), 7.43 (2H, d, J=9 Hz), 7.55 (1H, s), 7.82 (2H, d, J=9 Hz), 8.39 (1H, m)

(22)

4-[3-[3-[(4-Isobutylphenyl)[(4-isobutylphenyl)carbamoyl]methylamino]benzoyl]indol-1-yl]butyric acid NMR (DMSO-d$_6$, δ) : 0.85 (12H, m), 1.7-1.9 (2H, m), 1.9-2.1 (2H, m), 2.1-2.3 (2H, m), 2.3-2.5 (4H, m), 4.1-4.3 (2H, m), 5.25 (1H, d, J=7 Hz), 6.60 (1H, d, J=7 Hz), 6.9-7.7 (14H, m), 7.86 (1H, s), 8.27 (1H, d, 7 Hz), 10.30 (1H, s)

(23)

4-[3-[3-[(4-Isobutylphenyl)(phenylcarbamoyl)methylamino]benzoyl]indol-1-yl]butyric acid NMR (DMSO-d$_6$, δ) : 0.85 (6H, m), 1.72 (1H, m), 1.9-2.1 (2H, m), 2.1-2.3 (2H, m), 2.42 (2H, d, J=7 Hz), 4.1-4.3 (2H, m), 5.25 (1H, d, J=7 Hz), 6.60 (1H, d, J=7 Hz), 6.9-7.7 (15H, m), 7.88 (1H, s), 8.27 (1H, d, J=7 Hz), 10.38 (1H, s)

(24)

4-[3-[3-[(4-Isobutylphenyl)(tert-butylcarbamoyl)methylamino]benzoyl]indol-1-yl]butyric acid NMR (CDCl$_3$, δ) : 8.48 (1H, m), 7.64 (1H, s), 7.1-7.5 (10H, m), 6.83 (1H, m), 4.87 (1H, s), 4.2-4.4 (2H, m), 2.49 (2H, d, J=7 Hz), 2.1-2.4 (4H, m), 1.85 (1H, m), 1.30 (9H, s), 0.89 (6H, d, J=7 Hz)

(25)

4-[3-[3-[(4-Isobutylphenyl)(diethylcarbamoyl)methylamino]benzoyl]indol-1-yl]butyric acid NMR (CDCl$_3$, δ) : 0.85 (6H, d, J=7 Hz), 1.02 (3H, t, J=7 Hz), 1.23 (3H, t, J=7 Hz), 1.82 (1H, m), 2.0-2.4 (4H, m), 2.43 (2H, d, J=7 Hz), 3.1-3.7 (4H, m), 4.3-4.5 (2H, m), 5.43 (1H, s), 6.93 (1H, m), 7.1-7.5 (10H, m), 7.58 (1H, s), 8.48 (1H, m)

(26)

4-[3-[3-[(Cyano)(4-isobutylphenyl)methylamino]benzoyl]indol-1-yl]butyric acid

NMR (CDC$_3$, δ) : 0.90 (6H, d, J=7 Hz), 1.87 (1H, m), 2.1-2.5 (4H, m), 2.50 (2H, d, J=7 Hz), 4.26 (2H, t, J=7 Hz), 5.43 (1H, s), 6.93 (1H, m), 7.1-7.5 (10H, m), 7.75 (1H, s), 8.45 (1H, m)

(27)

4-[3-[3-[(4-Isobutylphenyl)[(4-isobutylphenyl)carbamoyl]methoxy]benzoyl]indol-1-yl]butyric acid NMR (CDCl$_3$, δ) : 0.80-0.94 (12H, m), 1.68-1.95 (2H, m), 2.22-2.36 (4H, m), 2.38-2.50 (4H, m), 4.28 (2H, t, J=7 Hz), 5.91 (1H, s), 7.04-7.60 (16H, m), 8.36-8.50 (1H, m)

(28)

4-[3-[3-[(4-Isobutylphenyl)(phenylcarbamoyl)methoxy]benzoyl]indol-1-yl]butyric acid NMR (CDCl$_3$, δ) : 0.88 (6H, d, J=7 Hz), 1.72-1.95 (1H, m), 2.10-2.37 (6H, m), 2.45 (2H, d, J=7 Hz), 4.26 (2H, t, J=7 Hz), 5.88 (1H, s), 7.08-7.60 (17H, m), 8.40-8.50 (2H, m)

(29)

4-[3-[3-[(t-Butylcarbamoyl)(4-isobutylphenyl)methoxy]benzoyl]indol-1-yl]butyric acid NMR (CDCl$_3$, δ) : 0.88 (6H, d, J=7 Hz), 1.32 (9H, s), 1.74-1.95 (1H, m), 2.18-2.38 (4H, m), 2.45 (2H, d, J=7 Hz), 4.39 (2H, t, J=7 Hz), 5.81 (1H, s), 6.53 (1H, s), 7.10-7.20 (3H, m), 7.30-7.53 (8H, m), 7.63 (1H, s), 8.46-8.56 (1H, m)

(30)

4-[3-[3-[(Diethylcarbamoyl)(4-isobutylphenyl)methoxy]benzoyl]indol-1-yl]butyric acid NMR (CDCl$_3$, δ) : 0.82-1.02 (9H, m), 1.10 (3H, t, J=7 Hz), 1.72-1.96 (1H, m), 2.10-2.37 (4H, m), 2.45 (2H, d, J=7 Hz), 3.28-3.50 (4H, m), 4.40 (2H, t, J=7 Hz), 6.12 (1H, s), 7.10-7.22 (3H, m), 7.28-7.50 (8H, m), 7.60 (1H, s), 8.43-8.53 (1H, m)

(31)

(E)-4-[3-[3-[Bis(4-isobutylphenyl)methylamino]benzoyl]indol-1-yl]-2-butenoic acid NMR (DMSO-d$_6$, δ) : 0.83 (12H, d, J=8 Hz), 1.62-1.90 (21H, m), 2.38 (4H, d, J=8 Hz), 3.27 (2H, d, J=7 Hz), 5.65 (1H, d, J=7 Hz), 6.24 (1H, dt, J=14, 7 Hz), 6.87 (1H, d, J=8 Hz), 6.97 (1H, d, J=8 Hz), 7.05-7.50 (13H, m), 7.78 (1H, d, J=8 Hz), 8.24 (1H, d, J=8 Hz)

(32)

4-[3-[3-[Bis(4-chlorophenyl)methylamino]benzoyl]indol-1-yl]butyric acid

NMR (CDCl$_3$+CD$_3$OD, δ) : 2.0-2.4 (4H, m), 4.18 (2H, t, J=7 Hz), 5.50 (1H, s), 6.7-6.8 (1H, m), 7.00 (1H, s), 7.1-7.5 (14H, m), 8.35-8.45 (1H, m)

(33)

4-[3-[3-[N-Benzyl-N-[1-(4-isobutylphenyl)propyl]amino]benzoyl]indol-1-yl]butyric acid NMR (CDCl$_3$, δ) : 0.87 (6H, d, J=7 Hz), 1.05 (3H, t, J=7 Hz), 1.7-1.9 (1H, m), 2.0-2.2 (4H, m), 2.3-2.5 (4H, m), 4.08 (2H, t, J=7 Hz), 4.37 (2H, d, J=8 Hz), 5.04 (1H, t, J=7 Hz), 7.0-7.4 (17H, m), 8.4-8.5 (1H, m)

(34)
4-[3-[3-[N-[1-(4-Isobutylphenyl)propyl-N-ethylamino]-benzoyl]indol-1-yl]butyric acid NMR (CDCl3-CD3OD, δ) : 0.89 (6H, d, J=7 Hz), 0.95-1.10 (6H, m), 1.75-2.41 (2H, m), 2.46 (2H, d, J=7 Hz), 3.27 (2H, q, J=7 Hz), 4.50 (2H, t, J=7 Hz), 4.90 (2H, t, J=7 Hz), 7.05-7.60 (10H, m), 7.62 (1H, s), 7.75 (1H, s), 8.30-8.40 (1H, m)

(35)
4-[3-[3-[N-[1-(4-Isobutylphenyl)propyl]-N-methylamino]benzoyl]indol-1-yl]butyric acid NMR (CDCl3, δ) : 0.90 (6H, d, J=7 Hz), 0.98 (3H, t, J=7 Hz), 1.72-2.28 (5H, m), 2.30-2.50 (4H, m), 2.75 (3H, s), 4.23 (2H, t, J=7 Hz), 4.89 (1H, t, J=7 Hz), 6.97-7.48 (11H, m), 7.62 (1H, s), 8.40-8.50 (1H, m)

(36)
4-[3-[3-[N-[2,2-Dimethyl-1-(4-isobutylphenyl)-propyl]N-methylamino]benzoyl]indol-1-yl]butyric acid NMR (CDCl3, δ) : 0.87 (6H, d, J=7 Hz), 1.17 (9H, s), 1.72-1.94 (1H, m), 2.10-2.28 (2H, m), 2.32-2.47 (4H, m), 2.90 (3H, s), 4.24 (2H, t, J=7 Hz), 4.79 (1H, s), 6.98-7.46 (11H, m), 7.62 (1H, s), 8.40-8.50 (1H, m)

(37)
4-[3-[3-[N-[Bis(4-isobutylphenyl)methyl]-N-methylamino]benzoyl]indol- 1-yl]butyric acid NMR (CDCl3, δ) : 0.89 (12H, d, J=7 Hz), 1.73-1.97 (2H, m), 2.07-2.26 (2H, m), 2.37 (2H, t, J=7 Hz), 2.45 (4H, d, J=7 Hz), 2.78 (3H, s), 4.20 (7H, t, J=7 Hz), 6.19 (1H, s), 6.90-7.20 (10H, m), 7.25-7.42 (5H, m), 7.54 (1H, s), 8.40-8.50 (1H, m)

(38)
4-[3-[3-[N-Benzyl-N-[1-(4-isobutylphenyl)ethyl]amino]-benzoyl]indol-1-yl]butyric acid NMR (CDCl3, δ) : 0.88 (6H, d, J=7 Hz), 1.59 (3H, d, J=7 Hz), 1.70-1.94 (1H, m), 2.00-2.20 (2H, m), 2.31 (2H, t, J=7 Hz), 2.42 (2H, d, J=7 Hz), 3.95-4.22 (2H, m), 4.48 (2H, s), 5.34 (1H, q, J=7 Hz), 6.90-7.42 (17H, m), 8.38-8.48 (1H, m)

(39)
4-[3-[3-(10,11-Dihydro-5H-dibenz[b,f]azepin-5-yl-methyl)benzoyl]indol-1-yl]butyric acid NMR (DMSO-d6, δ) : 1.9-2.1 (2H, m), 2.20 (2H, t, J=8 Hz), 3.60 (4H, s), 4.30 (2H, t, J=8 Hz), 5.05 (2H, s), 6.89 (2H, t, J=8 Hz), 7.04-7.70 (12H, m), 7.82 (2H, d, J=10 Hz), 8.26 (1H, dd, J=1, 10 Hz)

EXAMPLE 24

To a solution of 4-[3-[3-[bis(4-isobutylphenyl)-methylamino]benzoyl]indol-1-yl]butyric acid (3.60 g) in ethanol (30 ml) was added a aqueous solution of sodium bicarbonate (7 ml). After filtration, the solvent was removed in vacuo to give a yellow solid of sodium 4-[3-[3-[bis (4-isobutylphenyl)methylamino]benzoyl-indol-1-yl]butyrate (3.68 g).

mp : 118°-125° C.

NMR (DMSO-d6, δ) : 0.83 (12H, d, J=7.5 Hz), 1.78 (2H, m), 1.94 (4H, m), 2.38 (4H, d, J=7.5 Hz), 4.25 (2H, m) 5 65 (1H, d, J=7 5 Hz), 6.75 (1H, d, J=7.5 Hz), 6.8-7.0 (2H, m), 7.10 (2H, d, J=8 Hz), 7.35 (2H, d, J=8 Hz), 7.1-7.3 (3H, m), 7.68 (1H, m), 7.80 (1H, s), 8.25 (1H, m)

EXAMPLE 25

To a solution of 4-[3-[3,5-bis[N-(4-isobutylbenzyl)-N-tert-butoxycarbonylamino]benzoyl]indol-1-yl]butyric acid (1.02 g) in toluene (10 ml) was added 4N solution of hydrogen chloride in 1,4-dioxane (30 ml) at 25° C. The mixture was stirred at 25° for 1 hour, and then hexane (30 ml) was added. The precipitates were filtered and washed with isopropyl ether and hexane to give 4-[3-[3,5-bis[(4-isobutylbenzyl)amino]benzoyl]indol-1-yl]butyric acid dihydrochloride (688 mg) as white powder.

NMR (DMSO-d6, δ) : 0.82 (12H, d, J=7 Hz), 1.79 (2H, m), 2.02 (2H, quin, J=6 Hz), 2.26 (2H, t, J=6 Hz), 2.42 (4H, d, J=7 Hz), 4.28 (2H, t, J=6 Hz), 4.35 (4H, s), 6.78 (1H, broad s), 6.91(2H, broad s), 7.14 (4H, d, J=8 Hz), 7.33 (4H, d, J=8 Hz), 7.2-7.5 (2H, m), 7.65 (1H, m), 7.92 (1H, s), 8.23 (1H, m)

EXAMPLE 26

60% Sodium hydride in mineral oil (0.13 g) was added to a solution of 4-[3-(3-tert-butoxycar-bonylaminobenzoyl)-indol-1-yl]butyric acid (0.47 g) in N,N-dimethylformamide (7 ml). The mixture was stirred at 0° C. for 1 hour. Benzyl bromide (0.95 g) was added to the mixture and the mixture was stirred at room temperature for 20 hours. The mixture was poured into ice water and 0.5N-hydrochloric acid and extracted with ethyl acetate. The organic layer was washed with water, dried over magnesium sulfate and evaporated. The residue was chromatographed on silica gel (30 g) eluting with a mixture of n-hexane and ethyl acetate (5:1) to give benzyl 4-[3-[3-(N-benzyl-N-tert-butoxycarbonylamino)benzoyl]indol-1-yl]butyrate (325 mg) as an oil.

NMR (CDCl3, δ) : 1.42 (9H, s), 2.12-2.43 (4H, m), 4.21 (2H, t, J=7 Hz), 4.90 (2H, s), 5.10 (2H, s), 7.17-7.47(15H, m), 7.5-7.8 (3H, m), 8.4-8.5 (1H, m)

EXAMPLE 27

To a solution of 4-[3-[3-[bis(4-isobutylphenyl)me-thylamino]benzoyl]indol-1-yl]butyric acid (150 mg) and diisopropylethylamine (129 mg) in dichloromethane (3 ml) was added benzylbromide (171 mg). The mixture was stirred at room temperature for 3 days and evaporated. The residue was dissolved in ethyl acetate. The solution was washed with 0.5N hydrochloric acid and water, dried over magnesium sulfate and evaporated. The residue was chromatographed on silica gel (10 g) eluting with a mixture of n-hexane and ethyl acetate (5:1) to give benzyl 4-[3-[3-[N-benzyl-N-[bis(4-isobutyl-phenyl)methyl]amino]benzoyl]indol-1-yl]butyrate (30 mg) as powder.

NMR (CCDl3, δ) : 0.83 (12H, d, J=7 Hz), 1.6-1.9 (2H, m), 2.0-2.15 (2H, m), 2.28 (2H, t, J=7 Hz), 2.39 (4H, d, J=7 Hz), 4.00 (2H, t, J=7 Hz), 4.62 (2H, s), 5.09 (2H, s), 6.38 (1H, s), 6.9-7.4 (26H, m), 8.4-8.5 (1H, m)

EXAMPLE 28

4N Hydrochloric acid in 1,4-dioxane (2 ml) was added to a solution of benzyl 4-[3-[3-[N-benzyl-N-(tert-butoxycarbonyl)amino]benzoyl]indol-1-yl]butyrate (0.31 g) in 1,4-dioxane (2 ml). The mixture was stirred at room temperature for 1 hour and evaporated. The residue was dissolved in ethyl acetate. The solution was washed with sodium bicarbonate aqueous solution and brine, dried over magnesium sulfate and evaporated to give benzyl 4-[3-(3-benzylaminobenzoyl)indol-1-yl]butyrate (258 mg) as an oil.

NMR (CDCl₃, δ) : 2.1-2.3 (2H, m), 2.37 (2H, t, J=7 Hz), 4.17 (2H, t, J=7 Hz), 4.39 (2H, s), 5.08 (2H, s), 6.8-6.9 (1H, m), 7.1-7.45 (16H, m), 7.49 (1H, s), 8.4-8.5 (1H, m)

EXAMPLE 29

To a solution of benzyl 4-[3-(3-benzylaminobenzoyl)-indol-1-yl]butyrate (88 mg) and diisopropylethylamine (45 mg) in dichloromethane (3 ml) was added a solution of 1-bromo-1-(4-isobutylphenyl)propane (90 mg) in dichloromethane (1 ml). The mixture was stirred at room temperature for 24 hours and evaporated. The residue was dissolved in ethyl acetate. The solution was washed with water, dried over magnesium sulfate and evaporated. The residue was chromatographed on silica gel (5 g) eluting with a mixture of n-hexane and ethyl acetate (4:1) to give benzyl 4-[3-[3-[N-benzyl-N-[1-(4-isobutylphenyl)propyl]-amino]benzyl]indol-1-yl]butyrate (30 mg) as an oil.

NMR (CDCl₃, δ) : 0.85 (6H, d, J=7 Hz), 1.03 (3H, t, J=7 Hz), 1.7-1.9 (1H, m), 2.0-2.2 (4H, m), 2.31 (2H, t, J=7 Hz), 2.41 (2H, d, J=7 Hz), 4.06 (2H, t, J=7 Hz), 4.37 (2H, d, J=8 Hz), 5.0-5.1 (3H, m), 7.0-7.4 (22H, m), 8.4-8.5 (1H, m)

EXAMPLE 30

The following compounds were obtained according to a similar manner to that of Example 29.

(1) Ethyl 4-[3-[3-[N-[1-(4-isobutylphenyl)propyl]-N-ethylamino]-benzoyl]indol-1-yl]butyrate NMR (CDCl₃, δ) : 0.88 (6H, d, J=7 Hz) , 0.95-1.08 (6H, m), 1.22 (3H, t, J=7 Hz) , 1.72-2.47 (7H, m), 2.45 (2H, d, J=7 Hz), 3.20 (2H, q, J=7 Hz), 4.11 (2H, q, J=7 Hz), 4.23 (2H, t, J=7 Hz), 4.91 (1H, t, J=7 Hz), 6.97-7.50 (1H, m), 7.63 (1H, s), 8.40-8.50 (1H, m)

(2) Methyl 4-[3-[3-[N-[1-(4-isobutylphenyl)propyl]-N-methylamino]benzoyl]indol-1-yl]butyrate NMR (CDCl₃, δ) : 0.89 (6H, d, J=7 Hz), 1.00 (3H, t, J=7 Hz), 1.74-2.38 (7H, m), 2.43 (2H, d, J=7 Hz), 2.75 (3H, s), 3.65 (3H, s), 4.22 (2H, t, J=7 Hz), 4.91 (1H, t, J=7 Hz), 6.98-7.45 (1H, m), 7.62 (1H, s), 8.40-8.50 (1H, m)

(3) Ethyl 4-[3-[3-[N-[2,2-dimethyl-1-(4-isobutylphenyl)-propyl]-N-methylamino]benzoyl]indol-1-yl]butyrate NMR (CCDl₃, δ) : 0.88 (6H, d, J=7 Hz), 1.14-1.28 (9H, m), 1.72-1.95 (1H, m), 2.10-2.36 (4H, m), 2.42 (2H, d, J=7 Hz), 2.90 (1H, s), 4.10 (2H, q, J=7 Hz), 4.23 (2H, t, J=7 Hz), 4.79 (1H, s), 6.98-7.47 (11H, m), 7.62 (1H, s), 8.40-8.50 (1H, m)

(4) Ethyl 4-[3-[3-[N-[bis(4-isobutylphenyl)methyl]-N-methylamino]benzoyl]indol-1-yl]butyrate NMR (CDCl₃, δ) : 0.90 (12H, d, J=7 Hz), 1.20 (3H, t, J=7 Hz), 1.75-1.98 (2H, m), 2.08-2.34 (4H, m), 2.46 (4H, d, J=7 Hz), 2.79 (3H, s), 4.03-4.26 (4H, m), 6.19 (1H, s), 6.92-7.20 (10H, m), 7.25-7.45 (5H, m), 7.55 (1H, s), 8.40-8.50 (1H, m)

(5) Benzyl 4-[3-[3-[N-benzyl-N-[1-(4-isobutylphenyl)ethyl]amino]-benzoyl]indol-1-yl]butyrate NMR (CDCl₃, δ) : 0.88 (6H, d, J=7 Hz), 1.61 (3H, d, J=7 Hz), 1.72-1.95 (1H, m), 2.00-2.20 (2H, m), 2.30 (2H, t, J=7 Hz), 2.43 (2H, d, J=7 Hz), 4.04 (2H, m), 4.47 (2H, s), 5.09 (2H, s), 5.35 (1H, t, J=7 Hz), 6.9-7.4 (22H, m), 8.38-8.48 (1H, m)

EXAMPLE 31

Benzyl 4-[3-[3-[N-benzyl-N-[bis(4-isobutylphenyl)-methyl]amino]benzoyl]indol-1-yl]butyrate (24 mg) was dissolved in a mixture of methanol 93 mi) and 1,4-dioxane (3 ml), and 10% palladium on carbon (12 mg) was added. The mixture was stirred under hydrogen atmosphere at room temperature for 5 hours. The catalyst was removed by filtration and the filtrate was evaporated. The residue was chromatographed on silica gel (2 g) eluting with a mixture of chloroform and methanol (50:1) to give 4-[3-[3-[N-benzyl-N-[bis(4-isobutylphenyl)methyl]amino]benzoyl]indol-1-yl]butyric acid as (14 mg) powder.

NMR (CDCl₃, δ) : 0.82 (12H, d, J=7 Hz) 1.7-1.9 (2H, m), 2.0-2.2 (2H, m), 2.2-2.45 (6H, m), 4.03 (2H, t, J=7 Hz), 4.63 (2H, s), 6.38 (1H, s), 6.9-7.4 (21H, m), 8.4-8.5 (1H, m)

EXAMPLE 32

4-[3-(3-Aminobenzoyl)indol-1-yl]butyric acid (0.32 g) was dissolved in a solution of bis(trimethylsilyl)acetamide (0.25 ml) in dichloromethane (10 ml) at room temperature. Hexamethyleneiminocarbonyl chloride (0.48 g) was added to the solution. The solution was refluxed for 3 hours and cooled to room temperature. 3-Dimethylaminopropylamine (1 ml) was added to the solution. The mixture was stirred for 5 minutes and evaporated. The residue was dissolved in a mixture of 0.5N hydrochloric acid and ethyl acetate. The organic layer was washed with water, dried over magnesiium sulfate and evaporated. The residue was chromatographed on silica gel (30 g) eluting with chloroform to give 4-[3-[3-(hexamethyleneiminocarbonylamino)benzoyl]indol-1-yl]butyric acid (0.24 g) as an oil.

NMR (CDCl₃+CD₃OD, δ) : 1.6-1.9 (8H, m), 2.1-2.4 (4H, m), 3.55 (4H, t, J=7 Hz), 4.32 (2H, t, J=7 Hz), 7.3-7.5 (5H, m), 7.65-7.75 (2H, m), 7.78 (1H, s), 8.35-8.45 (1H, m)

EXAMPLE 33

The following compounds were obtained according to a similar manner to that of Example 9.

(1) Ethyl 4-[3-[3-(phenoxazin-10-ylmethyl)benzoyl]indol-1-yl]butyrate

NMR (CDCl₃, δ): 1.22 (3H t, J=8 Hz), 2.00-2.15 (2H, m), 2.28 (2H, t, J=8 Hz), 4.00-4.20 (4H, m), 4.90 (2H, s), 6.37 (2H, dd, J=1, 8 Hz), 6.66-6.80 (6H, m), 7.28-7.45 (6H, m), 7.53 (2H, dd, J=1, 8 Hz), 7.7-7.8 (2H, m), 8.4-8.5 (1H, m)

(2) Ethyl 4-[3-[3-(phenothiazin-10-ylmethyl)benzoyl]indol-1-yl]butyrate

NMR (CDCl₃, δ) : 1.25 (3H, t, J=8 Hz), 1.98-2.16 (2H, m), 2.27 (2H, t, J=8 Hz), 4.10-4.20 (4H, m), 5.20

(2H, s), 6.68 (2H, d, J=8 Hz), 6.8–7.8 (14H, m), 8.4–8.5 (1H, m)

EXAMPLE 34

The following compounds were obtained according to a similar manner to that of Example 22.

(1) 4-[3-[3-(Phenoxazin-10-ylmethyl)benzoyl]indol-1-yl]butyric acid

NMR (DMSO-$d_6$, δ): 1.85–2.00 (2H, m), 2.20 (2H, t, J=8 Hz), 4.20 (2H, t, J=8 Hz), 5.00 (2H, s), 6.55 (2H, dd, J=1, 8 Hz), 6.64–6.85 (7H, m), 7.20–7.35 (2H, m), 7.50–7.75 (3H, m), 8.25 (1H, dd, J=, 8 Hz), 8.34 (1H, s)

(2) 4-[3-[3-(Phenothiazin-10-ylmethyl)benzoyl]indol-1-yl]butyric acid

NMR (DMSO-$d_6$, δ): 1.85–2.05 (2H, m), 2.22 (2H, t, J=8 Hz), 4.20 (2H, t, J=8 Hz), 5.25 (2H, s), 6.8–7.8 (15H, m), 8.26 (1H, dd, J=1, 8 Hz), 8.35 (1H, s)

EXAMPLE 35

A solution of 4N-hydrogen chloride (1.5 ml) in ethyl acetate was added to a solution of 4-[3-[3-[bis(4-isobutylphenyl)methylamino]benzoyl]indol-1-yl]butyric acid (3.0 g) in ethyl acetate (15 ml). The mixture was refrigerated for 16 hours to give 4-[3-[3-[bis(4-isobutylphenyl)methylamino]benzoyl]indol-1-yl]butyric acid hydrochloride as yellow crystals (3.1 g).

NMR (DMSO-$d_6$, δ): 0.80 (12H, d, J=7 Hz), 1.7–1.9 (2H, m), 1.9–2.1 (2H, m), 2.1–2.3(2H, m), 2.40 (4H, d, J=7 Hz), 4.2–4.4 (2H, m), 5.67 (1H, s), 6.9–7.4 (6H, m), 7.12 (4H, d, J=8 Hz), 7.33 (4H, d, J=8 Hz), 7.62 (1H, m), 7.88 (1H, s), 8.25 (1H, m)

PREPARATION 65

To a suspension of aluminum chloride (6.67 g) in dichloromethane (70 ml) was added hexanoyl chloride (7.0 ml) at 0° C. After the mixture was stirred at 0° C. for 15 minutes, isobutylbenzene (7.9 ml) was added to the mixture. The mixture was stirred at 0° C. for 30 minutes and poured into ice water. The separated organic layer was washed with water, aqueous sodium bicarbonate and brine. The solution was dried over magnesium sulfate and evaporated to give 4'-isobutylhexanophenone (10.52 g) as a colorless oil.

NMR (CDCl$_3$, δ) : 0.84–0.98 (9H, m), 1.30–1.43 (4H, m), 1.60–2.01 (3H, m), 2.53 (2H, d, J=8.5 Hz), 2.94 (2H, t, J=7 Hz), 7.22 (2H, d, J=8.5 Hz), 7.88 (2H, d, J=8.5 Hz)

PREPARATION 66

The following compounds were obtained according to a similar manner to that of Preparation 65.

(1) 4'-Isobutylbutyrophenone

NMR (CDCl$_3$, δ) : 0.86–1.07 (9H, m), 1.67–2.01 (3H, m), 2.53 (2H, d, J=7 Hz), 2.93.(2H, t, J=7.5 Hz), 7.22 (2H, d, J=8.5 Hz), 7.88 (2H, d, J=8.5 Hz)

(2) 4'-Isobutylpentanophenone

NMR (CDCl$_3$, δ) : 0.85–1.00 (9H, m), 1.31–1.51 (2H, m), 1.60–2.01 (3H, m), 2.53 (2H, d, J=7 Hz), 2.95 (2H, t, J=7.5 Hz), 7.22 (2H, d, J=8.5 Hz), 7.88 (2H, d, J=8.5 Hz)

(3) 4'-Isobutylheptanophenone

NMR (CDCl$_3$, δ) : 0.82–0.97 (9H, m), 1.18–1.47 (6H, m), 1.55–2.01 (3H, m), 2.53 (2H, d, J=7 Hz), 2.94 (2H, t, J=7.5 Hz), 7.22 (2H, d, J=8 Hz), 7.88 (2H, d, J=8 Hz)

(4) 4'-Isobutyloctanophenone

NMR (CDCl$_3$, δ) : 0.82–0.98 (9H, m), 1.20–1.46 (8H, m), 1.63–2.01 (3H, m), 2.53 (2H, d, J=7 Hz), 2.95 (2H, t, J=7.5 Hz), 7.22 (2H, d, J=8 Hz), 7.88 (2H, d, J=8 Hz)

PREPARATION 67

To a solution of 4'-isobutylhexanophenone (10.5 g) in 2-propanol (60 ml) was added sodium borohydride (2.05 g), and the mixture was stirred at 50° C. for 6 hours. The mixture was poured into ice water and acidified with 6N hydrochloric acid. The aqueous solution was extracted with ethyl acetate and the combined organic layer was washed with water and brine, dried over magnesium sulfate and evaporated to give 1-(4-isobutylphenyl)hexan-1-ol (9.32 g) as a colorless oil.

NMR (CDCl$_3$, δ) : 0.83–0.96 (9H, m), 1.16–1.40 (6H, m), 1.60–1.96 (3H, m), 2.48 (2H, d, J=7 Hz), 4.64 (1H, t, J=7 Hz), 7.11 (2H, d, J=8.5 Hz), 7.25 (2H, d, J=8.5 Hz)

PREPARATION 68

The following compounds were obtained according to a similar manner to that of Preparation 67.

(1) 1-(4-Isobutylphenyl)butan-1-ol

NMR (CDCl$_3$, δ) : 0.86–0.98 (9H, m), 1.16–1.97 (5H, m), 2.47 (2H, d, J=7 Hz), 4.65 (1H, t, J=7 Hz), 7.11 (2H, d, J=8 Hz), 7.26 (2H, d, J=8 Hz)

(2) 1-(4-Isobutylphenyl)pentan-1-ol

NMR (CDCl$_3$, δ) : 0.82–0.95 (9H, m), 1.17–1.48 (4H, m), 1.60–1.97 (3H, m), 2.47 (2H, d, J=7 Hz), 4.63 (1H, t, J=7 Hz), 7.11 (2H, d, J=5Hz), 7.25 (2H, d, J=8 Hz)

(3) 1-(4-Isobutylphenyl)heptan-1-ol

NMR (CDCl$_3$, δ) : 0.80–0.97 (9H, m) 1.16–1.50 (8H, m), 1.58–1.97 (3H, m), 2.47 (2H, d, J=7 Hz), 4.63 (1H, t, J=7 Hz), 7.11 (2H, d, J=8 Hz), 7.25 (2H, d, J=8 Hz)

(4) 1-(4-Isobutylphenyl)octan-1-ol

NMR (CDCl$_3$, δ) : 0.80–0.97 (9H, m), 1.16–1.50 (10H, m), 1.60–1.97 (3H, m), 2.47 (2H, d, J=7 Hz), 4.63 (1H, t, J=7 Hz), 7.12 (2H, d, J=8 Hz), 7.26 (2H, d, J=8 Hz)

PREPARATION 69

To a solution of 1-(4-isobutylphenyl)hexan-1-ol (9.15 g) and carbon tetrabromide (25.9 g) in tetrahydrofuran (250 ml) was added triphenylphosphine (20.5 g). The mixture was stirred at room temperature for 6 hours. After the white solid was filtered off, the filtrate was evaporated. n-Hexane (300 ml) was added to the residue and the precipitate was filtered off. The filtrate was evaporated and the residual oil was distilled under reduced pressure to give 1-(1-bromohexyl)-4-isobutylbenzene (3.52 g) as a colorless oil.

NMR (CDCl$_3$, δ) : 0.82–0.97 (9H, m), 1.20–1.60 (8H, m), 1.74–1.97 (1H, m), 2.00–2.38 (2H, m), 2.46 (2H, d, J=7 Hz), 4.96 (1H, t, J=7.5 Hz), 7.10 (2H, d, J=8.5 Hz), 7.29 (2H, d, J=8.5 Hz)

PREPARATION 70

The following compounds were obtained according to a similar manner to that of Preparation 69.

(1) 1-(1-Bromobutyl)-4-isobutylbenzene

NMR (CDCl$_3$, δ) : 0.84–1.00 (9H, m), 1.18–2.38 (5H, m), 2.46 (2H, d, J=7 Hz), 4.99 (1H, t, J=7.5 Hz), 7.10 (2H, d, J=8 Hz), 7.30 (2H, d, J=8 Hz)

(2) 1-(1-Bromopentyl)-4-isobutylbenzene

NMR (CDCl$_3$, δ) : 0.80–0.94 (9H, M), 1.15–1.55 (4H, m), 1.60–1.97 (3H, m), 2.46 (2H, d, J=7 Hz), 4.96 (1H, t, J=7.5 Hz), 7.10 (2H, d, J=8 Hz), 7.29 (2H, d, J=8 Hz)

(3) 1- (1-Bromoheptyl) -4-isobutylbenzene

NMR (CDCl$_3$, δ) : 0.81–0.97 (9H, m), 1.16–1.55(8H, m), 1.73–1.98 (1H, m), 2.03–2.35 (2H, m), 2.46 (2H, d, J=7 Hz ), 4.97 (1H, t, J=7.5 Hz), 7.10 (2H, d, J=8 Hz), 7.30 (2H, d, J=8 Hz)

(4) 1-(1-Bromooctyl)-4-isobutylbenzene)

NMR (CDCl$_3$, δ) : 0.82–1.06 (9H, m) , 1.18–1.55 (10H, m), 1.72–1.96 (1H, m), 2.08–2.30 (2H, m), 2.45 (2H, d, J=7 Hz), 4.97 (1H, t, J=7.5 Hz), 7.10 (2H, d, J=8 Hz), 7.30 (2H, d, J=8 Hz)

PREPARATION 71

4'-Isobutylpentanophenone (2.1 g) was added to a solution of (+)-B-chlorodiisopinocampheylborane (3.57 g) in tetrahydrofuran (7 ml) at −25° C. After stirring for 5 hours, the solvent was removed and the residue was dissolved in ethyl ether (30 ml). To this solution was added diethanolamine (2 ml), and the mixture was stirred for 2 hours. The solid was filtered off and washed with ethyl ether. The combined filtrates were concentrated and the residue was chromatographed on silica gel (hexane:dichloromethane =1:2) to give (R)-1-(4-isobutylphenyl)pentan-1-ol (635 mg).

NMR (CDCl$_3$, δ): 0.85–0.95 (3H, m), 0.89 (6H, d, J=7 Hz), 1.2–1.5 (4H, m), 1.6–2.0 (3H, m), 2.45 (2H, d, J=7 Hz), 4.63 (1H, t, J=7 Hz), 7.11 (2H, d, J=8 Hz), 7.25 (2H, d, J=8 Hz)

PREPARATION 72

(S)-1-(4-Isobutylphenyl)pentan-1-ol was obtained by reacting 4'-isobutylpentanophenone with (-)-B-chlorodiisopinocampheylborane according to a similar manner to that of Preparation 71.

NMR (CDCl$_3$, δ): 0.85–0.95 (3H, m), 0.89 (6H, d, J=7 Hz), 1.2–1.5 (4H, m), 1.6–2.0 (3H, m), 2.45 (2H, d, J=7 Hz), 4.63 (1H, t, J=7 Hz), 7.11 (2H, d, J=8 Hz), 7.25 (2H, d, J=8 Hz)

EXAMPLE 36

A mixture of ethyl 4-[3-(4-hydroxybenzoyl)indol-1-yl]butyrate (176 mg), 1-(1-bromohexyl}-4-isobutylbenzene (223 mg) and potassium carbonate (207 mg) in N,N-dimethylformamide (4 ml) was stirred at room temperature for 6 hours. The reaction mixture was filtered and the filtrate was poured into a mixture of ethyl acetate and 0.5N hydrochloric acid. The organic phase was separated, washed with water and brine, dried over magnesium sulfate and evaporated. The residue was chromatographed on silica gel column eluting with a mixture of n-hexane and ethyl acetate (3:1) to give ethyl 4-[3-[4-[1-(4-isobutylphenyl)hexyloxy]benzoyl]indol-1-yl]-butyrate (279 mg) as an oil.

NMR (CDCl$_3$, δ) : 0.8–0.95 (9H, m), 1.15–1.65 (9H, m), 1.7–2.35 (7H, m), 2.45 (2H, d, J=7 Hz), 4.09 (2H, q, J=7 Hz), 4.23 (2H, t, J=7 Hz), 5.14 (1H, dd, J=2 Hz and 7 Hz), 6.92 (2H, d, J=9 Hz), 7.11 (2H, d, J=8 Hz), 7.2–7.45 (5H, m), 7.53 (1H, s), 7.74 (2H, d, J=9 Hz), 8.3–8.4 (1H, m)

EXAMPLE 37

The following compounds were obtained according to a similar manner to that of Example 36.

(1) Ethyl 4-[3-[4-[1-(4-isobutylphenyl)butoxy]benzoyl]-indol-1-yl]butyrate

NMR (CDCl$_3$, δ) : 0.8–1.05 (9H, m), 1.20 (3H, t, J=7 Hz), 1.3–1.65 (2H, m), 1.7–2.35 (7H, m), 2.45 (2H, d, J=7 Hz), 4.09 (2H, q, J=7 Hz), 4.23 (2H, t, J=7 Hz), 5.17 (1H, dd, J=2 Hz and 7 Hz), 6.92 (2H, d, J=9 Hz), 7.11 (2H, d, J=8 Hz), 7.2–7.45 (5H, m), 7.53 (1H, s), 7.74 (2H, d, J=9 Hz), 8.3–8.4 (1H, m)

(2) Ethyl 4-[3-[4-[1-(4-isobutylphenyl)pentyloxy]-benzoyl]indol-1-yl]butyrate

NMR (CDCl$_3$, δ) : 0.8–1.0 (9H, m), 1.20 (3H, t, J=7 Hz), 1.3–1.65 (4H, m), 1.75–2.35 (7H, m), 2.45 (2H, d, J=7 Hz), 4.10 (2H, q, J=7 Hz), 4.23 (2H, t, J=7 Hz), 5.15 (1H, dd, J=2 Hz and 7 Hz), 6.92 (2H, d, J=9 Hz), 7.11 (2H, d, J=8 Hz), 7.2–7.45 (5H, m), 7.53 (1H, s), 7.74 (2H, d, J=9 Hz), 8.3–8.4 (1H, m)

(3) Ethyl 4-[3-[4-[1-(4-isobutylphenyl)heptyloxy]-benzoyl]indol-1-yl]butyrate

NMR (CDCl$_3$, δ) : 0.8–0.95 (9H, m), 1.15–1.65 (11H, m), 1.7–2.35 (7H, m), 2.45 (2H, d, J=7 Hz), 4.10 (2H, q, J=7 Hz), 4.13 (2H, t, J=7 Hz), 5.15 (1H, dd, J=2 Hz and 7 Hz), 6.92 (2H, d, J=9 Hz), 7.11 (2H, d, J=8 Hz), 7.2–7.45 (5H, m), 7.53 (1H, s), 7.74 (2H, d, J=9 Hz), 8.3–8.4 (1H, m)

(4) Ethyl 4-[3-[4-[1-(4-isobutylphenyl)octyloxy]-benzoyl]indol-1-yl]butyrate

NMR (CDCl$_3$, δ) : 0.8–0.95 (9H, m), 1.15–1.65 (13H, m), 1.7–2.35 (7H, m), 2.45 (2H, d, J=7 Hz), 4.10 (2H, q, J=7 Hz), 4.23 (2H, t, J=7 Hz), 5.15 (1H, dd, J=2 Hz and 7 Hz), 6.92 (2H, d, J=9 Hz), 7.11 (2H, d, J=8 Hz), 7.2–7.45 (5H, m), 7.53 (1H, s), 7.74 (2H, d, J=9 Hz), 8.3–8.4 (1H, m)

EXAMPLE 38

To a solution of ethyl 4-[3-[4-[1-(4-isobutylphenyl)-hexyloxy]benzoyl]indol-1-yl]butyrate (270 mg) in ethanol (3 ml) and 1,4-dioxane (3 ml) was added 1N aqueous solution of sodium hydroxide (1.5 ml). The mixture was stirred at room temperature for 3 hours, and then poured into a mixture of ethyl acetate and 0.5N hydrochloric acid. The organic layer was separated, washed with water and brine, dried over magnesium sulfate and evaporated to give 4-[3-[4-[1-(4-isobutylphenyl)hexyloxy]benzoyl]indol-1-yl]butyric acid (230 mg) as powder.

NMR (CDCl$_3$, δ) : 0.8–0.95 (9H, m), 1.2–1.65 (6H, m), 1.7–2.3 (5H, m), 2.36 (2H, d, J=7 Hz), 2.44 (2H, d, J=7 Hz), 4.22 (2H, t, J=7 Hz), 5.15 (1H, dd, J=2 Hz and 7 Hz), 6.92 (2H, d, J=9 Hz), 7.10 (2H, d, J=8 Hz), 7.2–7.45 (5H, m), 7.54 (1H, s), 7.73 (2H, d, J=9 Hz), 8.3–8.4 (1H, m)

EXAMPLE 39

The following compounds were obtained according to a similar manner to that of Example 38.

(1)
4-[3-[4-[1-(4-Isobutylphenyl)butoxy]benzoyl]indol-1-yl]butyric acid

NMR(CDCl$_3$, δ): 0.8–1.05 (9H, m), 1.3–1.65 (2H, m), 1.7–2.3 (5H, m), 2.36 (2H, d, J=7 Hz), 2.44 (2H, d, J=7 Hz), 4.24 (2H, t, J=7 Hz), 5.17 (1H, dd, J=2 Hz and 7 Hz), 6.92 (2H, d, J=9 Hz), 7.10 (2H, d, J=8 Hz), 7.2–7.45 (5H, m), 7.54 (1H, s), 7.73 (2H, d, J=9 Hz), 8.3–8.4 (1H, m)

(2)
4-[3-[4-[1-(4-Isobutylphenyl)pentyloxy]benzoyl]-indol-1-yl]butyric acid

NMR (CDCl$_3$, δ) : 0.8–1.0 (9H, m), 1.25–1.6 (4H, m), 1.75–2.3 (5H, m), 2.37 (2H, d, J=7 Hz), 2.43 (2H, d, J=7 Hz), 4.24 (2H, t, J=7 Hz), 5.14 (1H, dd, J=2 Hz, 7 Hz), 6.92 (2H, d, J=9 Hz), 7.10 (2H, d, J=8 Hz), 7.2–7.45 (5H, m), 7.54 (1H, s), 7.73 (2H, d, J=9 Hz), 8.3–8.4 (1H, m)

(3)
4-[3-[4-[1-(4-Isobutylphenyl)heptyloxy]benzoyl]-indol-1-yl]butyric acid

NMR (CDCl$_3$, δ) : 0.8–0.95 (9H, m), 1.15–1.65 (8H, m), 1.7–2.30 (5H, m), 2.32–2.5 (4H, m), 4.23 (2H, t, J=7 Hz), 5.15 (1H, dd, J=2 Hz and 7 Hz), 6.92 (2H, d, J=9 Hz), 7.10 (2H, d, J=8 Hz), 7.2–7.45 (1H, s), 7.73 (2H, d, J=9 Hz), 8.3–8.4 (1H, m)

(4)
4-[3-[4-[1-(4-Isobutylphenyl)octyloxy]benzoyl]-indol-1-yl]butyric acid

NMR (CDCl$_3$, δ) : 0.8–0.95 (9H, m), 1.15–1.6 (10H, m), 1.7–2.28 (5H, m), 2.32–2.5 (4H, m), 4.24 (2H, t, J=7 Hz), 5.15 (1H, dd, J=2 Hz and 7 Hz), 6.92 (2H, d, J=9 Hz), 7.10 (2H, d, J=8 Hz), 7.2–7.45 (5H, m), 7.54 (1H, s), 7.73 (2H, d, J=9 Hz), 8.3–8.4 (1H, m)

EXAMPLE 40

A mixture of ethyl 4-[3-(3-aminobenzoyl)indol-1-yl]-butyrate (176 mg), 1-(1-bromohexyl)-4-isobutylbenzene (233 mg) and diisopropylethylamine (194 mg) in dichloromethane (5 ml) was refluxed for 20 hours. The reaction mixture was poured into a mixture of ethyl acetate and water. The organic layer was separated and washed with water and brine, dried over magnesium sulfate and evaporated. The residue was chromatographed on silica gel column eluting with a mixture of n-hexane and ethyl acetate (3:1) to give ethyl 4-[3-[3-[1-(4-isobutylphenyl)hexylamino]benzoyl]-indol-1-yl]butyrate (155 mg) as an oil.

NMR (CDCl$_3$, δ): 0.8–0.95 (9H, m), 1.15–1.5 (9H, m), 1.65–1.95 (3H, m), 2.05–2.35 (4H, m), 2.43 (2H, d, J=7 Hz), 4.05–4.4 (6H, m), 6.67 (1H, d, J=8 Hz), 6.95–7.5 (11H, m), 8.4–8.5 (1H, m)

EXAMPLE 41

The following compounds were obtained according to a similar manner to that of Example 40.

(1) Ethyl 4-[3-[3-[1-(4-isobutylphenyl)propylamino]benzoyl]indol-1-yl]butyrate

NMR (CDCl$_3$, δ) : 0.85–1.0 (9H, m), 1.21 (3H, t, J=7 Hz), 1.7–2.0 (3H, m), 2.1–2.35 (4H, m), 2.45 (2H, d, J=7 Hz), 4.0–4.35 (5H, m), 6.68 (1H, d, J=8 Hz), 7.0–7.5 (11H, m), 8.4–8.5 (1H, m)

(2) Ethyl 4-[3-[3-[1-(4-isobutylphenyl)butylamino]benzoyl]indol-1-yl]butyrate

NMR (CDCl$_3$, δ) : 0.8–1.0 (9H, m), 1.20 (3H, t, J=7 Hz), 1.25–1.5 (2H, m), 1.65–1.95 (3H, m), 2.05–2.35 (4H, m), 2.43 (2H, d, J=7 Hz), 4.0–4.4 (6H, m), 6.68 (1H, d, J=8 Hz), 6.95–7.5 (11H, m), 8.4–8.5 (1H, m)

(3) Ethyl 4-[3-[3-[1-(4-isobutylphenyl)pentylamino]benzoyl]indol-1-yl]butyrate

NMR (CDCl$_3$, δ) : 0.8–0.95 (9H, m), 1.15–1.5 (7H, m), 1.65–1.95 (3H, m), 2.05–2.35 (4H, m), 2.43 (2H, d, J=7 Hz), 4.05–4.4 (5H, m), 6.68 (1H, d, J=8 Hz), 7.0–7.5 (11H, m), 8.4–8.5 (1H, m)

EXAMPLE 42

To a solution of ethyl 4-[3-[3-1-(4-isobutylphenyl)-hexylamino]benzoyl]indol-1-yl]butyrate (150 mg) in ethanol (2 ml) and 1,4-dioxane (2 ml) was added 1N aqueous solution of sodium hydroxide (1 ml). The mixture was stirred at room temperature for 3 hours, and then poured into a mixture of ethyl acetate and 0.5N hydrochloric acid. The organic layer was separated, washed with water and brine, dried over magnesium sulfate and evaporated to give 4-[3-[3-[1-(4-isobutylphenyl)hexylamino]benzoyl]indol-1-yl]butyric acid (130 mg) as powder.

NMR (CDCl$_3$, δ) : 0.75–0.95 (9H, m), 1.15–1.5 (6H, m), 1.65–1.95 (3H, m), 2.05–2.25 (2H, m), 2.3–2.45 (4H, m), 4.05–4.8 (5H, m), 6.67 (1H, d, J=8 Hz), 6.95–7.5 (11H, m), 8.4–8.5 (1H, m)

EXAMPLE 43

The following compounds were obtained according to a similar manner to that of Example 42.

(1)
4-[3-[3-[1-(4-Isobutylphenyl)propylamino]benzoyl]indol-1-yl]butyric acid

NMR (CDCl$_3$, δ) : 0.8–1.0 (9H, m), 1.7–1.95 (3H, m), 2.05–2.5 (6H, m), 4.05–4.3 (3H, m), 6.68 (1H, d, J=8 Hz), 7.0–7.5 (11H, m), 8.4–8.5 (1H, m)

(2)
4-[3-[3-[1-(4-Isobutylphenyl)butylamino]benzoyl]indol-1-yl]butyric acid

NMR (CDCl$_3$, δ) : 0.8–1.05 (9H, m), 1.2–1.55 (2H, m), 1.65–1.95 (3H, m), 2.1–2.5 (6H, m), 4.1–4.5 (4H, m), 6.68 (1H, d, J=8 Hz), 6.95–7.5 (11H, m), 8.4–8.5 (1H, m)

(3)
4-[3-[3-[1-(4-Isobutylphenyl)pentylamino]benzoyl]indol-1-yl]butyric acid

NMR (CDCl$_3$, δ) : 0.8–0.95 (9H, m), 1.2–1.45 (4H, m), 1.7–1.95 (3H, m), 2.1–2.5 (6H, m), 4.05–4.4 (3H, m), 6.68 (1H, d, J=8 Hz), 7.0–7.5 (11H, m), 8.4–8.5 (1H, m)

EXAMPLE 44

To a mixture of ethyl 4-[3-(4-hydroxybenzoyl)indol-1-yl]butyrate (275 mg), (R)-1-(4-isobutylphenyl)pentan-1-ol (179 mg) and triphenylphosphine (213 mg) in a mixture of tetrahydrofuran and toluene (1:4, 10 ml) was added diethyl azodicarboxylate (0.13 ml) at −25° C. After stirring for 1 hour, the reaction mixture was concentrated in vacuo. The concentrate was chromatographed on silica gel using hexane and ethyl acetate (3:1) to give ethyl (S)-4-[3-[4-[1-(4-isobutylphenyl)pentyloxy]benzoyl]indol-1-yl]butyrate (279 mg).

NMR (CDCl$_3$, δ): 0.89 (6H, d, J=7 Hz), 0.8–0.95 (3H, m), 1.20 (3H, t, J=7 Hz), 1.3–1.65 (4H, m), 1.75–2.35 (7H, m), 2.45 (2H, d, J=7 Hz), 4.10 (2H, q, J=7 Hz), 4.23 (2H, t, J=7 Hz), 5.15 (1H, dd, J=5, 7 Hz), 6.92 (2H, d, J=9 Hz), 7.11 (2H, d, J=8 Hz), 7.2–7.45 (5H, m), 7.53 (1H, s), 7.74 (2H, d, J=9 Hz), 8.34 (1H, m)

EXAMPLE 45

Ethyl (R)-4-[3-[4-[1-(4-isobutylphenyl)pentyloxy]benzoyl]indol-1-yl]butyrate was obtained by reacting ethyl 4-[3-(4-hydroxybenzoyl)indol-1-yl]butyrate with (S)-1-(4-isobutylphenyl)pentan-1-ol according to a similar manner to that of Example 44.

NMR (CDCl$_3$, δ): 0.89 (6H, d, J=7 Hz), 0.8–0.95 (3H, m), 1.20 (3H, t, J=7 Hz), 1.3–1.65 (4H, m), 1.75–2.35 (7H, m), 2.45 (2H, d, J=7 Hz), 4.10 (2H, q, J=7 Hz), 4.23 (2H, t, J=7 Hz), 5.15 (1H, dd, J=5,7 Hz), 6.92 (2H, d, J=9 Hz), 7.11 (2H, d, J=8 Hz), 7.2–7.45 (5H, m), 7.53 (1H, s), 7.74 (2H, d, J=9 Hz), 8.34 (1H, m)

EXAMPLE 46

The following compounds were obtained according to a similar manner to that of Example 38.

(1)

(S)-4-[3-[4-[1-(4-Isobutylphenyl)pentyloxy]benzoyl]indol-1-yl]butyric acid

NMR (CDCl$_3$, δ): 0.89 (6H, d, J=7 Hz), 0.85–0.95 (3H, m), 1.25–1.6 (4H, m), 1.75–2.3 (5H, m), 2.37 (2H, t, J=7 Hz), 2.43 (2H, d, J=7 Hz), 4.24 (2H, t, J=7 Hz), 5.14 (1H, dd, J=5,7 Hz), 6.92 (2H, d, J=9 Hz), 7.10 (2H, d, J=8 Hz), 7.2–7.45 (5H, m), 7.54 (1H, s), 7.73 (2H, d, J=9 Hz), 8.33 (1H, m) [α]$_D^{25}$: −61.0 ° (C=1.0, chloroform)

(2)

(R)-4-[3-[4-[1-(4-Isobutylphenyl)pentyloxy]benzoyl]indol-1-yl]butyric acid

NMR (CDCl$_3$, δ): 0.89 (6H, d, J=7 Hz), 0.85–0.95 (3H, m), 1.25–1.6 (4H, m), 1.75–2.3 (5H, m), 2.37 (2H, t, J=7 Hz), 2.43 (2H, d, J=7 Hz), 4.24 (2H, t, J=7 Hz), 5.14 (1H, dd, J=5,7 Hz), 6.92 (2H, d, J=9 Hz), 7.10 (2H, d, J=8 Hz), 7.2–7.45 (5H, m), 7.54 (1H, s), 7.73 (2H, d, J=9 Hz), 8.33 (1H, m) [α]$_D^{25}$: +62.4° (C=0.5, chloroform)

What we claim is:

1. A compound of the formula:

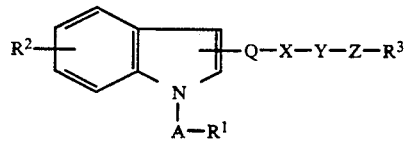

wherein $R^1$ is carboxy of pharmaceutically acceptable salts and esters thereof;

$R^2$ is hydrogen, lower alkyl or halogen;

$R^3$ is phenyl, naphthyl, phenyl or naphthyl each substituted by from one to three $C_{1-6}$ alkyl groups, mono- di- or triphenyl($C_{1-6}$)alkyl; mono-, di- or triphenyl($C_{1-6}$)alkyl substituted by from one to three substituents selected from the group consisting of $C_{1-6}$ alkyl, halogen, cyano, carboxy, mono-, di- or triphenyl($C_{1-6}$)alkyoxycarbonyl, mono- or di(lower)alkylphenylcarbamoyl, di($C_1$-$C_6$)alkylcarbamoyl, phenylcarbamoyl and ($C_1$-$C_6$)alkylphenylcarbamoyl;

A is lower alkylene which may be substituted by oxo or lower alkylene,

Q is carbonyl or lower alkylene,

X is

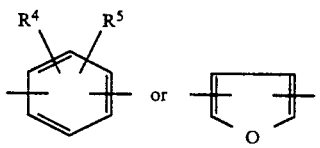

in which $R^4$ is hydrogen or $C_{1-6}$ alkyl, and $R^5$ is hydrogen, $C_{1-6}$ alkyl or Y—Z—$R^3$, Y is a bond or lower alkylene, Z is lower alkylene,

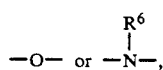

in which $R^6$ is hydrogen, ($C_1$-$C_6$) alkyl, mono-, di- or triphenyl($C_{1-10}$)alkyl, $C_{1-6}$ alkyl or lower alkoxycarbonyl substituted mono-, di- or triphenyl($C_{1-6}$)alkyl or pharmaceutically acceptable carboxylic acid acyl, and pharmaceutically acceptable salts thereof.

2. A compound of claim 1, wherein $R^1$ is carboxy, lower alkoxycarbonyl or mono-, di- or triphenyl(lower)alkoxy carbonyl, $R^3$ is phenyl substituted by lower alkyl; or mono-, di- or triphenyl($C_{1-10}$)alkyl which may be substituted by 1-3 substituents selected from $C_{1-6}$ alkyl, halogen, cyano, carboxyl, mono-, di- or triphenyl(lower)alkoxycarbonyl, mono- or di(lower)alkylphenylcarbamoyl, phenylcarbamoyl and ($C_{1-4}$) alkylphenylcarbamoyl; and $R^6$ is hydrogen, $C_{1-6}$ alkyl, mono-, di- or triphenyl($C_{1-10}$)alkyl which may be substituted by $C_{1-6}$ alkyl or lower alkoxycarbonyl.

3. A compound of claim 2, which is represented by the formula:

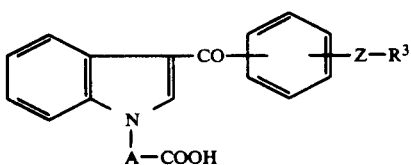

wherein

R³ is mono- or diphenyl C₁₋₁₀ alkyl which may be substituted by one or two substituents selected from C₁₋₆ alkyl, halogen, cyano, carboxy, phenyl(lower)alkoxycarbonyl, mono- or di(lower)alkylcarbamoyl, phenylcarbamoyl and C₁₋₆ alkylphenylcarbamoyl, A is lower alkylene, and Z is lower alkylene, —O— or

in which R⁶ is hydrogen, C₁₋₆ alkyl or phenyl(lower)alkyl.

4. A compound of claim 3, which is selected from the group consisting of:
4-[3-[3-[bis(4-isobutylphenyl)methylamino]benzoyl]indol-1-yl]butyric acid,
4-[3-[4-[bis(4-isobutylphenyl)methoxy]benzoyl]indol-1-yl]butyric acid,
4-[3-[4-[1-(4-isobutylphenyl)ethoxy]benzoyl]indol-1-yl]butyric acid,
4-[3-[3-[2,2-bis(4-isobutylphenyl)ethyl]benzoyl]indol-1-yl]butyric acid,
4-[3-[4-[1-(4-isobutylphenyl)hexyloxy]benzoyl]indol-1-yl]butyric acid,
4-[3-[4-[1-(4-isobutylphenyl)butoxy]benzoyl]indol-1-yl]butyric acid,
4-[3-[4-[1-(4-isobutylphenyl)pentyloxy]benzoyl]indol-1-yl]butyric acid,
4-[3-[4-[1-(4-isobutylphenyl)heptyloxy]benzoyl]indol-1-yl]butyric acid,
4-[3-[4-[1-(4-isobutylphenyl)octyloxy]benzoyl]indol-1-yl]butyric acid,
4-[3-[3-[1-(4-isobutylphenyl)hexylamino]benzoyl]indol-1-yl]butyric acid,
4-[3-[3-[1-(4-isobutylphenyl)propylamino]benzoyl]indol-1-yl]butyric acid,
4-[3-[3-[1-(4-isobutylphenyl)butylamino]benzoyl]indol-1-yl]butyric acid and
4-[3-[3-[1-(4-isobutylphenyl)pentylamino]benzoyl]indol-1-yl]butyric acid.

5. A compound of claim 4, which is R or S configuration the compound selected from the group consisting of:
4-[3-[4-[1-(4-isobutylphenyl)ethoxy]benzoyl]indol-1-yl]butyric acid,
4-[3-[4-[1-(4-isobutylphenyl)hexyloxy]benzoyl]indol-1-yl]butyric acid,
4-[3-[4-[1-(4-isobutylphenyl)butoxy]benzoyl]indol-1-yl]butyric acid,
4-[3-[4-[1-(4-isobutylphenyl)pentyloxy]benzoyl]indol-1-yl]butyric acid,
4-[3-[4-[1-(4-isobutylphenyl)heptyloxy]benzoyl]indol-1-yl]butyric acid,
4-[3-[4-[1-(4-isobutylphenyl)octyloxy]benzoyl]indol-1-yl]butyric acid,
4-[3-[3-[1-(4-isobutylphenyl)hexylamino]benzoyl]indol-1-yl]butyric acid,
4-[3-[3-[1-(4-isobutylphenyl)propylamino]benzoyl]indol-1-yl]butyric acid,
4-[3-[3-[1-(4-isobutylphenyl)butylamino]benzoyl]indol-1-yl]butyric acid and
4-[3-[3-[1-(4-isobutylphenyl)pentylamino]benzoyl]indol-1-yl]butyric acid.

6. 4-[3-[4-[1-(4-isobutylphenyl)pentyloxy]benzoyl]indol-1-yl]butyric acid.

7. (S)-4-[3-[4-[1-(4-isobutylphenyl)pentyloxy]benzoyl]indol-1-yl]butyric acid.

8. A pharmaceutical composition comprising a compound of claim 1 or pharmaceutically acceptable salt thereof in association with a pharmaceutically acceptable, substantially non-toxic carrier or excipient.

9. A method for treating or preventing testosterone 5α-reductase-mediated diseases, which comprises administering an effective amount of the compound of claim 1 or pharmaceutically acceptable salt thereof, to humans or animals.

10. The method of claim 9, in which testosterone 5α-reductase mediated disease is prostatic hypertrophy.

* * * * *